US008053191B2

(12) United States Patent
Blake

(10) Patent No.: US 8,053,191 B2
(45) Date of Patent: Nov. 8, 2011

(54) ITERATIVE NUCLEIC ACID ASSEMBLY USING ACTIVATION OF VECTOR-ENCODED TRAITS

(75) Inventor: William J. Blake, Jamaica Plain, MA (US)

(73) Assignee: Westend Asset Clearinghouse Company, LLC, Boston, MA (US)

( * ) Notice: Subject to any disclaimer, the term of this patent is extended or adjusted under 35 U.S.C. 154(b) by 472 days.

(21) Appl. No.: 11/897,939

(22) Filed: Aug. 31, 2007

(65) Prior Publication Data

US 2009/0155858 A1    Jun. 18, 2009

Related U.S. Application Data

(60) Provisional application No. 60/841,843, filed on Aug. 31, 2006.

(51) Int. Cl.
*C12Q 1/68* (2006.01)
*C07H 21/02* (2006.01)
(52) U.S. Cl. ..................... 435/6.12; 536/22.1
(58) Field of Classification Search ............. 435/6, 91.2; 536/22.1
See application file for complete search history.

(56) References Cited

U.S. PATENT DOCUMENTS

| | | |
|---|---|---|
| 5,093,251 A | 3/1992 | Richards |
| 5,096,825 A | 3/1992 | Barr |
| 5,132,215 A | 7/1992 | Jayaraman |
| 5,395,750 A | 3/1995 | Dillon |
| 5,459,039 A | 10/1995 | Modrich |
| 5,498,531 A | 3/1996 | Jarrell |
| 5,556,750 A | 9/1996 | Modrich |
| 5,605,793 A | 2/1997 | Stemmer |
| 5,679,522 A | 10/1997 | Modrich |
| 5,695,940 A | 12/1997 | Drmanac |
| 5,702,894 A | 12/1997 | Modrich |
| 5,750,335 A | 5/1998 | Gifford |
| 5,766,550 A | 6/1998 | Kaplan |
| 5,780,272 A | 7/1998 | Jarrell |
| 5,795,714 A | 8/1998 | Cantor |
| 5,834,252 A | 11/1998 | Stemmer |
| 5,858,754 A | 1/1999 | Modrich |
| 5,861,482 A | 1/1999 | Modrich |
| 5,871,902 A | 2/1999 | Weininger |
| 5,877,280 A | 3/1999 | Wetmur |
| 5,912,129 A | 6/1999 | Vinayagamoorthy |
| 5,916,794 A | 6/1999 | Chandrasegaran |
| 5,922,539 A | 7/1999 | Modrich |
| 5,928,905 A | 7/1999 | Stemmer |
| 5,942,609 A | 8/1999 | Hunkapiller |
| 6,008,031 A | 12/1999 | Modrich |
| 6,013,440 A | 1/2000 | Lipshutz |
| 6,027,877 A | 2/2000 | Wagner |
| 6,103,463 A | 8/2000 | Chetverin |
| 6,110,668 A | 8/2000 | Strizhov |
| 6,136,568 A | 10/2000 | Hiatt |
| 6,143,527 A | 11/2000 | Pachuk |
| 6,150,102 A | 11/2000 | Mills |
| 6,150,141 A | 11/2000 | Jarrell |
| 6,165,793 A | 12/2000 | Stemmer |
| 6,242,211 B1 | 6/2001 | Peterson |
| 6,248,521 B1 | 6/2001 | Van Ness |
| 6,261,797 B1 | 7/2001 | Sorge |
| 6,277,632 B1 | 8/2001 | Harney |
| 6,287,825 B1 | 9/2001 | Weissman |
| 6,287,861 B1 | 9/2001 | Stemmer |
| 6,322,971 B1 | 11/2001 | Chetverin |
| 6,326,489 B1 | 12/2001 | Church |
| 6,346,399 B1 | 2/2002 | Weissman |
| 6,355,412 B1 | 3/2002 | Stewart |
| 6,358,712 B1 | 3/2002 | Jarrell |
| 6,372,429 B1 | 4/2002 | Sharon |
| 6,372,434 B1 | 4/2002 | Weissman |
| 6,375,903 B1 | 4/2002 | Cerrina |
| 6,376,246 B1 | 4/2002 | Crameri |
| 6,410,220 B1 | 6/2002 | Hodgson |
| 6,472,184 B1 | 10/2002 | Hegemann |
| 6,489,146 B2 | 12/2002 | Stemmer |
| 6,495,318 B2 | 12/2002 | Harney |
| 6,506,603 B1 | 1/2003 | Stemmer |
| 6,509,156 B1 | 1/2003 | Stewart |
| 6,521,427 B1 | 2/2003 | Evans |
| 6,534,271 B2 | 3/2003 | Furste |
| 6,537,776 B1 | 3/2003 | Short |
| 6,586,211 B1 | 7/2003 | Stahler |
| 6,593,111 B2 | 7/2003 | Baric |

(Continued)

FOREIGN PATENT DOCUMENTS

EP    0259160    3/1988

(Continued)

OTHER PUBLICATIONS

Aihara, H. et al. "A Conformational Switch Controls the DNA Cleavage Activity of λ Integrase," Molecular Cell, 12:187-198, (Jul. 2003).
Altschul, S., et al. "Basic local alignment search tool," J Mol Biol., 215(3):403-10, (1990).
Altschul, S. & Koonin, E. "Iterated profile searches with PSI-BLAST—a tool for discovery in protein databases," Trends Biochem. Sci., 23:444-447, (Nov. 1998).
Andersen, J., et al. "New Unstable Variants of Green Fluorescent Protein for Studies of Transient Gene Expression in Bacteria," Applied and Environmental Microbiology, 64(6):2240-2246 (Jun. 1998).
Au, L., et al. "Gene Synthesis by a LCR-Based Approach: High•Level Production of Leptin-L54 Using Synthetic Gene in *Escherichia coli*," Biochemical and Biophysical Research Communications, 248:200-203 (1998).
Bartsevich, V., et al. "Engineered Zinc Finger Proteins for Controlling Stem Cell Fate," Stem Cells, 21:632-637 (2003).
Böltner, D., et al. "R391: A Conjugative Integrating Mosaic Comprised of Phage, Plasmid, and Transposon Elements," J. of Bacteriology, 184(18):5158-5169 (Sep. 2002).

(Continued)

*Primary Examiner* — Prabha Chunduru
(74) *Attorney, Agent, or Firm* — Greenberg Traurig, LLP; Jennifer A. Camacho; Natalie Salem

(57) ABSTRACT

Certain aspects of the present invention provide methods for assembling nucleic acid molecules using iterative activation of one or more vector-encoded traits to progressively assemble a longer nucleic acid insert. Aspects of the invention also provide kits, compositions, devices, and systems for assembling synthetic nucleic acids using iterative activation of one or more vector-encoded traits.

21 Claims, 16 Drawing Sheets

U.S. PATENT DOCUMENTS

| | | | |
|---|---|---|---|
| 6,632,641 B1 | 10/2003 | Brennan | |
| 6,664,112 B2 | 12/2003 | Mulligan | |
| 6,670,127 B2 | 12/2003 | Evans | |
| 6,946,296 B2 | 9/2005 | Patten | |
| 7,183,406 B2 | 2/2007 | Belshaw | |
| 7,262,031 B2 | 8/2007 | Lathrop | |
| 7,303,872 B2 | 12/2007 | Sussman | |
| 7,323,320 B2 | 1/2008 | Oleinikov | |
| 7,563,600 B2 | 7/2009 | Oleinikov | |
| 2001/0031483 A1 | 10/2001 | Sorge | |
| 2002/0025561 A1 | 2/2002 | Hodgson | |
| 2002/0132308 A1 | 9/2002 | Liu | |
| 2003/0017552 A1 | 1/2003 | Jarrell | |
| 2003/0044980 A1 | 3/2003 | Mancebo | |
| 2003/0054390 A1 | 3/2003 | Crameri | |
| 2003/0068643 A1 | 4/2003 | Brennan | |
| 2003/0082630 A1 | 5/2003 | Kolkman | |
| 2003/0171325 A1 | 9/2003 | Gascoyne | |
| 2003/0175907 A1 | 9/2003 | Frazer | |
| 2003/0186226 A1 | 10/2003 | Brennan | |
| 2003/0198948 A1 | 10/2003 | Stahler | |
| 2003/0215837 A1 | 11/2003 | Frey | |
| 2003/0224521 A1 | 12/2003 | Court | |
| 2004/0002103 A1 | 1/2004 | Short | |
| 2004/0005673 A1 | 1/2004 | Jarrell | |
| 2004/0096891 A1 | 5/2004 | Bennett | |
| 2004/0166567 A1 | 8/2004 | Santi | |
| 2005/0053997 A1 | 3/2005 | Evans | |
| 2005/0069928 A1 | 3/2005 | Nelson | |
| 2005/0089889 A1 | 4/2005 | Ramsing | |
| 2005/0106606 A1 | 5/2005 | Parker | |
| 2005/0118628 A1 | 6/2005 | Evans | |
| 2005/0208503 A1 | 9/2005 | Yowanto | |
| 2005/0221340 A1 | 10/2005 | Evans | |
| 2005/0227235 A1 | 10/2005 | Carr | |
| 2005/0227316 A1 | 10/2005 | Santi | |
| 2005/0255477 A1 | 11/2005 | Carr | |
| 2006/0008833 A1 | 1/2006 | Jacobson | |
| 2006/0127920 A1 | 6/2006 | Church | |
| 2006/0127926 A1 | 6/2006 | Belshaw | |
| 2006/0160138 A1* | 7/2006 | Church et al. | 435/7.1 |
| 2006/0194214 A1 | 8/2006 | Church | |
| 2007/0231805 A1 | 10/2007 | Baynes | |
| 2008/0261300 A1 | 10/2008 | Santi | |
| 2008/0274510 A1 | 11/2008 | Santi | |
| 2008/0300842 A1 | 12/2008 | Govindarajan | |
| 2009/0087840 A1* | 4/2009 | Baynes et al. | 435/6 |
| 2009/0305233 A1 | 12/2009 | Borovkov | |

FOREIGN PATENT DOCUMENTS

| | | |
|---|---|---|
| EP | 1015576 | 5/2005 |
| EP | 1159285 | 5/2005 |
| WO | WO90/00626 | 1/1990 |
| WO | WO93/17126 | 9/1993 |
| WO | WO96/33207 | 10/1996 |
| WO | WO97/35957 | 10/1997 |
| WO | WO98/38299 | 9/1998 |
| WO | WO00/29616 | 5/2000 |
| WO | WO00/46386 | 8/2000 |
| WO | WO00/49142 | 8/2000 |
| WO | WO02/081490 | 10/2002 |
| WO | WO02/095073 | 11/2002 |
| WO | WO03/033718 | 4/2003 |
| WO | WO03/054232 | 7/2003 |
| WO | WO03/060084 | 7/2003 |
| WO | WO03/064611 | 8/2003 |
| WO | WO03/085094 | 10/2003 |
| WO | WO03/100012 | 12/2003 |
| WO | WO2004/024886 | 3/2004 |
| WO | WO2005/089110 | 9/2005 |
| WO | WO2005/103279 | 11/2005 |
| WO | WO2005/123956 | 12/2005 |
| WO | WO2006/044956 | 4/2006 |
| WO | WO2006/049843 | 5/2006 |
| WO | WO2006/127423 | 11/2006 |
| WO | WO2007/008951 | 1/2007 |
| WO | WO2007/009082 | 1/2007 |
| WO | WO2007/075438 | 7/2007 |
| WO | WO2007/087347 | 8/2007 |
| WO | WO2007/117396 | 10/2007 |
| WO | WO2007/123742 | 11/2007 |
| WO | WO2007/136833 | 11/2007 |
| WO | WO2007/136835 | 11/2007 |
| WO | WO2007/136840 | 11/2007 |
| WO | WO2008/024319 | 2/2008 |
| WO | WO2008/054543 | 5/2008 |
| WO | WO2008/076368 | 6/2008 |
| WO | WO2008/130629 | 10/2008 |

OTHER PUBLICATIONS

Booth, P., et al. "Assembly and cloning of coding sequences for neurotrophic factors directly from genomic DNA using polymerase chain reaction and uracil DNA glycosylase," Gene, 146(2):303-308 (1994).

Brown, C. "BioBricks to help reverse-engineer life," URL: http://eetimes.com/news/latest/showArticle.ihtml?articleID=21700333, (Jun. 11, 2004).

Burge, C. & Karlin, S. "Prediction of complete gene structures in human genomic DNA," J Mol Biol., 268(1):78-94, (1997).

Cai, Q., et al. "Immunogenicity of Polyepitope Libraries Assembled by Epitope Shuffling: An Approach to the Development of Chimeric Gene Vaccination Against Malaria," Vaccine, 23:267-277, (2004).

Carr, P., et al. "Protein-mediated error-correction for *de novo* DNA synthesis," Nucleic Acids Research, 32(20), e162 (9 pages), (2004).

Caruthers, et al. "CXV. Total synthesis of the structural gene for an alanine transfer RNA from yeast. Enzymic joining to form the total DNA duplex," J Mol Biol., 72(2):475-92, (Dec. 28, 1972).

Cassell, G. & Segall, A. "Mechanism of Inhibition of Site-specific Recombination by the Holliday Junction-trapping Peptide WKHYNY: Insights into Phage I integrase-mediated Strand Exchange," J. Mol. Biol., 327:413-429, (2003).

Chalmers, F. & Curnow, K. "Scaling up the ligase chain reaction-based approach to gene synthesis," BioTechniques, 30(2):249-252, (Feb. 2001).

Chan, L. et al. "Refactoring bacteriophage T7," Molecular Systems Biol., doi: 10.1038/msb4100025, (Published online Sep. 13, 2005).

Che, A. "BioBricks++: Simplifying Assembly of Standard DNA Components," [Online] XP002412778, URL: http://austinche.name/docs/bbpp.pdf, (Jun. 9, 2004).

Chen, H., et al. "A new method for the synthesis of a structural gene," Nucleic Acids Research, 18(4):871-878 (Feb. 1990).

Cherepanov, A., et al. "Joining of short DNA oligonucleotides with base pair mismatches by T4 DNA ligase," J Biochem., 129(1):61-68, (Jan. 2001).

Chetverin, A. & Kramer, F. "Sequencing pool of Nucleic Acids on Oligonucleotide arrays," Biosystems, 30:215-231, (1993).

Chevalier, B., et al. "Design, Activity, and Structure of a Highly Specific Artificial Endonuclease," Molecular Cell, 10:895-905 (Oct. 2002).

Chevalier, B. & Stoddard, B. "Homing endonucleases: structural and functional insight into the catalysts of intron/intein mobility," Nucl. Acids Res., 29(18):3757-3774 (2001).

Coco, W., et al. "Growth Factor Engineering by Degenerate Homoduplex Gene Family Recombination," Nature Biotechnology, 20:1246-1250, (Dec. 2002).

Crameri, A., et al. "Improved Green Fluorescent Protein by Molecular Evolution Using DNA Shuffling," Nature Biotechnology, 14:315-319, (Mar. 1996).

Dedkova, L. et al. "Enhanced D-Amino Acid Incorporation into Protein by modified Ribosomes," J. Am. Chem. Soc., 125:6616-6617, (2003).

Evans, E.& Alani, E. "Roles for Mismatch Repair Factors in Regulating Genetic Recombination," Molecular & Cellular Biology, 20(21):7839-7844 (Nov. 2000).

Ferretti, L. et al. "Total synthesis of a gene for bovine rhodopsin," PNAS, 83:599-603 (Feb. 1986).

Fisch, I. et al. "A Strategy of Exon Shuffling for Making Large Peptide Repertoires Displayed on Filamentous Bacteriophage," Proceedings of the National Academy of Sciences of USA, 93:7761-7766, (Jul. 1996).

Fleck, O. & Nielsen O. "DNA Repair," J. Cell Science, 117(4):515-517 (2004).
Gao, X. et al. "Thermodynamically balanced inside-out (TBIO) PCR-based gene synthesis: a novel method of primer design for high fidelity assembly of longer gene sequences," Nucleic Acids Research, 31(22):e143 (11 pages) (2003).
Gardner, T., et al. "Construction of a genetic toggle switch in *Escherichia coli*," Nature, 403(20):339-342 (Jan. 2000).
Gibbs, W. "Synthetic Life," Scientific American, [Online] URL: htto://www.sciam.com/orintversion.cfm?articleID=0009FCA4, (Apr. 26, 2004).
Goler, J. "BioJADE: A Design and Simulation Tool for Synthetic Biological Systems," MIT Computer Science and Artificial Intelligence Laboratory, AI Technical Report, [Online] URL: http://dspace.mit.edu/bitstream/1721.1/30475/2/MIT-CSAIL-TR-2004-036.pdf, (May 2004).
Guntas, G., et al. "A molecular switch created by in vitro recombination of nonhomologous genes," Chem. & Biol., 11:1483-1487 (Nov. 2004).
Guntas, G., et al. "Directed Evolution of Protein Switches and Their Application to the Creation of Ligand-Binding Proteins," Proc. Natl. Acad. Sci. USA, 102(32):11224-11229 (Aug. 9, 2005).
Gupta, N., et al. "Studies on Polynucleotides, LXXXVIII. Enzymatic Joining of Chemically Synthesized Segments Corresponding to the Gene for Alanine-tRNA," PNAS, 60:1338-1344, (1968).
Hansen, W. & Kelley M. "Review of Mammalian DNA Repair and Transcriptional Implications," J. Pharmacol. & Exper. Therapeutics, 295(1):1-9, (2000).
Hecker, K. "Error Analysis of Chemically Synthesized Polynucleotides," BioTechniques, 24(2):256-260, (Feb. 1998).
Heeb, S., et al. "Small, Stable Shuttle Vectors Based on the Minimal pVS1 Replicon for Use in Gram-Negative Plant-Associated Bacteria," MPMI, 13(2):232-237 (2000).
Henegariu et al. "Multiplex PCR: critical parameters and step-by-step protocol" Biotechniques, 23(3): 504-511, (Sep. 1997).
Hermeling, S., et al. "Structure-Immunogenicity Relationships of Therapeutic Proteins," Pharmaceutical Research, 21(6):897-903, (Jun. 2004).
Higuchi, R., et al. "A general method of in vitro preparation and specific mutagenesis of DNA fragments: study of protein and DNA interactions," Nucleic Acids Research, 16(15):7351-7367 (1988).
Hoover D. & Lubkowski, J. "DNAWorks: an automated method for designing oligonucleotides for PCR-based gene synthesis," Nucleic Acids Research, 30(10):e43 (7 pages), (2002).
Horton, R., et al. "Engineering hybrid genes without the use of restriction enzymes: Gene splicing by overlap extension," Gene, 77:61-68, (1989).
Ibrahim, E., et al. "Serine/arginine-rich protein-dependent suppression of exon skipping by exonic splicing enhancers," Proc. Natl. Acad. Sci. U S A, 102(14):5002-5007, (Apr. 5, 2005).
Ito R. et al. "Novel muteins of human tumor necrosis factor alpha" Biochimica et Biophysica Acta, 1096 (3): 245-252 (1991).
Jayaraman, et al. "A PCR-mediated Gene synthesis strategy involving the assembly of oligonucleotides representing only one of the strands," Biotechniques, 12(3):392-398, (1992).
Jayaraman et al. "Polymerase chain-reaction mediated gene synthesis: synthesis of a gene coding for Isozyme C of Horseradish Peroxidase" PNAS 88:4084-4088, (May 1991).
Jones, T.D., et al. "The Development of a Modified Human IFN-alpha2b Linked to the Fc Portion of Human IgG1 as a Novel Potential Therapeutic for the Treatment of Hepatitis C Virus Infection," Journal of Interferon & Cytokine Research, 24:560-572, (2004).
Khaitovich, P., et al. "Characterization of functionally active subribosomal particles from *Thermus aquaticus*," Proc. Natl. Acad. Sci., 96:85-90 (Jan. 1999).
Kisselev, L., et al. "Termination of translation: interplay of mRNA, rRNAS and release factors?," The EMBO J., 22(2):175-182, (2003).
Kitamura, Koichiro et al. "Construction of Block-Shuffled Libraries of DNA for Evolutionary Protein Engineering: Y-Ligation-Based Block Shuffling." Protein Engineering, 15(10): 843-853, (Oct. 2002).
Kleppe K., et al. "Studies of polynucleotides: repair replication of short synthetic DNA's as catalyzed by DNA polymerases," J. Mol. Biol. 56:341-361, (1971).
Kodumal., S., et al. "Total synthesis of long DNA sequences: Synthesis of a contiguous 32-kb polyketide synthase gene cluster," PNAS, 101(44):15573-15578, (Nov. 2, 2004).
Kolisnychenko, V., et al. "Engineering a Reduced *Escherichia coli* Genome," Genome Research, 12:640-647, (2002).
Kotsopoulou, E., et al. "A Rev-Independent Human Immunodeficiency Virus Type 1 (HIV-1)-Based Vector That Exploits a Codon-Optimized HIV-1 gag-pol Gene," Journal of Virology, 74(10):4839-4852, (May 2000).
Kowalczykowski, S. "Initiation of genetic recombination and recombination-dependent replication," TIBS, 25:156-165, (Apr. 2000).
Kowalczykowski, S. "In vitro reconstitution of homologous recombination reactions," Experientia, 50:204-215, (1994).
Lamers, M., et al. "ATP Increases the Affinity between MutS ATPase Domains," J. Biol. Chem., 279(42):43879-43885, (Oct. 15, 2004).
Lashkari, D., et al. "An automated multiplex oligonucleotide synthesizer: Development of high throughput, low cost DNA synthesis," PNAS, 92:7912-7915, (Aug. 1995).
Lee, K., et al. "Genetic approaches to Studying Protein Synthesis: Effects of Mutations at ψ1516 and A535 in *Escherichia coli* 16S rRNA," J. Nutr., 131:2994S-3004S, (2001).
Lewis, J. & Hatfull, G. "Control of directionality in intergrase-mediated recombination: examination of recombination directionality factors (RDFs) including Xis and Cox proteins," Nucl. Acids Res., 29(11):2205-2216 (2001).
Li, C., & Evans, R. "Ligation independent cloning irrespective of restriction site compatibility," Nucl. Acids Res., 25(20):4165-4166, (1997).
Li, L. & Chandrasegaran, S. "Alteration of the cleavage distance of Fok I restriction endonuclease by insertion mutagenesis." Proc Natl Acad Sci U S A, 90:2764-2768, (Apr. 1993).
Link, A., et al. "Methods for generating precise deletions and insertions in the genome of wild-type *Escherichia coli*: Application to open reading frame characterization," J. Bacteriol., 179(20):6228-6237, (Oct. 1997).
Liu, W. et al. "Genetic Incorporation of Unnatural Amino Acids Into Proteins in Mammalian Cells," Nature Methods, 4(3):239-244, (Mar. 2007).
Luo, P., et al. "Development of a Cytokine Analog with Enhanced Stability Using Computational Ultrahigh Throughput Screening," Protein Science, 11:1218-1226, (2002).
Lutz, S., et al. "Homology-Independent Protein Engineering," Current Opinion in Biotechnology, 11(4):319-324, (Aug. 2000).
Mandecki et al. "FokI method of gene synethsis" Gene, 68:101-107 (1988).
Mannervik, B. "Optimizing the Heterologous Expression of Glutathione Transferase," Methods in Enzymology, 401:254-265, (2005).
Mezard, C., et al. "Recombination Between Similar But Not Identical DNA Sequences During Yeast Transformation Occurs Within Short Stretches of Identity," Cell, 70:659-670, (Aug. 21, 1992).
Miick, S., et al. "Crossover isomer bias is the primary sequence-dependent property of immobilized Holliday junctions," Proc. Natl. Acad. Sci. USA, 94:9080-9084, (Aug. 1997).
Milton, R., et al. "Total Chemical Synthesis of a D-Enzyme: The Enantiomers of HIV-1 Protease Show Demonstration of Reciprocal Chiral Substrate Specificity," Science, 256:1445-1448, (Jun. 5, 1992).
Modrich, P. "Strand-specific Mismatch Repair in Mammalian Cells," J. Biol. Chem., 272(40): 24727-24730, (Oct. 3, 1997).
Moore, G. & Maranas C. "Computational Challenges in Combinatorial Library Design for Protein Engineering," AIChE Journal, 50(2):262-272, (Feb. 2004).
Nakamaye, K., et al. "Direct sequencing of polymerase chain reaction amplified DNA fragments through the incorporation of deoxynucleoside-thiotriphosphates," Nucleic Acids Research, 16(21):9947-9959, (1988).
Nakamura, Y. & Ito, K. "How protein reads the stop codon and terminates translation," Genes to Cells, 3:265-278, (1998).
Nakayama, M., and Ohara, A. "A system using convertible vectors for screening soluble recombinant proteins produced in *Escherichia coli* from randomly fragmented cDNAs," Bioch. and Biophys. Res. Comm., 312:825-830, (2003).

Ness, J., et al. "Synthetic Shuffling Expands Functional Protein Diversity by Allowing Amino Acids to Recombine Independently" Nature Biotechnology, 20:1251-1255, (Dec. 2002).

Nilsson, L., et al. "Improved Heterologous Expression of Human Glutathione Transferase A4-4 by Random Silent Mutagenesis of Codons in the 5' Region," Biochemica et Biophysica Acta, 1528: 101-106, (2001).

Nilsson P., et al. "Real-Time monitoring of DNA manipulations using biosensor technology," Analytical Biochemistry, 224:400-408, (1995).

Noirot, P. & Kolodner, R. "DNA Strand Invasion Promoted by *Esherichia coli* RecT Protein," J. Biol. Chem., 273(20):12274-12280, (May 15, 1998).

Novy, R., et al. "Ligation Independent Cloning: Efficient Directional Cloning of PCR Products," Novagen, Inc., InNovations, 5:1-3, (http://www.emdbiosciences.com/html/NVG/inNovations.html), (1996).

Osawa, S., et al. "Recent Evidence for Evolution of the Genetic Code," Microbiological Reviews, 56(1):229-264, (Mar. 1992).

Osborn, A. M., and Boltner, D. "When phage, plasmids, and transposons collide: genomic islands, and conjugative and mobilizable-transposons as a mosaic continuum," Plasmid, 48:202-212, (2002).

Pachuk C.J. et al. "Chain reaction cloning: one step method for directional ligation of multiple DNA fragments" Gene, 243(1-2): 19-25 (2000).

Pan X. & Weissman, S. "An approach for global scanning of single nucleotide variations," PNAS, 99(14):9346-9351, (Jul. 9, 2002).

Parr, R. & Ball, J. "New donor vector for generation of histidine-tagged fusion proteins using the Gateway Cloning System," Plasmid, 49:179-183, (2003).

Peters, J. & Craig, N. "Tn7: Smarter Than We Thought," Nature, 2:806-814, (Nov. 2001).

Pòsfai, G., et al. "In vivo excision and amplification of large segments of the *Escherichia coli* genome," Nucl. Acids Res., 22(12):2392-2398, (1994).

Pòsfai, G., et al. "Markerless gene replacement in *Escherichia coli* stimulated by a double-strand break in the chromosome," Nucl. Acids Res., 27(22):4409-4415, (1999).

Prodromou, C. & Pearl L. "Recursive PCR: A Novel Technique for Total Gene Synthesis" Protein Engineering, 5(8):827-829 (1992).

Regalado, A. "Next Dream for Venter: Create Entire Set of Genes From Scratch," Wall Street Journal, A1, (Jun. 29, 2005).

Reyrat, J., et al. "Counterselectable Markers: Untapped Tools for Bacterial Genetics and Pathogenesis," Infection and Immunity, 66(9):4011-4017, (Sep. 1998).

Richmond, K., et al., "Amplification and assembly of chip-eluted DNA (AACED): a method for high-throughput gene synthesis," Nucleic Acids Research, 32(17): 5011-5018 (2004).

Rouillard, J. et al. "Gen2Oligo: Oligonucleotide design for in vitro gene synthesis," Nucleic Acids Research, 32: W176-W180, (2004).

Rouwendal, G., et al. "Enhanced Expression in Tobacco of the Gene Encoding Green Fluorescent Protein by Modification of its Codon Usage," Plant Molecular Biology, 33:989-999, (1997).

Sa-Ardyen, P., et al. "The flexibility of DNA double crossover molecules," Biophys. J., 84:3829-3837, (Jun. 2003).

Saiki, R., et al. "Analysis of enzymatically amplified beta-globin and HLA-DQ alpha DNA with allele-specific oligonucleotide probes," Nature, 324(6093):163-166, (Nov. 13, 1986).

Sakabe, N., et al. "A Bioinformatics Analysis of Alternative Exon Usage in Human Genes Coding for Extracellular Matrix Proteins," Genetics and Molecular Research, 3(4):532-544, (2004).

Sakamoto, K., et al. "Site-Specific Incorporation of an Unnatural Amino Acid Into Proteins in Mammalian Cells," Nucleic Acids Research, 30(21):4692-4699, (2002).

Saks, M., et al. "An Engineered Tetrahymena tRNA$^{Gln}$, for in Vivo Incorporation of Unnatural Amino Acids into Proteins by Nonsense Suppression," J. of Biol. Chem., 271(38):23169-23175, (Sep. 20, 1996).

Saks, M. "Making sense out of nonsense," PNAS, 98(5):2125-2127, (Feb. 27, 2001).

Salyers, A., et al. "Conjugative Transposons: an Unusual and Diverse Set of Integrated Gene Transfer Elements," Microbiological Reviews, 59(4):579-590, (Dec. 1995).

Sato, T., et al. "Production of menaquinone (vitamin K2)-7 by *Bacillus subtilis*," J. of Bioscience and Engineering, 91(1):16-20, (2001).

Semizarov, D., et al. "Stereoisomers of Deoxynucleoside 5'-Triphosphates as Substrates for Template-dependent and-independent DNA Polymerases," J. of Biol. Chem., 272(14):9556-9560, (Apr. 4, 1997).

Sgaramella, V., et al. "Studies of polynucleotides, C.: A novel joining reaction catalyzed by T4-polynucleotide ligase", PNAS, 67(3):1468-1475, (Nov. 1970).

Shabarova, Z., et al., "Chemical ligation of DNA: the first non-enzymatic assembly of a biologically active gene," Nucleic Acids Research, 19(15):4247-4251, (1991).

Shao, Z., et al. "Random-Priming in Vitro Recombination: An Effective Tool for Directed Evolution," Nucleic Acids Research, 26(2):681-683, (1998).

Sieber, V., et al. "Libraries of Hybrid Proteins From Distantly Related Sequences," Nature Biotechnology, 19:456-460, (May 2001).

Simon, D., et al. "N-methyl-D-aspartate receptor antagonists disrupt the formation of a mammalian neural map" Proc Natl Acad Sci USA, 89:10593-10597, (Nov. 1992).

Smith, J. & Modrich, P. "Mutation Detection with MutH, MutL, and MutS Mismatch Repair Proteins," Proc. Natl. Acad. Sci. USA, 93:4374-4379, (Apr. 1996).

Soderlind, E., et al. "Domain libraries: Synthetic diversity for de novo design of antibody V-regions," Gene, 160:269-272, (1995).

Sprinzl, M. & Vassilenko, K. "Compilation of tRNA sequences and sequences of tRNA genes," Nucleic Acids Research, 33:D139-D140 (2005).

Stemmer W. P. C. "DNA shuffling by random fragmentation and reassembly: in vitro recombination for molecular evolution," Proc. Natl. Acad. Sci. USA, 91:10747-10751, (1994).

Stemmer W. P. et al. "Single-step assembly of a gene and entire plasmid from large numbers of oligodeoxyribonucleotides" Gene, 164 (1): 49-53, (1995).

Steuer, S., et al. "Chimeras of the Homing Endonuclease Pi-SeeI and the Homologous Candida Tropicalis Intein: A Study to Explore the Possibility of Exchanging DNA-Binding Modules to Obtain Highly Specific Endonucleases With Altered Specificity," ChemBioChem., 5(2):206-213, (2004).

Strizhov N. et al. "A synthetic crylC gene, encoding a *Bacillus thuringiensis* delta-endotoxin, confers Spodoptera resistance in Alfalfa and Tobacco" PNAS, 93(26):15012-15017.

Tan, S., et al. "Zinc-finger protein-targeted gene regulation: Genomewide single-gene specificity," PNAS, 100(21):11997-12002, (Oct. 14, 2003).

Tian, J., et al. "Accurate multiplex gene synthesis from programmable DNA microchips," Nature, 432:1050-1054, (Dec. 2004).

Tsutakawa, S. & Morikawa, K. "The Structural Basis of Damaged DNA Recognition and Endonucleolytic Cleavage for Very Short Patch Repair Endonuclease," Nucleic Acids Research, 29(18):3775-3783, (2001).

Urata, H., et al. "Synthesis and properties of mirror-image DNA," Nucleic Acids Research, 20(13):3325-3332 (1992).

von Neumann, J. "The general and logical theory of automata," Pergamon Press, 5:288-326, (1948).

Waters, V. "Conjugation between bacterial and mammalian cells," Nature Genetics, 29:375-376, (Dec. 2001).

Weiler, J. & Hoheisel, J. "Combining the Preparation of Oligonucleotide Arrays and Synthesis of High-Quality Primers," Analytical Biochemistry, 243:218-227, (1996).

Wheeler, D., et al. "Database resources of the National Center for Biotechnology Information," Nucleic Acids Res., 29(1):11-16, (2001).

Wilgenbus, K. & Lichter, P. "DNA chip technology ante portas," J. Mol. Med, 77:761-768, (1999).

Xie, J. & Schultz, P. "An Expanding Genetic Code," Methods A Companion To Methods In Enzymology, 36:227-238, (2005).

Xiong, A., et al. "A simple, rapid, high-fidelity and cost-effective PCR-based two-step DNA synthesis method for long gene sequences," Nucleic Acids Research, 32(12):e98 (10 pages), (2004).

Xu, Y. & Kool, E. "A novel 5'-iodonucleoside allows efficient nonenzymatic ligation of single-stranded and duplex DNAs," Tetrahedron Letters, 38(32):5595-5598, (1997).

Xu, Y. & Kool, E. "High sequence fidelity in a non-enzymatic DNA autoligation reaction," Nucleic Acids Research, 27(3):875-881, (1999).

Xu, Y., et al. "Nonenzymatic autoligation in direct three-color detection of RNA and DNA point mutations," Nature Biotechnology, 19:148-152, (Feb. 2001).

Yoon, Y., et al. "Cre/loxP-mediated in vivo excision of large segments from yeast genome and their amplification based on the 2 um plasmid-derived system," Gene, 223:67-76, (1998).

Yoon, Y. & Koob, M. "Efficient cloning and engineering of entire mitochondrial genomes in *Escherichia coli* and transfer into transcriptionally active mitochondria," Nucleic Acids Research, 31(5):1407-1415, (2003).

Young, L., & Dong, Q. "Two-step Total Gene Synthesis Method" Nucleic Acids Research, 32(7):e59 (6 pages), (2004).

Zha, D., et al. "Assembly of Designed Oligonucleotides as an Efficient Method for Gene Recombination: A New Tool in Directed Evolution," ChemBioChem, 4:34-39, (2003).

Zhang, P. et al. "Rational Design of a Chimeric Endonuclease Targeted to NotI Recognition Site" Protein Engineering Design & Selection, 20(10):497-504, (Oct. 2007).

Zhang, Z., et al. "Selective Incorporation of 5-Hydroxytryptophan Into Proteins in Mammalian Cells," Proceedings of the National Academy of Sciences of the United States of America, 101(24):8882-8887, (Jun. 15, 2004).

Zhao, H., et al. "Molecular Evolution by Staggered Extension Process (StEP) in Vitro Recombination," Nature Biotechnology, 16:258-261, (Mar. 1998).

Zhou X. et al. "Microfluidic PicoArray synthesis of oligodeoxynucleotides and simultaneous assembling of multiple DNA sequences" Nucleic Acids Research, 32(18): 5409-5417 (2004).

International Search Report PCT/US2007/019209.

* cited by examiner

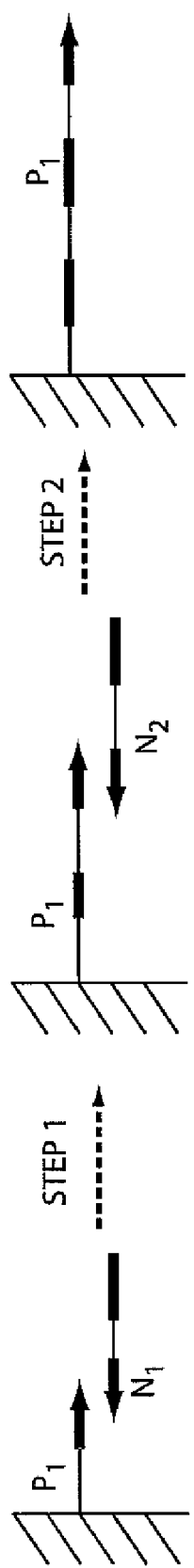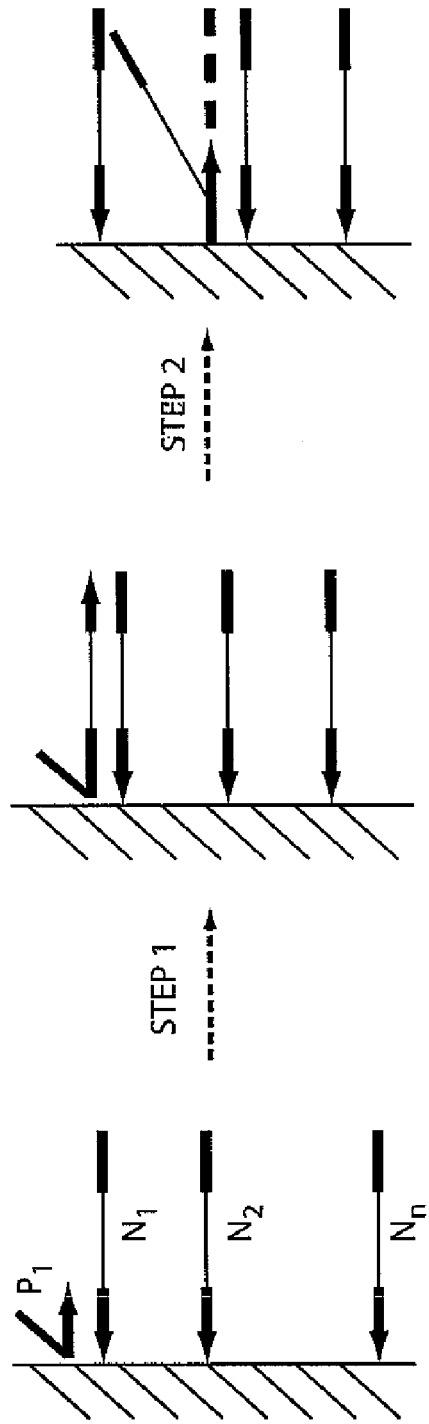
Fig. 2D
Fig. 2E

Figure 3
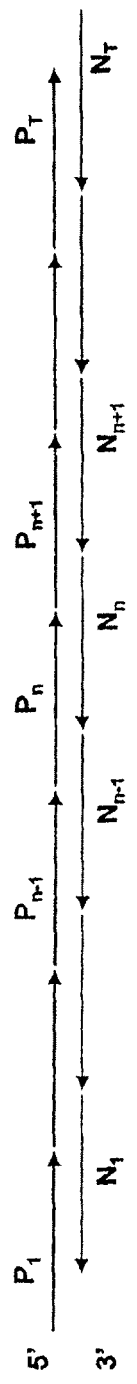
FIG. 3A
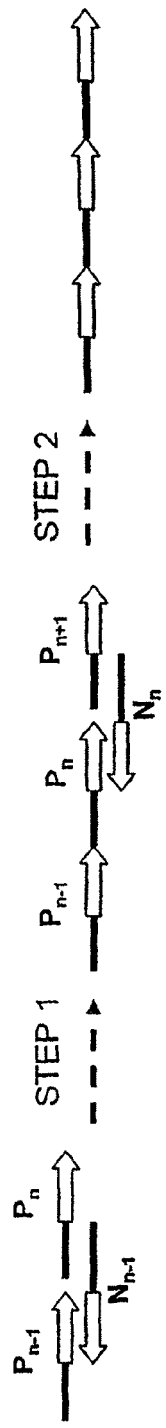
FIG. 3B

Figure 4
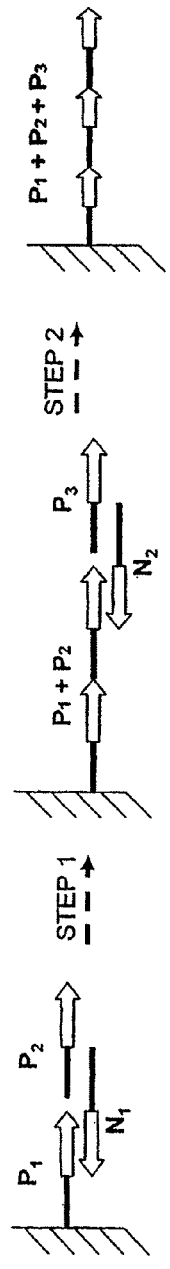
FIG. 4A
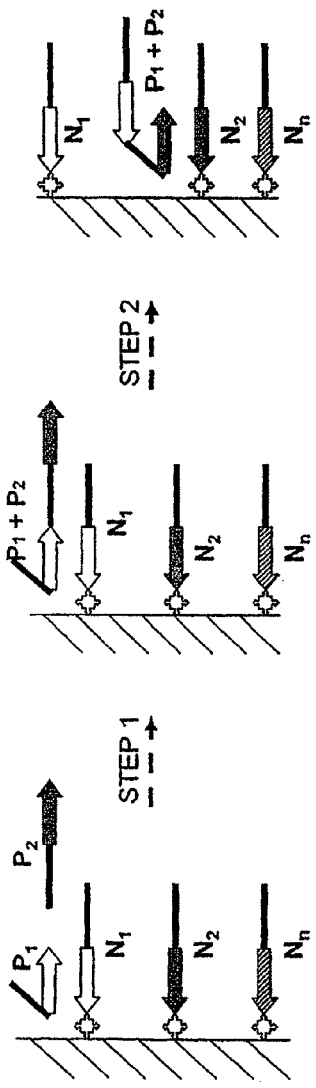
FIG. 4B pTS vector (tetracycline/spectinomycin selection)

pCK vector (chloramphenicol/kanamycin selection)

FIG. 12

[SEQ ID NO:5]

```
   BsmBI           -10          BtgZI        -35
TTCATGAGACGATCTCCTCCTTGATGCTGTAATAATAGCTCTAGGGCGATGTTAAGACAACATAT
ACTCTGCTAGAGGAAGGAACTACGACATTATTATCGAGATCCCGCTACAATTCTGTTGTATA
```

[SEQ ID NO:6]

[SEQ ID NO:7]

```
              BsmBI    -35                                                     -10              BtgZI
iiiiGGAGACGTTGACAACATGAAGTAAACAGCGTAAGATGTACCACACATGAAATTGCGATGAGGAAATCTA   CONSTRUCT
iiiiCCTCTGCAACTGTTGTACTTCATTTGTCGCATTCTACATGGTGTACTTTAACGCTACTCCTTTAGATACTC  DNA
```

[SEQ ID NO:8]

Recognition Site BsmBI:

5'...C G T C T C (N)₁ ▼ ...3'
3'...G C A G A G (N)₅ ▲ ...5'

Recognition Site BtgZI:

5'...G C G A T G (N)₁₀ ▼ ...3'
3'...C G C T A C (N)₁₄ ▲ ...5'

SEQUENCE LISTING

<160> NUMBER OF SEQ ID NOS: 8

<210> SEQ ID NO 1
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 1
catgagacga tctccttcct cttgatggct gtaataatag ctctagggcg atgttaagac    60

<210> SEQ ID NO 2
<211> LENGTH: 60
<212> TYPE: DNA
<213> ORGANISM: Artificial sequence
<220> FEATURE:
<223> OTHER INFORMATION: Synthetic oligonucleotide

```
<400> SEQUENCE: 2
gtcttaacat cgccctagag ctattattac agccatcaag aggaaggaga tcgtctcatg    60

<210> SEQ ID NO 3
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 3
ggagacgttg acaacatgaa gtaaacagcg taagatgtac cacatgaaat tgcgatgagg    60

<210> SEQ ID NO 4
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 4
catagatttc ctcatcgcaa tttcatgtgg tacatcttac gctgtttact tcatgttgtc    60

<210> SEQ ID NO 5
<211> LENGTH: 65
<212> TYPE: DNA
<213> ORGANISM: Artificial sequence
<220> FEATURE:
<223> OTHER INFORMATION: Synthetic polynucleotide

<400> SEQUENCE: 5
ttcatgagac gatctccttc ctcttgatgg ctgtaataat agctctaggg cgatgttaag    60
acaac                                                               65

<210> SEQ ID NO 6
<211> LENGTH: 61
<212> TYPE: DNA
<213> ORGANISM: Artificial sequence
<220> FEATURE:
<223> OTHER INFORMATION: Synthetic polynucleotide

<400> SEQUENCE: 6
gttgtcttaa catcgcccta gagctattat tacagccatc aagaggaagg agatcgtctc    60
a                                                                   61

<210> SEQ ID NO 7
<211> LENGTH: 67
<212> TYPE: DNA
<213> ORGANISM: Artificial sequence
<220> FEATURE:
<223> OTHER INFORMATION: Synthetic polynucleotide

<400> SEQUENCE: 7
ggagacgttg acaacatgaa gtaaacagcg taagatgtac cacatgaaat tgcgatgagg    60
aaatcta                                                             67

<210> SEQ ID NO 8
<211> LENGTH: 71
<212> TYPE: DNA
<213> ORGANISM: Artificial sequence
<220> FEATURE:
<223> OTHER INFORMATION: Synthetic polynucleotide

<400> SEQUENCE: 8
```

```
ctcatagatt tcctcatcgc aatttcatgt ggtacatctt acgctgttta cttcatgttg    60
tcaacgtctc c                                                         71
```

ITERATIVE NUCLEIC ACID ASSEMBLY USING ACTIVATION OF VECTOR-ENCODED TRAITS

RELATED APPLICATION

This application claims the benefit under 35 U.S.C. §119 (e) of U.S. provisional patent application Ser. No. 60/841,843, filed Aug. 31, 2006, the contents of which are incorporated herein by reference in their entirety.

FIELD OF THE INVENTION

Aspects of the application relate to nucleic acid assembly methods.

BACKGROUND

Recombinant and synthetic nucleic acids have many applications in research, industry, agriculture, and medicine. Recombinant and synthetic nucleic acids can be used to express and obtain large amounts of polypeptides, including enzymes, antibodies, growth factors, receptors, and other polypeptides that may be used for a variety of medical, industrial, or agricultural purposes. Recombinant and synthetic nucleic acids also can be used to produce genetically modified organisms including modified bacteria, yeast, mammals, plants, and other organisms. Genetically modified organisms may be used in research (e.g., as animal models of disease, as tools for understanding biological processes, etc.), in industry (e.g., as host organisms for protein expression, as bioreactors for generating industrial products, as tools for environmental remediation, for isolating or modifying natural compounds with industrial applications, etc.), in agriculture (e.g., modified crops with increased yield or increased resistance to disease or environmental stress, etc.), and for other applications. Recombinant and synthetic nucleic acids also may be used as therapeutic compositions (e.g., for modifying gene expression, for gene therapy, etc.) or as diagnostic tools (e.g., as probes for disease conditions, etc.).

Numerous techniques have been developed for modifying existing nucleic acids (e.g., naturally occurring nucleic acids) to generate recombinant nucleic acids. For example, combinations of nucleic acid amplification, mutagenesis, nuclease digestion, ligation, cloning and other techniques may be used to produce many different recombinant nucleic acids. Chemically synthesized polynucleotides are often used as primers or adaptors for nucleic acid amplification, mutagenesis, and cloning.

Techniques also are being developed for de novo nucleic acid assembly whereby nucleic acids are made (e.g., chemically synthesized) and assembled to produce longer target nucleic acids of interest. For example, different multiplex assembly techniques are being developed for assembling oligonucleotides into larger synthetic nucleic acids that can be used in research, industry, agriculture, and/or medicine.

SUMMARY OF THE INVENTION

Aspects of the invention relate to methods, compositions, and devices for assembling nucleic acids. The invention provides nucleic acid configurations and cloning strategies for progressively assembling a long nucleic acid product using a plurality of assembly cycles. Aspects of the invention can reduce the time required for nucleic acid assembly by providing an efficient iterative assembly procedure for generating long nucleic acid products. In certain embodiments, an assembly cycle involves assembling a vector and two or more nucleic acid inserts containing one or more regulatory sequences. According to the invention, the regulatory sequence(s) activate one or more vector-encoded traits when they are assembled in a predetermined configuration. This allows a correctly assembled nucleic acid to be isolated by selecting or screening for the activated trait(s). The isolated nucleic acid may contain an assembled insert that can be excised along with one or more of the regulatory sequences and combined with a further nucleic acid insert and an appropriate vector in a subsequent assembly cycle. In this subsequent cycle, a correctly assembled product can again be isolated using one or more traits that are encoded by the vector and activated by the regulatory sequence(s) present on correctly ligated insert(s). This procedure can be repeated until a final nucleic acid product of interest is assembled. This final product can be used directly or further cloned (e.g., into a new vector) using any suitable technique. In some embodiments, one or more regulatory sequences used during assembly may be removed from the final nucleic acid product.

In some embodiments, correctly assembled nucleic acids can be isolated directly from a pool of transformed host cells in each cycle without requiring individual clones to be isolated and analyzed. This reduces the assembly time associated with each cycle by directly expanding a transformation mix in culture and bypassing the isolation and expansion of individual host cell colonies grown from a transformation mix. In some embodiments, an excised insert from a first vector may be combined with a second vector without separating (e.g., size selecting) the excised insert from the first vector backbone or from uncut vector/insert. Indeed, a restriction digest of a first assembled nucleic acid product may be combined directly with a second vector and another nucleic acid fragment. The restriction digest may include excised insert, empty vector backbone, and uncut vector/insert from the first assembly cycle. While the presence of the first vector backbone may interfere with the second ligation, correctly-ligated product can be selected for if the activated traits encoded by the second vector are different from those encoded by the first vector. This also may reduce assembly time by avoiding labor intensive size selection and isolation steps in each cycle.

Accordingly, aspects of the invention provide assembly techniques that are i) less error-prone than simultaneous ligations of pluralities of pooled DNA fragments, and ii) less labor-intensive than iterative pairwise ligation of DNA segments separated based on size. A simultaneous ligation of a plurality of pooled DNA fragments may generate mis-ligated products that typically are not identified until a subsequent sequence analysis performed on nucleic acid retrieved from a transformed cell culture. In contrast, methods of the present invention may select for correctly ligated products by selecting for activation of one or more vector-encoded traits. Iterative pairwise ligation of DNA segments separated based on size may be slow and labor intensive, because it involves DNA isolation and transformant analysis in each cycle of ligation. In contrast, methods of the present invention may be implemented without isolating fragments based on size and without analyzing individual clones from a transformation reaction to identify those with correctly ligated inserts. However, it should be appreciated that a size analysis may be performed as a quality control step either in parallel (e.g., to monitor the progress of the assembly reaction) or prior to performing the next assembly step (e.g., to confirm that a first assembly was successful prior to proceeding with a second assembly.

Aspects of the invention can be used in combination with one or more multiplex nucleic acid assembly techniques in order to assemble a long nucleic acid product from small starting nucleic acids (e.g., from a plurality of oligonucleotides). One or more of the nucleic acid inserts that are used in any of the vector activation assembly cycles described herein may be a nucleic acid that was previously assembled in a multiplex assembly reaction. For example, nucleic acid fragments generated using any of the multiplex assembly reactions illustrated in FIGS. 1-4 or otherwise described herein may be subsequently assembled to form larger nucleic acid products using one or more cycles of a vector-encoded trait activation technique. Accordingly, one or more vector activation assembly cycles may be included in an assembly procedure outlined in FIG. 5. Non-limiting examples of nucleic acid configurations that may be used for assembly by vector activation are illustrated in FIGS. 6-8, and further described herein. In some embodiments, a plurality of assembly cycles can be performed in parallel and pairs of nucleic acid products from a first set of assembly cycles can be combined and assembled in a second set of assembly cycles. In turn, pairs of assembled nucleic acids from the second set of assembly cycles can be combined and assembled in a third set of assembly cycles. This process can be repeated one or more times until a final product is assembled to contain all of the starting nucleic acids from the first plurality of assembly cycles. It should be appreciated that in some embodiments an assembly procedure is hierarchical in that it involves a plurality of converging iterative assembly reactions wherein a first plurality (e.g., N) of pair-wise assembly reactions produces a first plurality of products that are combined in a pair-wise fashion in a second plurality (e.g., N/2) of assembly reactions to generate a second plurality of products. This procedure can be repeated with the number of assembly reactions (and resulting assembly products) being twofold less at each consecutive stage (e.g., until a single final product is generated). In some embodiments, the sizes of the nucleic acid products at each stage are about twofold greater than the sizes at the prior stage (assuming that the initial nucleic acid inserts had similar sizes). Accordingly, this hierarchical assembly procedure can produce a long insert that increases exponentially in size as a function of the number of consecutive assembly steps. However, it also should be appreciated that iterative assembly procedures can be used in a linear assembly procedure. For example, at each consecutive step one product of a prior assembly may be combined with a second nucleic acid insert that was not generated from a prior iterative assembly procedure. In some embodiments, the second nucleic acid insert at each step may be a oligonucleotide (e.g., a double-stranded pair of oligonucleotides) or a relatively short nucleic acid assembled in a multiplex assembly reaction (e.g., about 500 nucleotides long). Accordingly, the nucleic acid being assembled in this linear procedure grows linearly by the length of the second nucleic acid added at each consecutive step. It should be appreciated that an iterative assembly of the invention may involve a combination of one or more linear and one or more exponential assembly steps and is not limited to either a hierarchical assembly or a linear assembly.

Design and assembly methods of the invention may be automated. Methods of the invention may reduce the cost and increase the speed and accuracy of nucleic acid assembly procedures, particularly automated assembly procedures.

Accordingly, aspects of the invention provide methods and compositions that can be used to efficiently assemble a target nucleic acid, particularly a long target nucleic acid. In some embodiments, a target nucleic acid may be amplified, sequenced or cloned after it is made. In some embodiments, a host cell may be transformed with the assembled target nucleic acid. The target nucleic acid may be integrated into the genome of the host cell. In some embodiments, the target nucleic acid may encode a polypeptide. The polypeptide may be expressed (e.g., under the control of an inducible promoter). The polypeptide may be isolated or purified. A cell transformed with an assembled nucleic acid may be stored, shipped, and/or propagated (e.g., grown in culture).

In another aspect, the invention provides methods of obtaining target nucleic acids by sending sequence information and delivery information to a remote site. The sequence may be analyzed at the remote site. The starting nucleic acids may be designed and/or produced at the remote site using one or more methods of the invention. In some embodiments, the starting nucleic acids, an intermediate product in the assembly reaction, and/or the assembled target nucleic acid may be shipped to the delivery address that was provided.

Other aspects of the invention provide systems for designing starting nucleic acids and/or for assembling the starting nucleic acids to make a target nucleic. Other aspects of the invention relate to methods and devices for automating a multiplex oligonucleotide assembly reaction that include one or more assembly methods of the invention. Yet further aspects of the invention relate to business methods of marketing one or more methods, systems, and/or automated procedures that involve assembly methods of the invention.

Other features and advantages of the invention will be apparent from the following detailed description, and from the claims. The claims provided below are hereby incorporated into this section by reference.

BRIEF DESCRIPTION OF THE FIGURES

FIG. 3 illustrates an embodiment of a ligase-based multiplex oligonucleotide assembly reaction;

FIG. 4 illustrates several embodiments of ligase-based multiplex oligonucleotide assembly reactions on supports;

DETAILED DESCRIPTION OF THE INVENTION

Figure 1A:
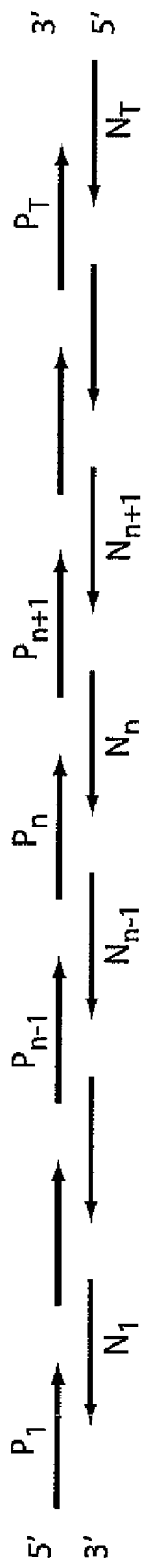
FIG. 1 illustrates certain aspects of an embodiment of a polymerase-based multiplex oligonucleotide assembly reaction.
Figure 1B:
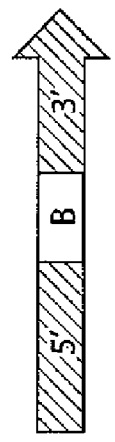

Aspects of the invention relate to iterative methods for assembling nucleic acid molecules. The invention provides methods and nucleic acid configurations for activating one or more vector-encoded traits (e.g., antibiotic resistance, auxotrophy, etc.) upon correct assembly of two or more nucleic acid fragments into a vector. Each nucleic acid fragment to be included in an assembly reaction may contain one or more activation sequences. These activation sequences are configured to activate vector-encoded trait(s) on a first vector only if the fragments are assembled in the correct order and orientation in the first vector. Accordingly, a nucleic acid insert that is correctly assembled in the first vector can be isolated by selecting or screening for appropriate trait activation (e.g., in a transformed host cell population). Once isolated, the correctly assembled nucleic acid insert can be removed from the first vector along with one or more activation sequences. This assembled nucleic acid insert then can be combined in a second assembly reaction with a further nucleic acid fragment that also may have one or more activation sequences. These fragments may be inserted into a second vector encoding one or more traits that are activated only if the fragments in the second assembly reaction are correctly assembled into the second vector. The second vector may have the same vector backbone as the first vector. The second vector may be a different vector that encodes one or more of the same traits as the first vector. However, in some embodiments, the second vector may encode one or more traits (e.g., traits that are activated when the correct activating sequence is introduced) that are different from the traits encoded by the first vector. In some embodiments, the second vector does not encode any of the activated trait(s) of the first vector. Similarly, the first vector may not encode any of the activated traits of the first vector. Accordingly, a correctly assembled insert in the second vector may be isolated by selecting or screening for appropriate trait(s) (e.g., in a transformed host cell population). This process may be repeated in one or more additional cycles (e.g., 2, 3, 4, 5, 6, 7, 8, 9, 10, etc.) adding at least one additional fragment in each cycle. After each cycle, the insert should be larger than the insert that was generated in the previous cycle. For example, a 100 kb fragment of DNA broken into one hundred 1 kb pieces will require 7 assembly steps (100>64>32>16>8>4>2>1) while the same fragment broken into two hundred 500 bp pieces will require 8 assembly steps (200>128>64>32>16>8>4>2>1). It should be noted that in the first assembly cycle, a subset of pieces may be paired such that the product of this pairing combined with the remaining pieces will yield a total number of pieces for the second round that is a power of two (e.g., 100=72+28; 72/2+28=64).

It should be appreciated that the nucleic acids that are combined for assembly in each cycle may be obtained from any suitable source. For example, each nucleic acid fragment independently may have been generated in a multiplex nucleic acid assembly reaction, an amplification reaction, a prior cloning procedure, etc., or any combination thereof. In some embodiments, one or two fragments that are combined for assembly each may have been generated in a prior assembly cycle that involved vector-encoded trait activation as described herein. In certain embodiments, a plurality of parallel assembly cycles involving vector-encoded trait activation may merge according to a predetermined hierarchy to generate a final assembled nucleic acid product in a hierarchical assembly procedure. Aspects of the invention may be used to generate a nucleic acid of any size. The size of the final product will depend, at least in part, on the size of the fragments that are being assembled and the number of assembly cycles that are performed. For example, nucleic acids from about 20 bp to about 1 mb long may be assembled. In some embodiments, a target nucleic acid may between about 100 bp and 1 kb (e.g., about 200 bp, about 300 bp, about 400 bp, about 500 bp, about 600 bp, etc.). In some embodiments, a target nucleic acid may between about 1 kb and 10 kb (e.g., about 2 kb, about 3 kb, about 4 kb, about 5 kb, about 6 kb, etc.), between about 10 kb and 100 kb (e.g., about 20 kb, about 30 kb, about 40 kb, about 50 kb, etc.), or between about 100 kb and 1 mb in size. However, target nucleic acids that are smaller, larger, or intermediate in size also may be assembled according to methods of the invention.

Aspects of the invention may be automated. For example, a robotic liquid handling device integrated with a plurality of reaction stations may be used to automate one or more cycles of assembly described herein. In some embodiments, one or more reaction steps may be performed (and optionally automated) on a microfluidic device comprising a microfluidic substrate having one or more reaction sites connected via microfluidic channels.

Aspects of the invention also provide vectors, nucleic acid cassettes (e.g., encoding one or more traits or comprising one or more activation sequences), enzymes, selection agents (e.g., one or more antibiotics), etc., that may be used as standard templates or reagents for assembly methods of the invention. One or more of these nucleic acids and/or reagents may be packaged in a kit. A kit also may comprise instructions for performing one or more assembly cycles involving activation of a vector-encoded trait.

These and other aspects of the invention are described in more detail in the following paragraphs.

Aspects of the invention relate to methods, compositions, and devices for assembling nucleic acids. Some aspects of the invention provide efficient methods for assembling nucleic acids using one or more assembly cycles, wherein at least two predetermined nucleic acids are assembled together with a vector in each assembly cycle. In each cycle, a correctly assembled nucleic acid product may be isolated using one or more appropriate traits (e.g., selectable and/or detectable traits), which become activated (e.g., functional) upon correct assembly of nucleic acid fragments. In some embodiments, one or more predetermined traits encoded on a vector may be activated in each cycle by the correct insertion of assembly nucleic acids into the vector. This may be accomplished by designing an insert fragment carrying one or more segments of nucleic acid (i.e., sequence) which function as "activation tags." Thus, according to the invention, selection and/or detection of a trait is at least in part based on activating otherwise non-functional marker carried on a fragment (such as vector) by activation tags that are provided by correct assembly of another fragment (such as an insert). Accordingly, aspects of the invention provide methods for specifically selecting correctly assembled nucleic acids rather than just the presence of certain traits. This can be used in each cycle to avoid certain cloning or validation steps and thereby reduce the time of each cycle. It should be appreciated that in each cycle, one or more nucleic acids being added to the assembly reaction may have been produced in a prior assembly cycle of the invention. Accordingly, iterative assembly using a plurality of assembly cycles can be used to generate progressively longer assembled nucleic acid products in a series of efficient assembly reactions.

Thus, some embodiments of the invention provide methods for assembling nucleic acid segments which include the following steps: digesting a first population of nucleic acids having at least first, second, third and fourth restriction sites, using a first set of restriction enzymes that cleave the nucleic acids at the first and third sites; digesting a second population of nucleic acids having at least first, second, third and fourth restriction sites, using a second set of restriction enzymes that cleave the nucleic acids at the second and fourth sites, where the first and second populations of nucleic acids comprise a first activation sequence located between the first and second restriction sites and a second activation sequence located between the third and fourth restriction sites, and digestion of the first population results in a first population of nucleic acid segments that comprises the first activation sequence but lacks the second activation sequence, and digestion of the second population results in a second population of nucleic acid segments that lacks the first activation sequence and comprises the second activation sequence; combining (optionally in the presence of a ligase) the first and second populations of nucleic acid segments with a first nucleic acid vector that is digested with one or more enzymes to generate overhangs that are compatible with the overhangs generated at the first and fourth sites (e.g., the vectors may be digested with restriction enzymes that cleave at the first and fourth restriction sites—however, any other enzymes that produce compatible overhangs may be used), wherein the first nucleic acid vector comprises a coding sequence of a first marker gene 5' of the first restriction site and a coding sequence of a second marker gene 3' of the fourth restriction site; and finally isolating ligated first nucleic acid vectors that express the first and the second marker genes, where expression of the first and the second marker genes is indicative of correct assembly of the first and second populations of nucleic acid segments. It should be appreciated that in any of the embodiments described herein wherein one or more vectors are digested with enzymes that cut at the first and fourth restriction sites (or equivalents thereof) may be practiced using a vector that is digested with one or more other enzymes that generate overhangs that are compatible with the overhangs at the first and fourth sites of the inserts being cloned into the vectors. Accordingly, the vector may not contain the first and fourth restriction sites provided it contains sites that can be specifically cut to produce appropriate compatible ends (e.g., overhangs) to clone the regulatory ends of the inserts adjacent to the regulatable markers (e.g., activatable markers) on the vector backbone.

In some embodiments, the methods may include additional steps: digesting a third population of nucleic acids having at least first, second, third and fourth restriction sites, using a first set of restriction enzymes that cleave the nucleic acids at the first and third sites; digesting a fourth population of nucleic acids having at least first, second, third and fourth restriction sites, using a second set of restriction enzymes that cleave the nucleic acids at the second and fourth sites, where the third and fourth populations of nucleic acids comprise a first activation sequence located between the first and second restriction sites and a second activation sequence located between the third and fourth restriction sites, and digestion of the third population results in a third population of nucleic acid segments that comprises the first activation sequence but lacks the second activation sequence, and digestion of the fourth population results in a fourth population of nucleic acid segments that lacks a first activation sequence and comprises a second activation sequence; combining in the presence of a ligase the third and fourth populations of nucleic acid segments with a second nucleic acid vector that is digested with restriction enzymes that cleave at the first and fourth restriction sites, wherein the second nucleic acid vector comprises a coding sequence of a first marker gene 5' of the first restriction site and a coding sequence of a second marker gene 3' of the fourth restriction site; selecting for ligated second nucleic acid vectors that express the first and the second marker genes, wherein expression of the first and the second marker genes is indicative of correct assembly of the third and fourth populations of nucleic acid segments; digesting the ligated second nucleic acid vector with restriction enzymes that cleave at the second and fourth restriction sites to release a fifth population of nucleic acid segments lacking a first activation sequence and comprising a second activation sequence; digesting the ligated first nucleic acid vector with restriction enzymes that cleave at the first and third restriction sites to release a sixth population of nucleic acid segments comprising a first activation sequence and lacking a second activation sequence, and combining in the presence of a ligase the fifth and sixth populations of nucleic acid segments with a third nucleic acid vector digested with restriction enzymes that cleave at the first and fourth restriction sites and having a third marker gene coding sequence 5' of the first restriction site and a fourth marker gene coding sequence 3' of the fourth restriction site; and selecting for ligated third nucleic acid vectors that express the third and fourth marker genes, where expression of the third and fourth marker genes is indicative of correct assembly of the fifth and sixth populations of nucleic acid segments.

In yet further embodiments, yet additional steps may be included for assembly: digesting a third population of nucleic acids having at least first, second, third and fourth restriction sites, using a first set of restriction enzymes that cleave the nucleic acids at the first and third sites; digesting a fourth population of nucleic acids having at least first, second, third and fourth restriction sites, using a second set of restriction enzymes that cleave the nucleic acids at the second and fourth sites, wherein the third and fourth populations of nucleic acids comprise a 5' promoter sequence located between the first and second restriction sites and a 3' promoter sequence between the third and fourth restriction sites, and digestion of the third population results in a third population of nucleic acid segments that comprises the 5' promoter sequence but lacks the 3' promoter sequence, and digestion of the fourth population results in a fourth population of nucleic acid segments that lacks a 5' promoter sequence and comprises a 3' promoter sequence; combining in the presence of a ligase the third and fourth populations of nucleic acid segments with a second nucleic acid vector that is digested with restriction enzymes that cleave at the first and fourth restriction sites, wherein the second nucleic acid vector comprises a coding sequence of a first marker gene 5' of the first restriction site and a coding sequence of a second marker gene 3' of the fourth restriction site; selecting for ligated second nucleic acid vectors that express the first and the second marker genes, wherein expression of the first and the second marker genes is indicative of correct assembly of the third and fourth populations of nucleic acid segments; digesting the ligated second nucleic acid vector with restriction enzymes that cleave at the second and fourth restriction sites to release a fifth population of nucleic acid segments lacking a 5' promoter sequence and comprising a 3' promoter sequence; digesting the ligated first nucleic acid vector with restriction enzymes that cleave at the first and third restriction sites to release a sixth population of nucleic acid segments comprising a 5' promoter sequence and lacking a 3' promoter sequence; and combining in the presence of a ligase the fifth and sixth populations of nucleic acid segments with a third nucleic acid vector digested with restriction enzymes that cleave at the first and fourth restriction sites and having a third marker gene coding sequence 5' of the first restriction site and a fourth marker gene coding sequence 3' of the fourth restriction site; and selecting for ligated third nucleic acid vectors that express the third and fourth marker genes, wherein expression of the third and fourth marker genes is indicative of correct assembly of the fifth and sixth populations of nucleic acid segments.

In further embodiments according to the invention, the methods for assembling nucleic acid segments may include the following steps: digesting a first population of nucleic acids having at least first, second, third and fourth restriction sites, using a first set of restriction enzymes that cleave the nucleic acids at the first and third sites; digesting a second population of nucleic acids having at least first, second, third and fourth restriction sites, using a second set of restriction enzymes that cleave the nucleic acids at the second and fourth sites, wherein the first and second populations of nucleic acids comprise a 5' promoter sequence located between the first and second restriction sites and a 3' promoter sequence located between the third and fourth restriction sites, and digestion of the first population results in a first population of nucleic acid segments that comprises the 5' promoter sequence but lacks the 3' promoter sequence, and digestion of the second population results in a second population of nucleic acid segments that lacks the 5' promoter sequence and comprises the 3' promoter sequence; combining in the presence of a ligase the first and second populations of nucleic acid segments with a first nucleic acid vector that is digested with restriction enzymes that cleave at the first and fourth restriction sites, wherein the first nucleic acid vector comprises a coding sequence of a first marker gene 5' of the first restriction site and a coding sequence of a second marker gene 3' of the fourth restriction site; and selecting for ligated first nucleic acid vectors that express the first and the second marker genes, wherein expression of the first and the second marker genes is indicative of correct assembly of the first and second populations of nucleic acid segments.

In any of the embodiments exemplified above, the first, second, third and/or forth marker genes may be selectable and/or activatable markers, such as antibiotic resistance genes. In addition, as discussed in more detail herein, the restriction enzymes used in any of the embodiments disclosed may be type II restriction enzymes or type IIS restriction enzymes. In some embodiments, the same first type IIS restriction enzyme recognition sequence is used for the first and third sites. Similarly, in some embodiments, the same type IIS restriction enzyme recognition sequence is used for the second and fourth sites. Accordingly, a single type IIS enzyme may be used to cut the first and third sites and a different single type IIS enzyme may be used to cut the second and fourth sites. It should be appreciated that in some embodiments, the type IIS recognition sites are located within the flanking regions of the inserts in association with the activating sequences. The second and third sites are oriented in such a way that the nucleic acid of the insert is cleaved by the respective enzymes binding to the recognition sites. In contrast, the first and fourth sites are oriented in such a way that the nucleic acid of the vector is cleaved by the respective enzymes. As a result, an insert released by cleavage at the first and third sites will have an overhang sequence at the first end that is complementary with an overhang generated on the second vector whereas the overhang sequence at the third site will be complementary to the overhang generated at the second site of a different insert release by cleavage at the second and fourth sites, wherein both inserts are designed to be assembled in a subsequent assembly step. Accordingly, it should be appreciated that that the inserts may be designed to include an overlapping sequence (e.g., at least the length of a restriction cleavage site such as a 4-base overlap of some type IIS restriction cleavage sites). Also, it should be appreciated that the cleavage overhang sizes and orientations generated by the restriction enzymes used for cutting the second and third sites should be compatible so that they generate complementary sequences for ligation within the overlap region of two inserts designed for subsequent ligation. These and other aspects of the vector and insert configurations are illustrated by the non-limiting examples provided herein.

In some embodiments, the type IIS recognition sites may be located within the promoter regions of the activation sequences (e.g., between or around the −35 and −10 sequences of a promoter) and located such that the digestion site is either outside the activation sequence within the insert sequence (e.g., for sites 2 and 3) or distal to the insert site and in the vector sequence (e.g., for sites 1 and 4). These and other aspects of the restriction site configurations are illustrated by the non-limiting examples provided herein.

It should be appreciated that in some embodiments described herein all sites 1, 2, 3, and 4 are recognized by the same enzyme (e.g., the same type IIS enzyme). In these embodiments, differential cutting at sites 1 and 3 versus 2 and 4 may be achieved using selective protection, methylation, and/or cleavage techniques as described herein. For example, a first set (e.g., pair) of oligonucleotides may be used to protect only sites 1 and 3 from methylation (e.g., using a RecA mediated triple helix formation). Subsequently, after removal of the protecting oligonucleotides, selective cleavage of the umethylated sites 1 and 3 may be obtained using an enzyme that is sensitive to the methylation of the substrate nucleic acid. Similarly, sites 2 and 4 may be selectively cleaved using specific oligonucleotides that protect sites 2 and 4 (but not sites 1 and 3).

Figure 11:
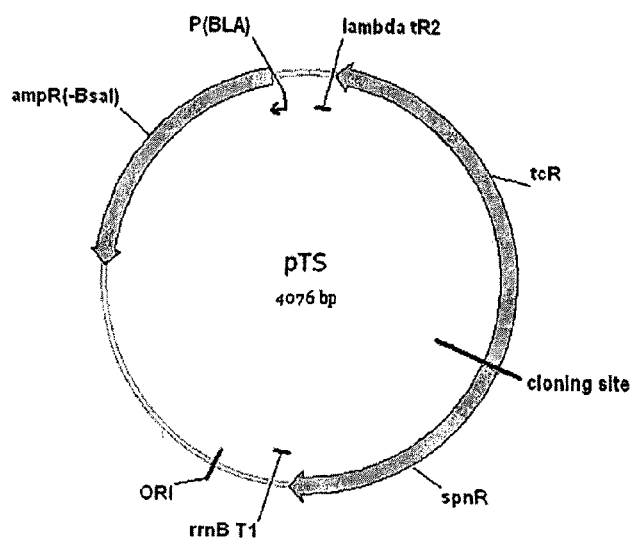
FIG. 11 provides non-limiting diagrams of exemplary vectors for Pairwise Selection Assembly (PSA); and, FIG. 12 illustrates a non-limiting example of promoter regions containing type IIS recognition sequences for use in some aspects of the invention.
Figure 11:
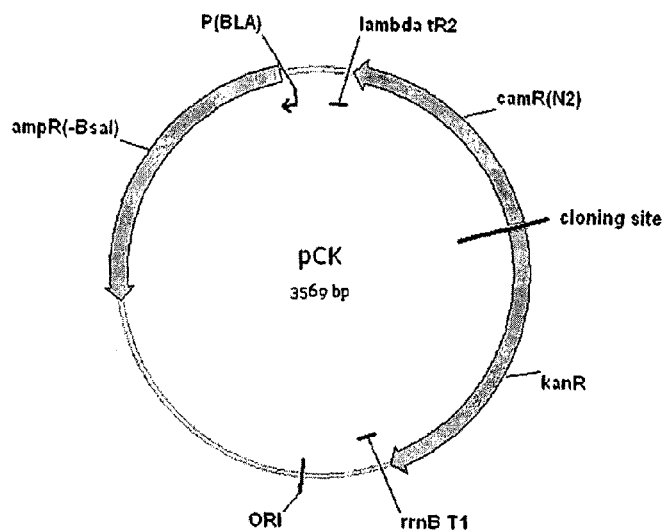

Aspects of the invention provide nucleic acid configurations and assembly strategies that involve selecting for one or more vector-encoded traits in a plurality of consecutive assembly cycles. In some embodiments, the same vector encoding the same trait(s) may be used in a plurality of consecutive assembly cycles, with one or more additional nucleic acids being added in each cycle. However, in some embodiments, two or more different vectors may be used in consecutive cycles. In some embodiments, two different vectors are used repeatedly in alternate cycles. For example, a first vector encoding one or more first traits (e.g., one, two, three, four, or more first traits) may be used in a first cycle, followed by a second vector encoding one or more second traits (e.g., one, two, three, four, or more second traits) in a second cycle. By using alternate assembly vectors having different selectable traits in consecutive cycles, background carryover from one cycle to the next (e.g., due to vectors that were not cut or vectors that were re-circularized without the insertion of an additional fragment) is reduced or avoided. In some embodiments, for example, a first vector may contain two selectable markers (e.g., traits), such as chloramphenicol and kanamycin, which become functional upon ligation with a correct insert. A non-limiting example of such a vector is pCK, as illustrated in FIG. 11. Similarly, a second vector may contain two selectable markers (e.g., traits), such as tetracycline and specintomycin, which become functional upon ligation with a correct insert. A non-limiting example of such a vector is pTS, as illustrated in FIG. 11. Thus, the invention includes methods of assembly using these vectors repeatedly in alternate cycles to generate progressively longer nucleic acid fragments.

Each of the vectors provided in the instant invention for use in the assembly process contain a functional selection marker, e.g., ampicillin resistance, which can be used for propagations purposes, in addition to two non-functional (e.g., activatable) resistance markers as described above. The vectors, such as pCK and pTS, may be constructed such that they contain either a high-copy number origin of replication, or a BAC-based single-copy number origin of replication. The former versions enable DNA assembly up to ~10-30 kb, while the latter BAC-based vectors may be more suitable for longer construction up to ~300 kb. Transition from one vector type to another is seamless, as both vector types have the same non-functional markers that are activated by the same activation tags (i.e., they differ only in the origin of replication).

Therefore, cloning may be done by transformation followed by growth and selection of the transformed cell population without isolating and analyzing individual colonies grown from the transformed cell population prior to subsequent expansion.

In some embodiments, predetermined nucleic acids and vectors may be designed to produce one or more selectable or detectable traits when a correct assembly reaction occurs. Accordingly, aspects of the invention may provide algorithms (e.g., computer-implemented algorithms) for designing nucleic acid configurations with appropriate selection or detection techniques that may be chosen to isolate correctly assembled nucleic acids in one or more consecutive assembly cycles. According to aspects of the invention, a nucleic acid that is correctly assembled from two smaller nucleic acids in a first assembly cycle may be used in a second assembly cycle. In the second cycle, correct assembly with yet a further nucleic acid and an appropriate vector may generate a longer assembled nucleic acid that can be isolated using appropriate selection or detection techniques. In some embodiments, the same selectable or detectable traits may be used in each assembly cycle. However, the invention is not limited in this respect and different traits may be used in each cycle. In some embodiments, strategies may be developed for alternating traits that are selected for in consecutive assembly cycles. This may reduce the frequency of nucleic acids that are carried over, from one assembly cycle to the next, without being assembled with an additional nucleic acid in each cycle.

In each assembly cycle, the correct insertion of at least one nucleic acid into a vector produces a selectable or detectable trait (e.g., by increasing or decreasing the expression of a marker encoded by the vector). In some embodiments, the insertion of each of two nucleic acids into the vector produces a selectable or detectable trait (e.g., by each nucleic acid increasing or decreasing the expression of a marker encoded by the vector). In certain embodiments, each nucleic acid inserted into the vector produces a different selectable or detectable trait (e.g., by increasing or decreasing the expression of a different marker encoded by the vector). However, it should be appreciated that each nucleic acid inserted into the vector may increase or decrease the expression of the same marker, resulting in different levels of the detectable or selectable trait depending on the number of nucleic acids that are inserted into the vector. Accordingly, in each assembly cycle, the targeted insertion of predetermined nucleic acids (e.g., two predetermined nucleic acids) into a vector may be selected for by selecting for appropriate combinations and/or levels of one or more vector-encoded traits. It should be appreciated that, in any assembly cycle, one or more (e.g., one or both) of the predetermined nucleic acids being assembled may have been assembled in a prior assembly cycle from one or more smaller nucleic acids (e.g., from the assembly of two smaller nucleic acids in a prior cycle).

For example, a segment of nucleic acid residing on a vector which on its own non-functional becomes functional (e.g., activated) only when combined (e.g., assembled) with a segment present on an insert (e.g., an activation tag). As discussed in more detail below, a number of such activation configurations are contemplated herein. In some circumstances, a non-functional segment of nucleic acid on a vector may be a promoter or a fragment thereof, which then becomes turned-on in the presence of a correctly assembled insert containing a remainder of sequences necessary to activate the marker. In this case, correct assembly of the vector and the insert induces transcription of a gene or a fragment thereof encoded by a nucleic acid segment following the promoter sequence. In some cases, a portion of a coding sequence may be provided on the insert (e.g., as part of an activation sequence). For example, a promoter may be associated with at least a start codon (ATG) in the activation sequence on the insert tag. In some embodiments, a coding region that can be used to activate one or more (e.g., 2, 3, 4, etc.) activatable markers may be included in the activation sequence on an insert. Such a coding region may be, for example, a signal peptide, a multimerization domain, a stabilization domain, etc., or any combination thereof. In other applications, a non-functional segment on a vector may represent a component or part of a functional unit, which must be supplemented by additional component (on an insert) to become functional. For instance, a vector may encode one subunit of a factor which by itself inactive, and an insert nucleic acid may encode another subunit, which together with the first subunit encoded by the vector can form a functional unit. Similarly, a vector may encode only a portion of a functional factor, and an inset may encode a remainder of the functional unit, such that only when the fragments are correctly assembled the factor becomes functional.

Figure 6:
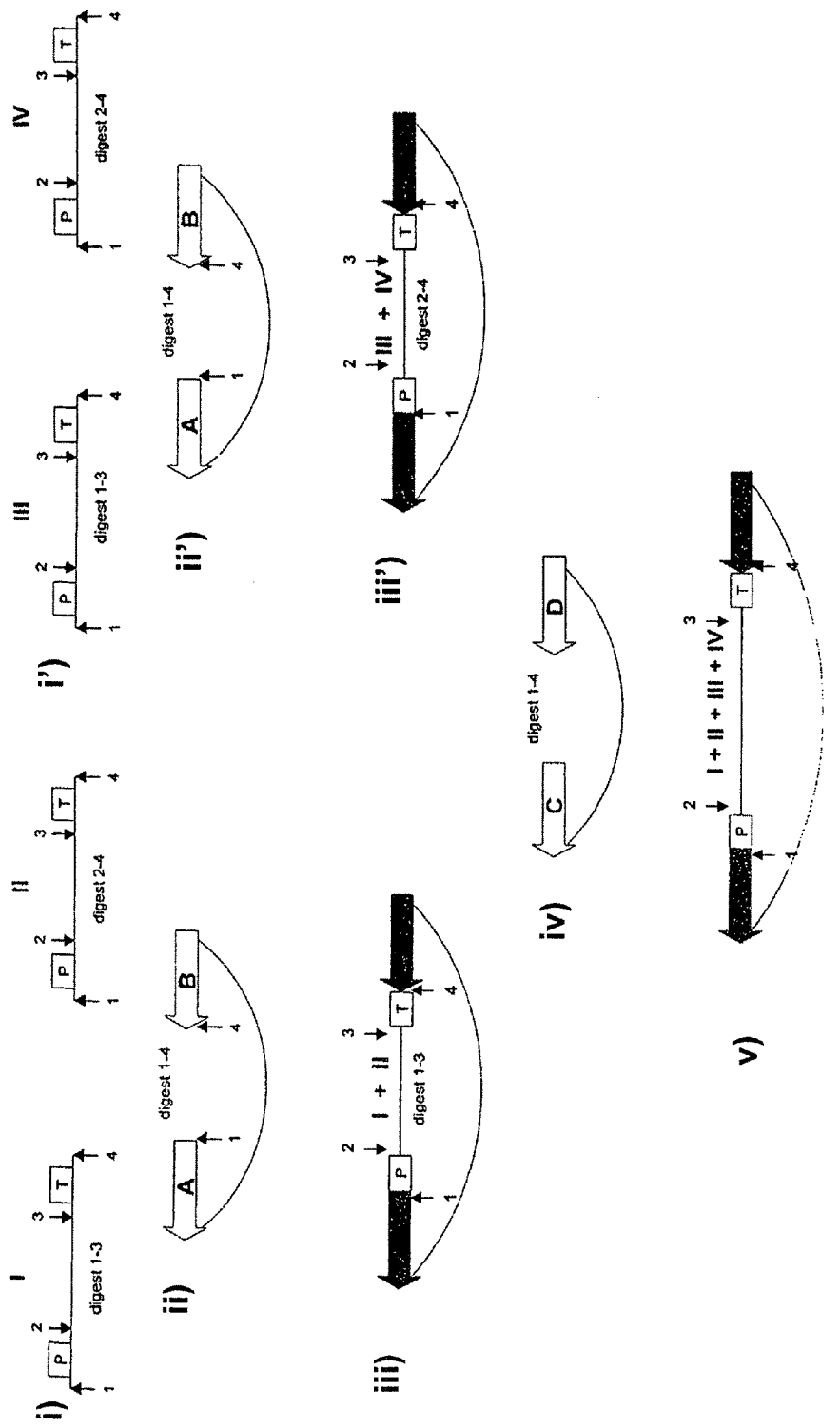
FIG. 6 illustrates a non-limiting embodiment of two assembly cycles of the invention.
Figure 7A:
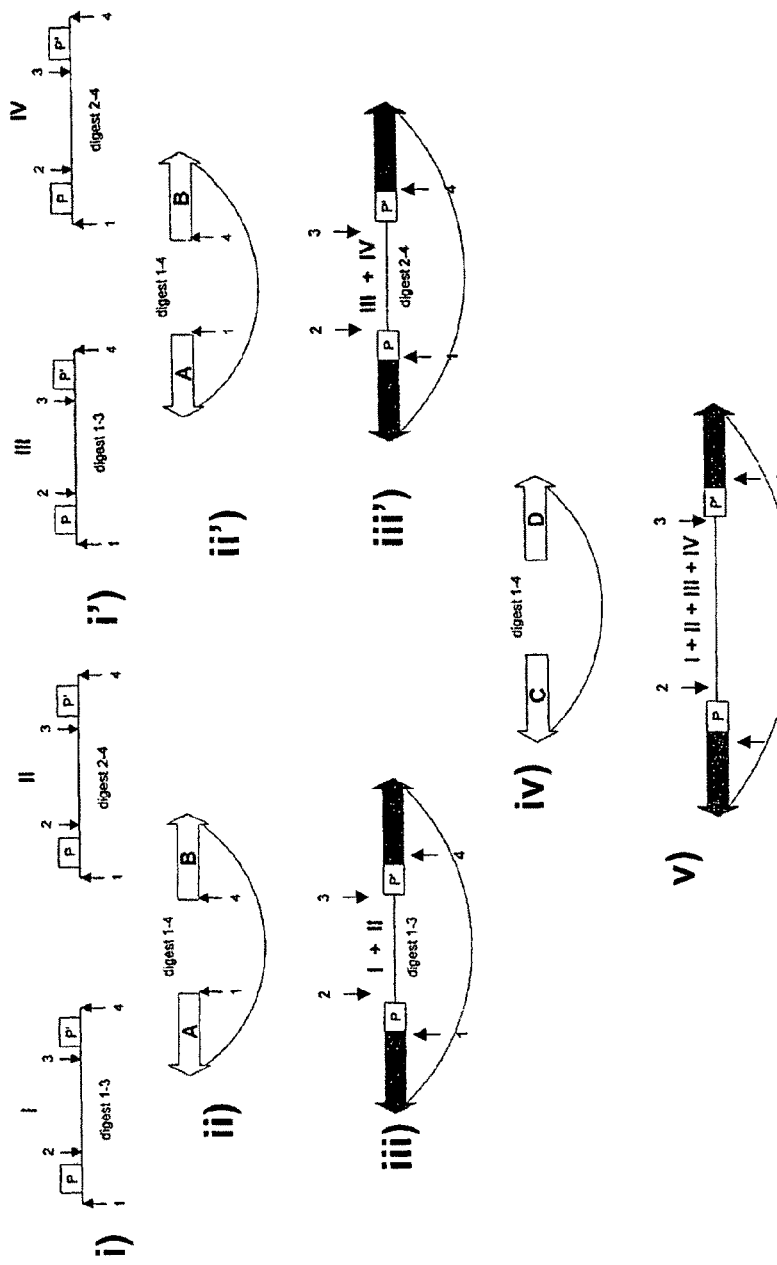
FIG. 7 illustrates a non-limiting embodiment of two assembly cycles of the invention.

FIGS. 6 and 7 illustrate non-limiting embodiments of two assembly cycles of the invention. In FIG. 6, the activation sequences are a promoter (P) and a terminator (T). In FIG. 7, the activation sequences are both promoters (P and P'). However, other combinations of promoters and terminators may be used as activation sequences (e.g., two terminators). Also, other types of activation sequences may be used. In certain embodiments, an activation sequence may be any suitable cis-acting sequence (e.g., a regulatory sequence such as a promoter, terminator, enhancer, ribosome binding or other cis-acting regulatory sequence—for example, a cis-acting protein binding sequence) that can regulate the expression levels of a marker gene (e.g., a gene that produces a selectable trait when it is either up-regulated or down-regulated). In some embodiments, an activation sequence may be any suitable trans-acting sequence (e.g., a sequence that encodes a regulatory peptide or other trans-acting regulatory factor) that can regulate the expression levels of a marker gene (e.g., a gene that produces a selectable trait when it is either up-regulated or down-regulated). It should be appreciated that the expression levels of a marker gene in a host cell may be up-regulated or down-regulated by an activation sequence. In some embodiments, a marker gene is not expressed in the absence of an activation sequence, and expressed in the presence of the activation sequence. However, the expression level of a marker gene may increase from a lower level to a higher level in the presence of the activation sequence. In certain embodiments, a marker gene is expressed in the absence of an activation sequence and silenced in the presence of the activation sequence. However, the expression level of a marker gene may decrease from a higher level to a lower level in the presence of the activation sequence. In some embodiments, activation sequences are short sequences (e.g., DNA sequences) necessary for the activation of non-functional marker genes (e.g., antibiotic resistance markers) present on the target vector. For example, an activation sequence may be a promoter, a terminator (e.g., a terminal amino-acid/stop-codon region necessary for expression of a marker gene), or other short sequence necessary for correct expression of a marker gene. In some embodiments, a regulatory sequence may be a silencer that reduces expression of a gene resulting in a selectable or detectable trait associated with the reduced gene expression.

A marker gene may be any gene that confers a detectable or selectable trait on a cell when its expression levels change (e.g., increase or decrease, depending on the marker gene). For example, an antibiotic resistance marker may confer a selectable trait (antibiotic resistance) when its expression level is up-regulated. Other marker genes may be auxotrophic markers, or other selectable or detectable markers. An example of a detectable marker is a fluorescent marker. Such markers are well known in the art.

In some embodiments, marker genes are fluorescent reporter genes (e.g., GFP, DsRed, YFP, CFP, etc). Inactive fluorescent reporters encoded on the target vector would be activated upon insertion of DNA molecule(s) containing activation sequences. After transformation and recovery, cells may be sorted via flow cytometry. Cells containing the expressed fluorescent reporter genes can be isolated. The isolated cells contain the correctly ligated DNA. In some embodiments, the activation and expression of a fluorescent reporter gene may be more rapid than the activation and expression of an antibiotic resistance marker. Accordingly, in some embodiments, the isolation of correct constructs using flow cytometry may be performed earlier (e.g., after a shorter cell recovery and growth time after transformation) than a selection involving activation of antibiotic resistance markers.

In FIG. 6, fragments I through IV are assembled in two cycles. In a first assembly cycle, fragments I and II of i) are assembled into vector of ii) to generate I+II of iii), and fragments III and IV of i') are assembled into vector of ii') to generate III+IV of iii'). In a second assembly cycle, fragments I+II of iii) and III+IV of iii') are assembled into vector of iv) to generate fragment I+II+III+IV of v). In i), fragments I and II are provided in constructs comprising two flanking activation sequences (P and T), wherein each activation sequence is flanked by two different restriction enzyme recognition sites (restriction sites 1 and 2 flank P, and restriction sites 3 and 4 flank T). It should be appreciated that one or both of these constructs may be provided in a first vector (e.g., a plasmid). However, in some embodiments, one or both of these constructs may be provided as a linear product of a multiplex nucleic acid assembly reaction. In some embodiments, the constructs may be amplified (e.g., by PCR or LCR). The construct containing I is digested with restriction enzymes that cut at 1 and 3 to generate a linear product that contains I and one of the flanking activation sequences (P). The construct containing II is digested with 2 and 4 to generate a product that contains II and the other flanking activation sequence (T). The digested constructs are combined with a vector ii) that contains restriction sites 1 and 4 adjacent to marker genes A and B, respectively. In ii), site 1 is 5' of marker gene A, and site 4 is 3' of marker gene B. A and B are inactive in ii). The vector of ii) is digested with restriction enzymes that recognize sites 1 and 4. The digested nucleic acids of i) and ii) are ligated to generate a product shown in iii). In a correct assembly, the free ends generated by digestion at site 1 flanking P and at site 1 upstream of A are compatible (e.g., cohesive), and activation sequence P is ligated upstream of marker A in the vector, thereby activating A. In a correct assembly, the free ends generated by digestion at site 4 flanking T and at site 4 downstream from B are compatible (e.g., cohesive), and activation sequence T is ligated downstream of marker B in the vector, thereby activating B. In a correct assembly, the free ends generated by restriction digestion at sites 3 and 2, flanking I and II respectively, are compatible (e.g., cohesive) and are ligated together to generate product I+II in a vector expressing A and B as shown in iii). The ligated nucleic acids of i) and ii) are transformed into a suitable host cell preparation. A correct assembly may be selected for by selecting for traits associated with activation of A and B in the host cells.

Similarly, in i') a construct containing III is digested with restriction enzymes that recognize sites 1 and 3, and a construct containing IV is digested with restriction enzymes that recognize sites 2 and 4. The restriction products of i') are ligated into a vector of ii') that has been digested with restriction enzymes recognizing 1 and 4. The resulting product III+IV is shown ligated into the vector in iii'). As described for I and II, the correct assembly, of III and IV may be isolated by selecting for traits associated with A and B in suitable host cells after transformation of the ligation reaction products.

In a second assembly cycle, I+II are assembled with III+IV to generate I+II+III+IV. The nucleic acids of iii) may be digested with restriction enzymes that recognize 1 and 3, generating a linear product that contains I+II and one of the flanking activation sequences (P). The nucleic acids of iii') may be digested with restriction enzymes that recognize 2 and 4, generating a product that contains III+IV and the other flanking activation sequence (T). The digested constructs are combined with a vector of iv) that has been digested with restriction enzymes recognizing sites 1 and 4 adjacent to inactive marker genes C and D, respectively. The nucleic acids are ligated and transformed into a suitable host cell preparation. A correct assembly of I+II+III+IV shown in v) may be selected for by selecting for traits associated with activation of C and D in the host cells.

Figure 7B:
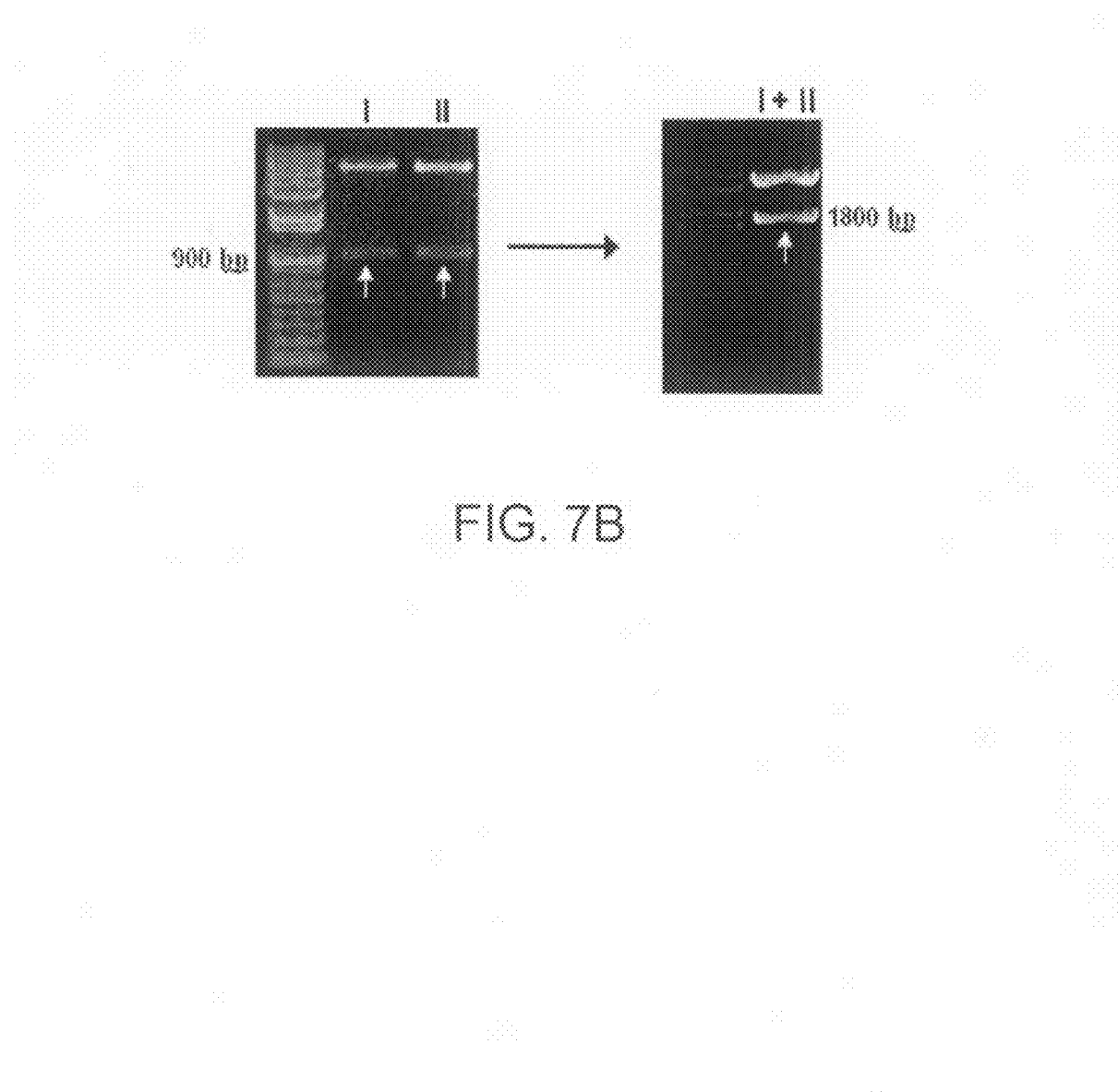

In FIG. 7, fragments I through IV are assembled in two cycles as described above for FIG. 6. However, the flanking activation sequences in FIG. 7 are both promoters (e.g., P and P'). Accordingly, the coding sequences of both sets of marker genes (A and B in ii) and ii'), and C and D in iv)) are oriented so that sites 1 and 4 are upstream of the marker genes. As a result, correct insertion of the promoter containing fragments into sites 1 and 4 activates both sets of marker genes. A working example of a first assembly cycle of this configuration is provided in FIG. 7B. Here, two approximately 900 bp fragments (I and II) are being combined to make a contiguous 1800 bp fragment. In this example, sites 1 and 3 are BsaI sites and sites 2 and 4 are BsmBI sites (see FIG. 7). These restriction sites are not present in the sequence being assembled. Restriction digestion reactions can be heat-inactivated and a portion of each digestion can be combined with linearized destination vector in a ligation reaction. *E. coli* cells can then be transformed with the ligation reaction and correct pairs can be selected in culture. As demonstrated in FIG. 7B, showing agarose gel electrophoresis of digested DNA before and after assembly and selection, two ~900 bp fragments can be assembled to generate a contiguous 1,800 bp fragment according to the methods of the present invention.

It should be appreciated that after each cycle, an assembled insert (e.g., I+II, III+IV, and I+II+III+IV) is flanked by activator sequences (e.g., P and T in FIG. 6, P and P' in FIG. 7, or any other combination of activator sequences). Also, the activator sequences retain flanking restriction sites 1, 2, 3, and 4 in the same configuration (e.g., as illustrated in FIGS. 6 and 7). Accordingly, the product of each assembly cycle can be used in a further assembly cycle using the same strategy. For example, product v) in FIGS. 6 and 7 can be processed as described herein (e.g., cut with 1 and 3, or with 2 and 4) and ligated into a suitable vector along with an additional fragment having the appropriate compatible free ends for ligation.

In some embodiments, a vector with different marker genes is used in each cycle. For example, vectors of ii) and iv) may be used in alternate cycles. Accordingly, an insert excised from v) may be cloned into a vector of ii) along with an additional fragment, and correctly assembled inserts may be selected for by selecting for activation of A and B. In the next cycle, a vector of iv) may be used, etc. By alternating vectors in consecutive cycles, the selection combination used in each cycle (e.g., for A and B or for C and D) specifically selects for the intended fragment assembly product and selects against the vector that was used in a prior assembly cycle. As a result, aspects of the invention may be readily automated. In some embodiments, ligation assembly reactions may be performed using restriction digest mixtures that contain the fragments to be assembled and also the vector backbones from the prior assembly. Selection for different markers (e.g., alternate markers) in each cycle reduces or prevents the vector backbones from a prior cycle from interfering with the assembly process (e.g., avoids a background of transformed cells containing vectors from a prior cycle from being amplified). Accordingly, size separation steps (e.g., to isolate a fragment from a vector) may be omitted from these assembly cycles.

It should be appreciated that restriction sites 1-4 and the corresponding restriction enzymes may be chosen from any suitable restriction site/enzyme combinations. However, certain enzyme selections and configurations may be particularly useful.

In some embodiments, restriction sites 1 and 4 are long recognition sites (e.g., between about 8 and about 50 nucleotides long) that are recognized by rare-cutting restriction enzymes. Rare-cutting restriction enzymes may be meganucleases, modified meganucleases (e.g., engineered meganucleases that include a cleavage domain from a type IIS enzyme but retain the binding domain of a meganuclease—for example from a mutant meganuclease that binds and does not cleave a target sequence, see for example meganucleases described in U.S. Ser. No. 60/925,507, filed Apr. 19, 2007, the disclosure of which is incorporated herein by reference), or other rare cutting enzymes (e.g., NotI). Restriction sites 1 and 4 may be Type II sites that are regenerated after ligation in each cycle.

Restriction sites 2 and 3 may be Type IIS sites that are not regenerated after ligation in each cycle. Sites 2 and 3 may be oriented to cause cleavage within the central region of each construct (as opposed to cleavage in the flanking regions). Restriction sites 2 and 3 may be different. However, the cleavage patterns (e.g., the type of overhang, 5' or 3', and the overhang length) of the Type IIS restriction enzymes that recognize 2 and 3 may be identical or similar. As a result, the nucleic acid constructs may be designed so that cleavage by Type IIS enzymes specific for sites 2 and 3 generates free ends that are compatible (e.g., cohesive or complementary) for a subsequent ligation reaction. For example, sites 2 and 3 may be located to cause Type IIS cleavage within a sequence region that is common to the fragments being assembled (e.g., in an overlapping sequence region of I and II, or of III and IV, or of II and III illustrated in FIGS. 6 and 7). In some embodiments, the common or overlapping regions are not duplicated after assembly, because the cleavage sites may be designed to cut at a location that results in a single copy of the overlapping or common regions being reassembled upon ligation. It should be appreciated that, in this non-limiting configuration, the cleavage sites for 2 and 3 are within the sequence of the nucleic acid being assembled. In contrast, the recognition sites for 2 and 3 are outside the sequence of the nucleic acid being assembled. Therefore, these recognition sites are not regenerated upon ligation (e.g., of I and II, III and IV, or II and III). However, in each cycle, additional sites 2 and 3 that are at the opposite ends of the fragments (e.g., at the ends cut at 1 and 4, respectively) are carried over into the newly assembled product and are available for cleavage in a subsequent cycle as illustrated in FIGS. 6 and 7.

In some circumstances, the invention may be useful for generating a library of variants. For example, each insert to be progressively added (e.g., insert I, II, III, and IV as shown in FIGS. 6 and 7) may represent a plurality of nucleic acid variants. For example, insert I may represent a plurality (e.g., a pool) of variants of I, and insert II may represent a plurality (e.g., a pool) of variants of II, and so on. Such variants may include naturally occurring variants (such as SNPs) and other mutations. In some embodiments, each insert may encode a module of a protein (polypeptide), each containing one or more variants. In some cases, the protein is a naturally occurring protein or variant thereof. Such variants may represent functional variants, structural variants, sequence variants, etc. In some circumstances, the protein is an engineered protein (i.e., artificial protein) comprising one or more modules. In some embodiments, a module may represent a functional module, e.g., a kinase domain, etc. In further embodiments, each insert may represent a gene element, such as regulatory regions (e.g., promoters), exons, untranslated regions (e.g., 5'-UTR and 3'-UTR etc.). Thus, the invention contemplates that in some embodiments insert I may represent a library of promoters, insert II may represent a library of genes or fragments thereof having similar functions (such as a functional domain), and insert III may represent a further fragment, and so on. In yet further embodiments, each insert may represent a cluster of genes or gene elements. Thus, the methods and compositions of the instant invention may be used to generate a library of plurality of nucleic acid variants. In particular, the method of the invention may be useful for generating a library of variants, each of which is a relatively long nucleic acid, e.g., 1, 5, 10, 15, 20, 30, 40, 50 kb or more.

In some embodiments, restriction enzyme digestion and ligation may be performed in the same reaction tube. The use of Type IIS sites that are not regenerated after ligation can drive the reaction towards the correct assembly as described in more detail herein. This also may speed up an assembly reaction by avoiding separate digestion and ligation steps and by avoiding any purification, size separation, or other processing steps in between restriction enzyme digestion and ligation. This aspect also may be readily automated, avoiding additional sample manipulations associated with separate restriction digestion and ligation steps.

It should be appreciated that in some embodiments, sites 1 and 3 may be cut by the same restriction enzyme (e.g., oriented such that site 1 is retained and site 3 is not retained after the subsequent ligation reaction). Similarly, sites 2 and 4 may be cut by the same restriction enzyme (e.g., oriented such that site 4 is retained and site 2 is not retained after the subsequent ligation reaction). It also should be appreciated that sites 1, 2, 3, and 4 all may be recognized by different enzymes. However, in some embodiments, sites 1, 2, 3, and 4 may be recognized by the same enzyme (e.g., the sites all have the same sequence) and differential digestion at positions 1 and 3 versus 2 and 4 may be achieved using specific protection or digestion techniques described herein (e.g., using oligonucleotides to protect from methylation).

It should be appreciated that the presence, within the sequence of an insert, of one or more of the recognition sites for an enzyme used for iterative assembly (e.g., a restriction enzyme that cleaves at site 1, 2, 3, and/or 4) may complicate the assembly process by resulting in cleavage at unwanted positions. Accordingly, in some embodiments, a target sequence for assembly may be designed so that it does not include such sites. However, in some embodiments, specific recognition and cleavage at sites 1, 2, 3, and 4 illustrated in FIGS. 6 and 7, without unwanted cutting at any identical sites 1, 2, 3, and 4 within the fragments being assembled, may be achieved using different strategies described herein in more detail (e.g., using rare-cutting enzymes, masking unwanted cleavage sites, methylating unwanted cleavage or recognition sites while masking targeted cleavage or recognition sites to protect them from methylation, etc.). In some embodiments, specific digestion at one or more of locations 1, 2, 3, and 4, may be achieved using targeted nuclease digestion (e.g., using targeted triple helix formation as described in more detail herein).

Figure 8:
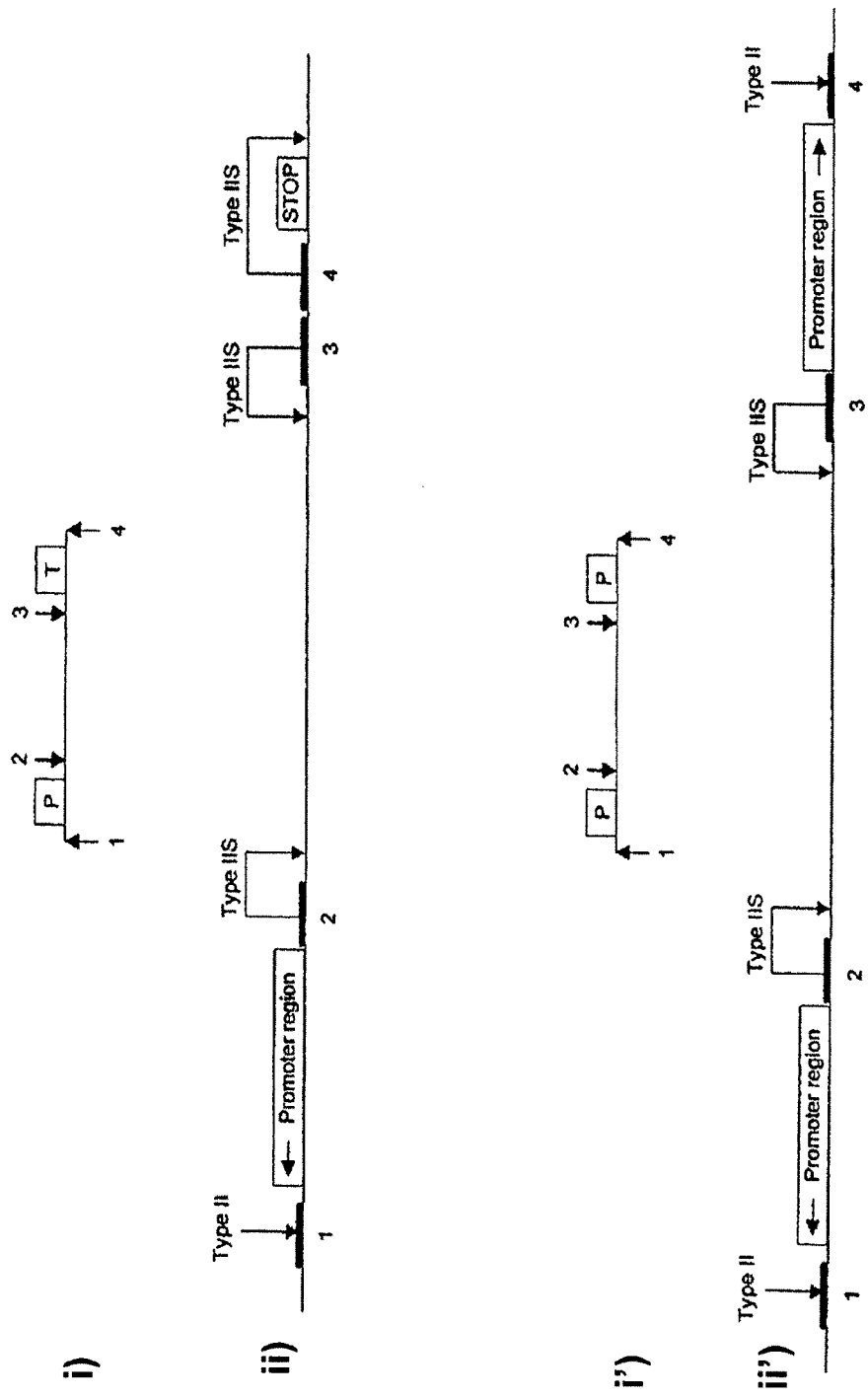
FIG. 8 illustrates non-limiting embodiments of activator sequence configurations according to the invention.

FIG. 8 illustrates non-limiting embodiments showing details of activator sequence configurations such as those in FIGS. 6 and 7. It should be appreciated that the assembly strategy and configurations of sites, activation sequences, and markers illustrated in FIGS. 6, 7, and 8 may be generalized and used for any suitable combination of enzymes, enzyme recognition sites, activation sequences, marker genes, etc. as described herein.

In some embodiments, activatable auxotrophic markers may include one or more of the following non-limiting examples of yeast alleles that may be used as auxotrophic markers: ade1-14, ade2-1, ade2-101, ade2-BglII, can1-100, his3delta200, his3delta1, his3-11,15, leu2delta1, leu2-3,112, lys2-801, lys2delta202, trp1delta1, trp1delta63, trp1-1, trp1-289, ura3-52, ura3-1, ade2delta::hisG, leu2delta0, lys2delta0, met15delta0, ura3delta0. Additional auxotrophic markers and other markers that may be used are known in the art (See, for example, Brachmann et al. (1998) "Designer deletion strains derived from *Saccharomyces cerevisiae* S288C: a useful set of strains and plasmids for PCR-mediated gene disruption and other applications." *Yeast* Volume 14, pp 115-132)

In some embodiments, activatable markers may confer resistance to one or more of the following non-limiting antibiotics: neomycin, ampicillin, hygromycin, gentamycin, bleomycin, phleomycin, kanamycin, geneticin (or G418), paromomycin, tetracycline, beta-lactams, vancomycin, erythromycin, chloramphenicol, novobiocin, cefotaxime, coumermycin $A_1$ and spectinomycin.

In some embodiments, one or more of the following non-limiting list of promoters may be used as activation sequences: bacterial promoters (e.g., T7, tRNA, mm promoters, etc.); yeast promoters (e.g., GAL1, GAL10, ADH1, etc.); insect promoters; mammalian promoters; and/or promoters from other species. In some embodiments, a natural promoter sequence may be modified to incorporate one or more restriction sites (e.g, type IIS restriction sites).

It should be appreciated that the same activation sequence may be used at both ends of an insert. For example, the same promoter may be used at the left and right ends of the assembled inserts described herein. However, the orientation of the activation sequences (e.g., promoters) may be such that they only work when integrated (e.g., ligated) into the correct site. For example, the promoters may be on opposite strands relative to the insert and only work to activate the adjacent marker if cloned into the correct end of the vector.

It should be appreciated that any suitable vector may be used as described herein. For example a vector may have an origin of replication, a selectable marker (e.g., an active marker) different from the activatable markers (e.g., inactive markers) used for assembly as described herein. The vector also may include appropriate restriction sites adjacent to the activatable markers as described herein. The vectors may be prokaryotic, eukaryotic (e.g., yeast, mammalian, insect) or viral. Different vectors may be adapted for different insert sizes as described herein (e.g., BAC, YAC, etc. for larger insert sizes) or different uses. However, different vectors may include the same activatable markers and/or appropriate restrictions sites for iterative assembly as described herein.

It should be appreciated that any suitable technique (e.g., chemical or enzymatic) may be used to digest the nucleic acids at the appropriate sites as described herein for iterative assembly. Similarly, any suitable technique may be used for connecting nucleic acids (e.g., chemical or enzymatic ligation—e.g., using a suitable ligase such as T4 ligase or other ligase, or in vivo recombination as described herein for concerted assembly).

Figure 5:
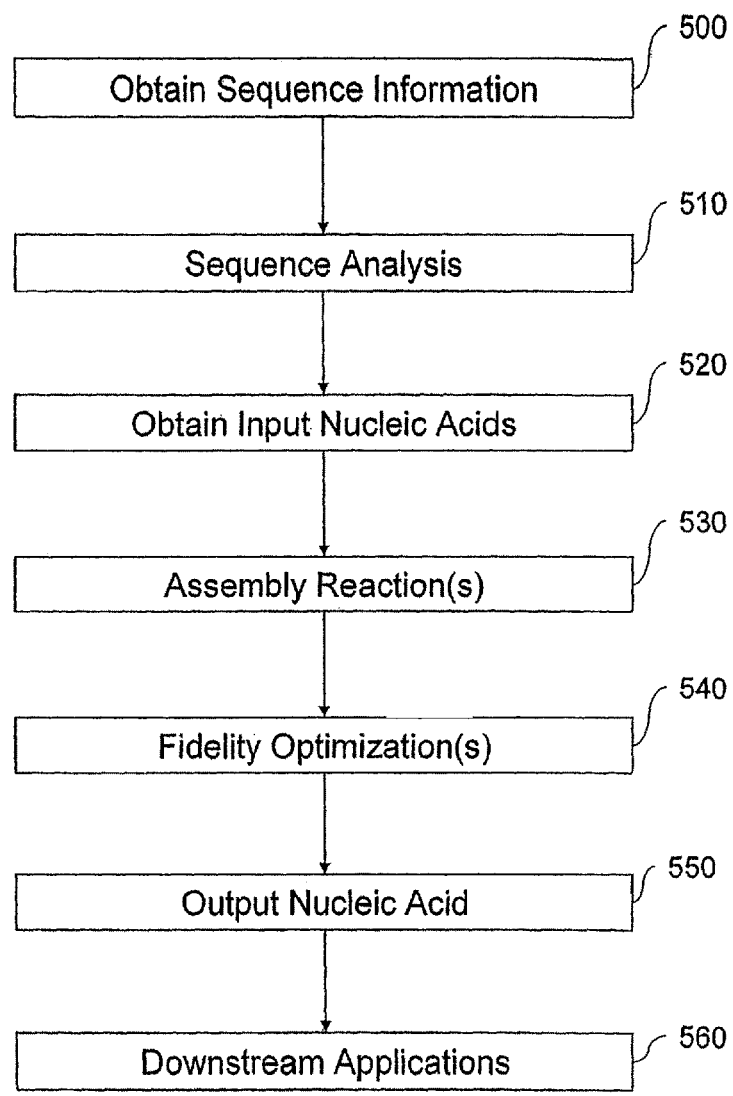
FIG. 5 illustrates an embodiment of a nucleic acid assembly procedure.

In some embodiments, a sequence analysis and design strategy of the invention may be incorporated in an assembly process outlined in FIG. 5.

FIG. 5 illustrates a method for assembling a nucleic acid in accordance with one embodiment of the invention. Initially, in act 500, sequence information is obtained. The sequence information may be the sequence of a predetermined target nucleic acid that is to be assembled. In some embodiments, the sequence may be received in the form of an order from a customer. The order may be received electronically or on a paper copy. In some embodiments, the sequence may be received as a nucleic acid sequence (e.g., DNA or RNA). In some embodiments, the sequence may be received as a protein sequence. The sequence may be converted into a DNA sequence. For example, if the sequence obtained in act 500 is an RNA sequence, the Us may be replaced with Ts to obtain the corresponding DNA sequence. If the sequence obtained in act 500 is a protein sequence, it may be converted into a DNA sequence using appropriate codons for the amino acids. When choosing codons for each amino acid, consideration may be given to one or more of the following factors: i) using codons that correspond to the codon bias in the organism in which the target nucleic acid may be expressed, ii) avoiding excessively high or low GC or AT contents in the target nucleic acid (for example, above 60% or below 40%; e.g., greater than 65%, 70%, 75%, 80%, 85%, or 90%; or less than 35%, 30%, 25%, 20%, 15%, or 10%), iii) avoiding sequence features that may interfere with the assembly procedure (e.g., the presence of repeat sequences, high GC content or stem loop structures), and/or iv) avoiding recognition sequences for one or more restriction enzymes that may be used in an assembly procedure (e.g., restriction enzyme sites 1-4 illustrated in FIGS. 6-8). Similar factors may be considered when designing non-coding nucleic acid sequences. However, these factors may be ignored in some embodiments as the invention is not limited in this respect. Also, aspects of the invention may be used to reduce errors caused by one or more of these factors. Accordingly, a DNA sequence determination (e.g., a sequence determination algorithm or an automated process for determining a target DNA sequence) may omit one or more steps relating to the analysis of the GC or AT content of the target nucleic acid sequence (e.g., the GC or AT content may be ignored in some embodiments) or one or more steps relating to the analysis of certain sequence features (e.g., sequence repeats, inverted repeats, etc.) that could interfere with an assembly reaction performed under standard conditions but may not interfere with an assembly reaction including one or more concerted assembly steps. In some embodiments, target or insert sequences may be designed or modified to remove one or more of the restriction enzyme sites that are used for the iterative assembly.

In act 510, the sequence information may be analyzed to determine an assembly strategy. This may involve determining whether the target nucleic acid will be assembled as a single fragment or if several intermediate fragments will be assembled separately and then combined in one or more additional rounds of assembly to generate the target nucleic acid.

A sequence analysis may involve deciding which fragments will be prepared to be assembled in a first vector using a vector-encoded trait activation technique of the invention. Nucleic acids being assembled may include one or more sequences that could act as activator sequences. In some embodiments, an assembly strategy may be designed to prevent these putative activator sequences (e.g., promoters, terminators, etc.) from being located on an assembly fragment at a location (e.g., at a 5' or 3' end) where they may activate a vector-encoded trait when the fragments are incorrectly assembled (e.g., inverted or cloned to the incorrect free end of a linearized vector, etc.). Accordingly, such putative activator sequences may be buried within the central regions (e.g., within about the middle 80%) of fragments that are being assembled.

A sequence analysis also may be important for choosing the restriction enzymes, activator sequences, or vector-encoded traits that will be used. For example, one or more enzymes chosen for assembly may be ones that are not present (or only present in small numbers) in the target sequence. Activator sequences and/or vector-encoded traits may be chosen so that they do not interfere with one or more functions (e.g., gene encoded functions) on the target nucleic acid. In some embodiments, ampicillin resistance may be avoided as an activatable marker if the target nucleic acid being assembled encodes beta lactamase or other enzyme that protects from (e.g., degrades or modifies) ampicillin.

Once the overall assembly strategy has been determined, input nucleic acids (e.g., oligonucleotides) for assembling the one or more nucleic acid fragments may be designed. The sizes and numbers of the input nucleic acids may be based in part on the type of assembly reaction (e.g., the type of polymerase-based assembly, ligase-based assembly, chemical assembly, or combination thereof) that is being used for each fragment. The input nucleic acids also may be designed to avoid 5' and/or 3' regions that may cross-react incorrectly and be assembled to produce undesired nucleic acid fragments. Other structural and/or sequence factors also may be considered when designing the input nucleic acids. In certain embodiments, some of the input nucleic acids may be designed to incorporate one or more specific sequences (e.g., primer binding sequences, restriction enzyme sites, etc.) at one or both ends of the assembled nucleic acid fragment.

In act 520, the input nucleic acids are obtained. These may be synthetic oligonucleotides that are synthesized on-site or obtained from a different site (e.g., from a commercial supplier). In some embodiments, one or more input nucleic acids may be amplification products (e.g., PCR products), restriction fragments, or other suitable nucleic acid molecules. Synthetic oligonucleotides may be synthesized using any appropriate technique as described in more detail herein. It should be appreciated that synthetic oligonucleotides often have sequence errors. Accordingly, oligonucleotide preparations may be selected or screened to remove error-containing molecules as described in more detail herein.

In act 530, an assembly reaction may be performed for each nucleic acid fragment. For each fragment, the input nucleic acids may be assembled using any appropriate assembly technique (e.g., a polymerase-based assembly, a ligase-based assembly, a chemical assembly, or any other multiplex nucleic acid assembly technique, or any combination thereof). An assembly reaction may result in the assembly of a number of different nucleic acid products in addition to the predetermined nucleic acid fragment. Accordingly, in some embodiments, an assembly reaction may be processed to remove incorrectly assembled nucleic acids (e.g., by size fractionation) and/or to enrich correctly assembled nucleic acids (e.g., by amplification, optionally followed by size fractionation). In some embodiments, correctly assembled nucleic acids may be amplified (e.g., in a PCR reaction) using primers that bind to the ends of the predetermined nucleic acid fragment. It should be appreciated that act 530 may be repeated one or more times. For example, in a first round of assembly a first plurality of input nucleic acids (e.g., oligonucleotides) may be assembled to generate a first nucleic acid fragment. In a second round of assembly, the first nucleic acid fragment may be combined with one or more additional nucleic acid fragments and used as starting material for the assembly of a larger nucleic acid fragment. In a third round of assembly, this larger fragment may be combined with yet further nucleic acids and used as starting material for the assembly of yet a larger nucleic acid. This procedure may be repeated as many times as needed for the synthesis of a target nucleic acid. Accordingly, progressively larger nucleic acids may be assembled. At each stage, nucleic acids of different sizes may be combined. At each stage, the nucleic acids being combined may have been previously assembled in a multiplex assembly reaction. However, at each stage, one or more nucleic acids being combined may have been obtained from different sources (e.g., PCR amplification of genomic DNA or cDNA, restriction digestion of a plasmid or genomic DNA, or any other suitable source).

One or more cycles of assembly may be performed using a vector-encoded trait-activation technique described herein.

It should be appreciated that nucleic acids generated in each cycle of assembly may contain sequence errors if they incorporated one or more input nucleic acids with sequence error(s). Accordingly, a fidelity optimization procedure may be performed after a cycle of assembly in order to remove or correct sequence errors. It should be appreciated that fidelity optimization may be performed after each assembly reaction when several consecutive cycles of assembly are performed. However, in certain embodiments fidelity optimization may be performed only after a subset (e.g., 2 or more) of consecutive assembly reactions are complete. In some embodiments, no fidelity optimization is performed.

Accordingly, act 540 is an optional fidelity optimization procedure. Act 540 may be used in some embodiments to remove nucleic acid fragments that seem to be correctly assembled (e.g., based on their size or restriction enzyme digestion pattern) but that may have incorporated input nucleic acids containing sequence errors as described herein. For example, since synthetic oligonucleotides may contain incorrect sequences due to errors introduced during oligonucleotide synthesis, it may be useful to remove nucleic acid fragments that have incorporated one or more error-containing oligonucleotides during assembly. In some embodiments, one or more assembled nucleic acid fragments may be sequenced to determine whether they contain the predetermined sequence or not. This procedure allows fragments with the correct sequence to be identified. However, in some embodiments, other techniques may be used to remove error containing nucleic acid fragments. It should be appreciated that error containing-nucleic acids may be double-stranded homoduplexes having the error on both strands (i.e., incorrect complementary nucleotide(s), deletion(s), or addition(s) on both strands), because the assembly procedure may involve one or more rounds of polymerase extension (e.g., during assembly or after assembly to amplify the assembled product)

during which an input nucleic acid containing an error may serve as a template thereby producing a complementary strand with the complementary error. In certain embodiments, a preparation of double-stranded nucleic acid fragments may be suspected to contain a mixture of nucleic acids that have the correct sequence and nucleic acids that incorporated one or more sequence errors during assembly. In some embodiments, sequence errors may be removed using a technique that involves denaturing and reannealing the double-stranded nucleic acids. In some embodiments, single strands of nucleic acids that contain complementary errors may be unlikely to reanneal together if nucleic acids containing each individual error are present in the nucleic acid preparation at a lower frequency than nucleic acids having the correct sequence at the same position. Rather, error containing single strands may reanneal with a complementary strand that contains no errors or that contains one or more different errors. As a result, error-containing strands may end up in the form of heteroduplex molecules in the reannealed reaction product. Nucleic acid strands that are error-free may reanneal with error-containing strands or with other error-free strands. Reannealed error-free strands form homoduplexes in the reannealed sample. Accordingly, by removing heteroduplex molecules from the reannealed preparation of nucleic acid fragments, the amount or frequency of error containing nucleic acids may be reduced. Any suitable method for removing heteroduplex molecules may be used, including chromatography, electrophoresis, selective binding of heteroduplex molecules, etc. In some embodiments, mismatch binding proteins that selectively (e.g., specifically) bind to heteroduplex nucleic acid molecules may be used. One example includes using MutS, a MutS homolog, or a combination thereof to bind to heteroduplex molecules. In *E. coli*, the MutS protein, which appears to function as a homodimer, serves as a mismatch recognition factor. In eukaryotes, at least three MutS Homolog (MSH) proteins have been identified; namely, MSH2, MSH3, and MSH6, and they form heterodimers. For example in the yeast, *Saccharomyces cerevisiae*, the MSH2-MSH6 complex (also known as MutSα) recognizes base mismatches and single nucleotide insertion/deletion loops, while the MSH2-MSH3 complex (also known as MutSβ) recognizes insertions/deletions of up to 12-16 nucleotides, although they exert substantially redundant functions. A mismatch binding protein may be obtained from recombinant or natural sources. A mismatch binding protein may be heat-stable. In some embodiments, a thermostable mismatch binding protein from a thermophilic organism may be used. Examples of thermostable DNA mismatch binding proteins include, but are not limited to: Tth MutS (from *Thermus thermophilus*); Taq MutS (from *Thermus aquaticus*); Apy MutS (from *Aquifex pyrophilus*); Tma MutS (from *Thermotoga maritima*); any other suitable MutS; or any combination of two or more thereof.

According to aspects of the invention, protein-bound heteroduplex molecules (e.g., heteroduplex molecules bound to one or more MutS proteins) may be removed from a sample using any suitable technique (binding to a column, a filter, a nitrocellulose filter, etc., or any combination thereof). It should be appreciated that this procedure may not be 100% efficient. Some errors may remain for at least one of the following reasons. Depending on the reaction conditions, not all of the double-stranded error-containing nucleic acids may be denatured. In addition, some of the denatured error-containing strands may reanneal with complementary error-containing strands to form an error containing homoduplex. Also, the MutS/heteroduplex interaction and the MutS/heteroduplex removal procedures may not be 100% efficient. Accordingly, in some embodiments the fidelity optimization act 540 may be repeated one or more times after each assembly reaction. For example, 2, 3, 4, 5, 6, 7, 8, 9, 10 or more cycles of fidelity optimization may be performed after each assembly reaction. In some embodiments, the nucleic acid is amplified after each fidelity optimization procedure. It should be appreciated that each cycle of fidelity optimization will remove additional error-containing nucleic acid molecules. However, the proportion of correct sequences is expected to reach a saturation level after a few cycles of this procedure.

In some embodiments, the size of an assembled nucleic acid that is fidelity optimized (e.g., using MutS or a MutS homolog) may be determined by the expected number of sequence errors that are suspected to be incorporated into the nucleic acid during assembly. For example, an assembled nucleic acid product should include error free nucleic acids prior to fidelity optimization in order to be able to enrich for the error free nucleic acids. Accordingly, error screening (e.g., using MutS or a MutS homolog) should be performed on shorter nucleic acid fragments when input nucleic acids have higher error rates. In some embodiments, one or more nucleic acid fragments of between about 200 and about 800 nucleotides (e.g., about 200, about 300, about 400, about 500, about 600, about 700 or about 800 nucleotides in length) are assembled prior to fidelity optimization. After assembly, the one or more fragments may be exposed to one or more rounds of fidelity optimization as described herein. In some embodiments, several assembled fragments may be ligated together (e.g., to produce a larger nucleic acid fragment of between about 1,000 and about 5,000 bases in length, or larger), and optionally cloned into a vector, prior to fidelity optimization as described herein.

At act 550, an output nucleic acid is obtained. As discussed herein, several rounds of act 530 and/or 540 may be performed to obtain the output nucleic acid, depending on the assembly strategy that is implemented. The output nucleic acid may be amplified, cloned, stored, etc., for subsequent uses at act 560. In some embodiments, an output nucleic acid may be cloned with one or more other nucleic acids (e.g., other output nucleic acids) for subsequent applications. Subsequent applications may include one or more research, diagnostic, medical, clinical, industrial, therapeutic, environmental, agricultural, or other uses.

It should be appreciated that each nucleic acid assembly may involve a combination of one or more extension, ligation, and/or cloning procedures. For example, in one embodiment, a target nucleic acid may be assembled entirely in vitro using multiplex extension reactions, ligation reactions, or a combination thereof. The resulting target nucleic acid product then may be transformed into a host cell (e.g., after insertion into a vector) for subsequent growth and amplification. However, in certain embodiments, a target nucleic acid may be assembled from a plurality of intermediate nucleic acids (e.g., shorter nucleic acids that will be combined to form the final target nucleic acid product) that have been inserted into vectors and amplified in vivo in a host cell. In some embodiments, a target nucleic acid assembly may involve preparing a first plurality of intermediate nucleic acids (e.g., using an in vitro multiplex assembly reaction for each intermediate nucleic acid), cloning each of the first plurality of intermediate nucleic acids into a vector for amplification in a host cell, isolating each of the first plurality of intermediate nucleic acids after amplification in the host cell, and assembling the first plurality of intermediate nucleic acids (e.g., via ligation) to obtain the target nucleic acid. This final assembly step may include cloning into an appropriate vector so that the target nucleic acid can be grown and amplified in an appropriate host cell.

In some embodiments, assembly of a target nucleic acid may involve several cycles of intermediate cloning. For example, a first plurality of intermediates may be cloned into an appropriate vector and amplified in a host cell. Subsets of the first plurality of intermediates (e.g., pairs of nucleic acids, or groups of 3, 4, 5, 6, 7, 8, 9, 10 or more intermediate nucleic acids from the first plurality) may subsequently be combined and assembled (e.g., by ligation) to form a second plurality of intermediates that are longer than the first plurality of intermediates (each of the second plurality of intermediates is assembled from one subset of the first plurality of intermediates described above). This second plurality of intermediates also may be cloned into an appropriate vector and amplified in a host cell. This second plurality of intermediates may be assembled directly to form the final target nucleic acid. Alternatively, this second plurality of intermediates may be cycled through one or more additional intermediate assembly procedures (e.g., forming third, fourth, fifth, sixth, or more pluralities of progressively longer intermediates) before a final nucleic acid is assembled.

Each of the first plurality of intermediates may be generated by ligation or extension (e.g., in an in vitro multiplex nucleic acid assembly reaction). The decision to further assemble the first plurality of intermediates using one or more cycles of cloning and amplification in host cells may be based on the properties of the intermediates (e.g., predicted or actual difficulties in further assembling them using only in vitro reactions). It should be appreciated overall that assembly time may be reduced by avoiding intermediate cloning steps that involve cell growth. Accordingly, in some embodiments, in vitro assembly techniques alone are used to generate a final nucleic acid product that subsequently may be cloned and propagated in a host cell. However, in some embodiments, one or more intermediates that are difficult to assemble correctly in an in vitro multiplex assembly reaction may be more readily assembled and amplified by cloning into a vector and transforming into a host cell. For example, the presence of one or more direct or inverted repeats, high GC content, etc., may cause assembly errors in an in vitro multiplex assembly reaction that can be avoided using one or more rounds of vector cloning and in vivo amplification. In some embodiments, nucleic acid size also may determine whether vector cloning and in vivo amplification are used for further assembly. In some embodiments, nucleic acids that are longer than about 1.5 kb may be further assembled using vector cloning and in vivo amplification. In some embodiments, nucleic acids may be predicted to be difficult to assemble using in vitro multiplex assembly (e.g., due to the presence of one or more sequence features predicted to interfere with in vitro multiplex assembly). In some embodiments, nucleic acids may be experimentally determined to be difficult to assemble correctly using in vitro multiplex assembly (e.g., a correct final product is not generated). In any of these situations, one or more assembly steps involving cloning and host cell transformation may be used to obtain a correct product of interest. Accordingly, an assembly strategy may be designed to provide an integrated overlapping enzyme system (also known as ION) that provides one or more intermediate cloning and host cell transformation cycles that may be combined with in vitro multiplex assembly steps.

Figure 9:
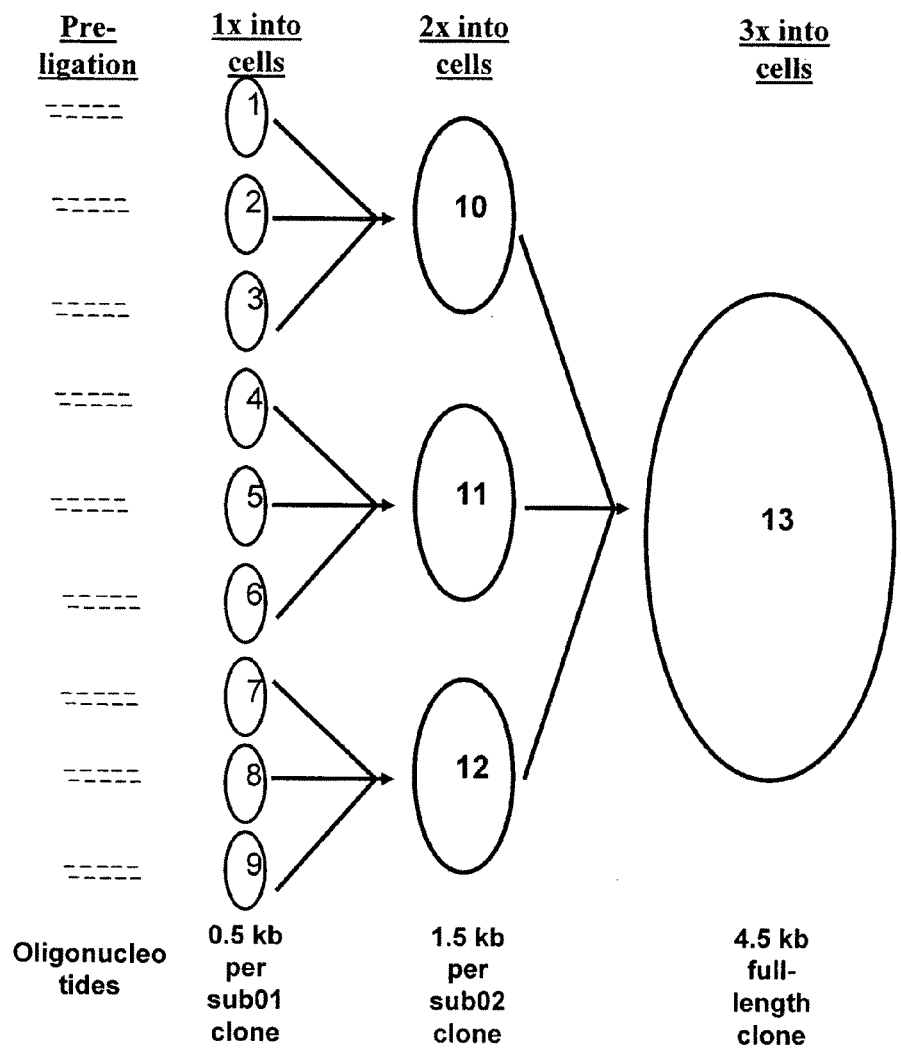
FIG. 9 illustrates a non-limiting embodiment of a hierarchical cloning strategy that may be integrated with one or more enzyme-mediated multiplex assembly steps.

In some embodiments, this assembly is hierarchical. A first plurality of first intermediates may be generated by any suitable method (e.g., ligation, extension, etc., or a combination thereof). Each first intermediate may be cloned into a first vector and amplified in a host cell preparation. These first intermediates then may be grouped together into subsets and the intermediates in each subset may be assembled and cloned into a second vector in a second cloning step. The intermediates in each subset correspond to adjacent sequences in the target nucleic acid. This second cloning step generates a second plurality of intermediates with a smaller number of larger intermediates than the first plurality. The ratio of the numbers of intermediates in the first and second pluralities is related to the number of first intermediates that are cloned together in each subset during the second cloning step. For example, if subsets of N first intermediates are combined and cloned together in the second cloning step, the number of intermediates in the second plurality will be 1/N the number of intermediates in the first plurality. However, it should be appreciated that different subsets may contain different numbers of first intermediates that are cloned together during the second cloning step. This cycle may be repeated one or more times (e.g., subsets of the second plurality of intermediates may be assembled in a third cloning step to generate a third plurality of intermediates, etc.) until a final single product is generated. For example, FIG. 9 illustrates a non-limiting embodiment of an integrated overlapping enzyme cloning strategy where nine first intermediates each approximately 0.5 kb in length are assembled (e.g., using a multiplex ligase or polymerase assembly), cloned into vectors, and transformed into host cells. Subsets of three first intermediates are then cloned together in a second cloning step to generate three second intermediates each approximately 1.5 kb in length. In a third cloning step, the three second intermediates are cloned together in a third cloning step to generate a full length target nucleic acid approximately 4.5 kb in length. It should be appreciated that the sizes of the intermediates that are used, the number of intermediates that are cloned together in each cycle, the number of cycles, and the length of the final product may vary, as the invention is not limited in this respect. In some embodiments, intermediates of about 1.5 kb in length are generated (e.g., in a polymerase-based in vitro multiplex assembly) and further assembled by cloning and host cell transformation.

It should be appreciated that fidelity optimization (e.g., by error removal using a mismatch recognition protein, for example, MUTS) may be performed and any one or more stages during the assembly. For example, fidelity optimization of the first intermediates may be performed (e.g., before or after they are cloned into the first vectors).

The cloning vectors that are used at each stage may be identical. However, different vectors may be used for different cloning reactions. For example, each cloning reaction may use a different vector. The different vectors may have different selectable markers. The different vectors may have different copy numbers. The different vectors may be adapted for inserts of different lengths. For example, vectors that are more suited for large inserts may be used at later stages in an assembly. In some embodiments, two different vectors (e.g., with different selectable markers) may be used and alternated in sequential cloning steps.

One or more assembly steps may be automated (e.g., using a robotic handler or a microfluidic device). Automation may be facilitated by avoiding fragment isolation (e.g., based on electrophoretic size separation) during one or more cloning steps associated with any stage of assembly described herein. In some embodiments, two or more first fragments (e.g., different first fragments) may be removed from two or more first vectors and cloned together into a second vector in a single reaction mixture that comprises one or more restriction enzymes and one or more ligases. Transfer of nucleic acid fragment inserts from the first vectors to the second vector may be promoted in a single reaction mixture containing the first and second vectors, a ligase, and one or more restriction enzymes. For example, if the restriction enzyme(s) excise the fragments from the first vector and the ligase ligates the fragments into the second vector in a form that is not cleaved by the restriction enzyme(s), the reaction is driven towards fragment assembly in the second vector because this integration is not reversed by the restriction enzyme. Selection for fragment integration into the second vector may be performed by using a different selectable markers on each of the two vectors (e.g., ampicillin resistance on the first vector and chloramphenicol resistance on the second vector). After simultaneous digestion and ligation, the reaction mixture may be transformed into a host cell that is then exposed to an appropriate selection. Any combination of different selectable markers and selections may be used if it enables the second vector containing the assembled first fragments to be selected over the first vectors. In the assembly reaction, the second vector may be provided in a linear form with incompatible free ends to avoid vector re-ligation that would generate a background of empty vectors having the second selectable marker. It should be appreciated that type IIS restrictions enzymes may be used to generate appropriate insert fragments from the first vectors. The type IIS sites may be located on a first vector on both sides of a fragment being excised. The type IIS sites may be oriented such that excised fragment does not contain the type IIS sites. As a result, the type IIS sites are not present in the second vector after fragment integration. It should be appreciated that the backbone of the second vector may be designed, selected, or modified to avoid containing any of the type IIS restriction sites that are used to excise the first fragments from the first vector. Each of the first fragments in the first vectors may be flanked by the same type IIS restriction site to allow excision of all of the fragments using the same enzyme. In some embodiments, different type IIS sites and enzymes may be used to excise fragments from different first vectors. However, they are preferably selected to generate appropriate compatible ends (e.g., complementary overhangs) so that the excised fragments can be ligated together without requiring any further processing. In one embodiment, three first vectors contain different fragments (a, b, and c) flanked by BbsI sites. The first vectors all encode ampicillin resistance. The first vectors are incubated in a single reaction along with Bbs I, a ligase (e.g., T4 ligase), and a second vector that encodes chloramphenicol resistance. The second vector may be linearized to generate free ends, each one of which is compatible with a free end of one of the first fragments. After transformation of the digestion/ligation reaction into a chloramphenicol sensitive host cell, a correctly ligated vector containing fragments a, b, and c in the correct order may be selected for using chloramphenicol. However, it should be appreciated that the method may be used with different restriction sites and enzymes, different ligases, different vectors with different selectable markers, and different numbers of inserts (e.g., 2, 3, 4, 5, 6, 7, 8, 9, 10, 10-20, or more), that may be assembled in a single concerted reaction according to the invention. This process may be repeated through several cycles by using vectors encoding different selectable markers at each cycle. In some embodiments, a pair of vectors encoding different selectable markers may be used. Each vector is used as the second (receiving) vector in alternate cycles.

It should be appreciated that a quality control procedure may be performed at one or more steps in a multi-stage assembly of the invention. For example, an ION assembly may involve a quality control at one or more intermediate stages. In some embodiments, quality control may be performed at each intermediate stage. A quality control procedure may include one or more techniques designed to distinguish incorrectly assembled intermediates from correctly assembled intermediates. For example, a quality control procedure may include sequencing, amplification (e.g., by PCR, LCR, etc.), restriction enzyme digestion, size analysis (e.g., using electrophoresis, mass spectrometry, etc.), any other suitable quality control technique, or any combination of two or more thereof. One advantage of real-time quality control during a multi-stage assembly is the early identification of one or more incorrectly assembled intermediates before the final product is generated and analyzed. An incorrectly assembled intermediate can be re-synthesized or re-assembled in a correct format and then re-introduced into an assembly process at an appropriate stage to be incorporated into a final nucleic acid product. In some embodiments, an incorrect assembly may be indicative of the presence, in the intermediate nucleic acid, of certain sequences that are difficult to assemble. Certain sequences may be difficult to assemble, because they contain sequences that are unstable (e.g., because they are toxic, they contain certain direct or inverted sequence repeats, etc. However, certain sequences may be difficult to assemble due to sequence features that interfere with an assembly reaction (e.g., because they contain certain direct or inverted sequence repeats, they contain high percentages of certain bases, for example they have a high GC content, etc.). In some embodiments, one or more alternative assembly techniques may be used to generate an intermediate nucleic acid that was incorrectly assembled using a first assembly technique. For example, a different vector and/or a different host organism may be used. Different assembly methods (e.g., extension, ligation, or a combination thereof) and/or different starting nucleic acids (e.g., different oligonucleotides, etc.) may be used. In some embodiments, two or more smaller fragments of an intermediate that was incorrectly assembled may be prepared. This may identify a smaller region that contains challenging sequences that can then be assembled using one or more alternative techniques. It should be appreciated that for some sequences, a correctly assembled nucleic acid (e.g., a correctly assembled intermediate) may be obtained without using alternative assembly techniques, but instead by screening a larger number of potential constructs (e.g., clones) to identify a correct one.

Concerted Assembly

According to aspects of the invention, a plurality of nucleic acid fragments may be assembled in a single concerted procedure wherein the plurality of fragments is mixed together under conditions that promote covalent assembly of the fragments to generate a specific longer nucleic. In some embodiments, concerted assembly techniques may be used in combination with iterative assembly techniques described herein (e.g., for example at different stages of an assembly process—or more that two inserts, for example 3, 4, 5, 6, 7, 8, 9, 10, or more may be added at each step of an iterative assembly described herein, wherein only the outer inserts have the activation sequences). According to aspects of the invention, a plurality of nucleic acid fragments may be covalently assembled in vivo in a host cell. In some embodiments, a plurality of nucleic acid fragments (e.g., n different nucleic acid fragments) may be mixed together without ligase and transformed into a host cell where they are covalently joined together to produce a longer nucleic acid (e.g., containing the n different nucleic acid fragments covalently liked together). However, a ligase and/or recombinase may be used in some embodiments (e.g., added to a plurality of nucleic acid fragments prior to a host cell transformation). In some embodiments, 5 or more (e.g., 10 or more, 15 or more, 15 to 20, 20 to 25, 25 to 30, 30 to 35, 35 to 40, 40 to 45, 45 to 50, 50 or more, etc.) different nucleic acid fragments may be assembled (e.g., in a concerted in vivo assembly without using ligase). However, it should be appreciated that any number of nucleic acids (e.g., 2, 3, 4, 5, 6, 7, 8, 9, 10, 11, 12, 13, 14, 15, 16, 17, 18, 19, 20, etc.) may be assembled using concerted assembly techniques. Each nucleic acid fragment being assembled may be between about 100 nucleotides long and about 1,000 nucleotides long (e.g., about 200, about 300, about 400, about 500, about 600, about 700, about 800, about 900). However, longer (e.g., about 2,500 or more nucleotides long, about 5,000 or more nucleotides long, about 7,500 or more nucleotides long, about 10,000 or more nucleotides long, etc.) or shorter nucleic acid fragments may be assembled using a concerted assembly technique (e.g., shotgun assembly into a plasmid vector). It should be appreciated that the size of each nucleic acid fragment may be independent of the size of other nucleic acid fragments added to a concerted assembly. However, in some embodiments, each nucleic acid fragment may be approximately the same size (e.g., between about 400 nucleotides long and about 800 nucleotides long). It should be appreciated that the length of a double-stranded DNA fragment may be indicated by the number of base pairs. As used herein, a nucleic acid fragment referred to as "x" nucleotides long corresponds to "x" base pairs in length when used in the context of a double-stranded DNA fragment.

In some embodiments, one or more nucleic acids being assembled in a concerted reaction (e.g., 1-5, 5-10, 10-15, 15-20, etc.) may be codon-optimized and/or non-naturally occurring. In some embodiments, all of the nucleic acids being assembled in a concerted reaction are codon-optimized and/or non-naturally occurring.

In some aspects of the invention, nucleic acid fragments being assembled are designed to have overlapping complementary sequences. In some embodiments, the nucleic acid fragments are double-stranded DNA fragments with 3' and/or 5' single-stranded overhangs. These overhangs may be cohesive ends that can anneal to complementary cohesive ends on different DNA fragments. According to aspects of the invention, the presence of complementary sequences (and particularly complementary cohesive ends) on two DNA fragments promotes their covalent assembly in vivo. In some embodiments, a plurality of DNA fragments with different overlapping complementary single-stranded cohesive ends are assembled and their order in the assembled nucleic acid product is determined by the identity of the cohesive ends on each fragment. For example, the nucleic acid fragments may be designed so that a first nucleic acid has a first cohesive end that is complementary to a first cohesive end of the vector and a second cohesive end that is complementary to a first cohesive end of a second nucleic acid. The second cohesive end of the second nucleic acid may be complementary to a first cohesive end of a third nucleic acid. The second cohesive end of the third nucleic acid may be complementary a first cohesive end of a fourth nucleic acid. And so on through to the final nucleic acid that has a first cohesive end that may be complementary to a second cohesive end on the penultimate nucleic acid. The second cohesive end of the final nucleic acid may be complementary to a second cohesive end of the vector. According to aspects of the invention, this technique may be used to generate a vector containing nucleic acid fragments assembled in a predetermined linear order (e.g., first, second, third, forth, . . . , final).

In certain embodiments, the overlapping complementary regions between adjacent nucleic acid fragments are designed (or selected) to be sufficiently different to promote (e.g., thermodynamically favor) assembly of a unique alignment of nucleic acid fragments (e.g., a selected or designed alignment of fragments). It should be appreciated that overlapping regions of different length may be used. In some embodiments, longer cohesive ends may be used when higher numbers of nucleic acid fragments are being assembled. Longer cohesive ends may provide more flexibility to design or select sufficiently distinct sequences to discriminate between correct cohesive end annealing (e.g., involving cohesive ends designed to anneal to each other) and incorrect cohesive end annealing (e.g., between non-complementary cohesive ends).

In some embodiments, two or more pairs of complementary cohesive ends between different nucleic acid fragments may be designed or selected to have identical or similar sequences in order to promote the assembly of products containing a relatively random arrangement (and/or number) of the fragments that have similar or identical cohesive ends. This may be useful to generate libraries of nucleic acid products with different sequence arrangements and/or different copy numbers of certain internal sequence regions.

As illustrated above, each of the two terminal nucleic acid fragments (e.g., the terminal fragment at each end of an assembled product) may be designed to have a cohesive end that is complementary to a cohesive end on a vector (e.g., on a linearized vector). These cohesive ends may be identical cohesive ends that can anneal to identical complementary terminal sequences on a linearized vector. However, in some embodiments the cohesive ends on the terminal fragments are different and the vector contains two different cohesive ends, one at each end of a linearized vector), each complementary to one of the terminal fragment cohesive ends. Accordingly, the vector may be a linearized plasmid that has two cohesive ends, each of which is complementary with one end of the assembled nucleic acid fragments.

In some embodiments, the nucleic acid fragments are mixed with a vector and incubated before transformation into a host cell. It should be appreciated that incubation under conditions that promote specific annealing of the cohesive ends may increase the frequency of assembly (e.g., correct assembly) upon transformation into the host organism. In some embodiments, the different cohesive ends are designed to have similar melting temperatures (e.g., within about 5° C. of each other) so that correct annealing of all of the fragments is promoted under the same conditions. Correct annealing may be promoted at a different temperature depending on the length of the cohesive ends that are used. In some embodiments, cohesive ends of between about 4 and about 30 nucleotides in length (e.g., cohesive ends of about 5, about 10, about 15, about 20, about 25, or about 30 nucleotides in length) may be used. Incubation temperatures may range from about 20° C. to about 50° C. (including, e.g., 37° C.). However, higher or lower temperatures may be used. The length of the incubation may be optimized based on the length of the overhangs, the complexity of the overhangs, and the number of different nucleic acids (and therefore the number of different overhangs) that are mixed together. The incubation time also may depend on the annealing temperature and the presence or absence of other agents in the mixture. For example, a nucleic acid binding protein and/or a recombinase may be added (e.g., RecA, for example a heat stable RecA protein). The resulting complex of nucleic acids may be transformed directly into a host without using a ligase. One or more host functions (e.g., ligation, recombination, any other suitable function, or any combination thereof) then form the covalently linked structure. In some embodiments, a ligase may be added prior to transformation. However, it should be appreciated that the expense of a ligase (including, for example, the expense of storing and dispensing the ligase, e.g., automatically) may be avoided by using a ligase-free concerted assembly method of the invention.

In some embodiments, nucleic acid fragments and a vector are transformed into a host cell without any prior incubation period (other than the time required for mixing the nucleic acids and performing the transformation). In some embodiments, a recombinase (for example RecA, e.g., a thermostable RecA) and/or a nucleic acid binding protein may be mixed with the nucleic acid fragments and the vector, and optionally incubated, prior to transformation into a host cell.

It should be appreciated that a plurality of nucleic acid fragments being assembled all may have complementary 3' overhangs, complementary 5' overhangs, or a combination thereof. However, the complementary regions of two nucleic acid fragments that are designed to be adjacent should have the same type of overhang. For example, if nucleic acid "n" has a 5' overhang at its second end, then nucleic acid "n+1" should have a 5' overhang at its first end. However, nucleic acid "n+1" may have a 3' overhang at its second end if nucleic acid "n+2" has a 3' overhang at its first end. It should be understood that different nucleic acid assembly configurations may be designed and constructed. For example, a concerted assembly may involve multiple copies of certain nucleic acids and single copies of other nucleic acids. In some embodiments, one or more nucleic acid fragments being assembled may have blunt ends. In some embodiments, double-stranded blunt ends may have overlapping identical sequences on nucleic acid fragments that are designed to be adjacent to each other on an assembled nucleic acid product.

Any suitable vector may be used for any assembly method described herein (e.g., concerted assembly, iterative assembly, etc., or any combination thereof) as the invention is not so limited. For example, a vector may be a plasmid, a bacterial vector, a viral vector, a phage vector, an insect vector, a yeast vector, a mammalian vector, a BAC, a YAC, or any other suitable vector. In some embodiments, a vector may be a vector that replicates in only one type of organism (e.g., bacterial, yeast, insect, mammalian, etc.) or in only one species of organism. Some vectors may have a broad host range. Some vectors may have different functional sequences (e.g., origins or replication, selectable markers, etc.) that are functional in different organisms. These may be used to shuttle the vector (and any nucleic acid fragment(s) that are cloned into the vector) between two different types of organism (e.g., between bacteria and mammals, yeast and mammals, etc.). In some embodiments, the type of vector that is used may be determined by the type of host cell that is chosen.

It should be appreciated that a vector may encode a detectable marker such as a selectable marker (e.g., antibiotic resistance, etc.) so that transformed cells can be selectively grown and the vector can be isolated and any insert can be characterized to determine whether it contains the desired assembled nucleic acid. The insert may be characterized using any suitable technique (e.g., size analysis, restriction fragment analysis, sequencing, etc.). In some embodiments, the presence of a correctly assembled nucleic acid in a vector may be assayed by determining whether a function predicted to be encoded by the correctly assembled nucleic acid is expressed in the host cell.

In some embodiments, host cells that harbor a vector containing a nucleic acid insert may be selected for or enriched by using one or more additional detectable or selectable markers that are only functional if a correct (e.g., designed) terminal nucleic acid fragments is cloned into the vector.

Accordingly, a host cell should have an appropriate phenotype to allow selection for one or more drug resistance markers encoded on a vector (or to allow detection of one or more detectable markers encoded on a vector). However, any suitable host cell type may be used (e.g., prokaryotic, eukaryotic, bacterial, yeast, insect, mammalian, etc.). In some embodiments, the type of host cell may be determined by the type of vector that is chosen. A host cell may be modified to have increased activity of one or more ligation and/or recombination functions. In some embodiments, a host cell may be selected on the basis of a high ligation and/or recombination activity. In some embodiments, a host cell may be modified to express (e.g., from the genome or a plasmid expression system) one or more ligase and/or recombinase enzymes.

A host cell may be transformed using any suitable technique (e.g., electroporation, chemical transformation, infection with a viral vector, etc.). Certain host organisms are more readily transformed than others. In some embodiments, all of the nucleic acid fragments and a linearized vector are mixed together and transformed into the host cell in a single step. However, in some embodiments, several transformations may be used to introduce all the fragments and vector into the cell (e.g., several consecutive transformations using subsets of the fragments). It should be appreciated that the linearized vector is preferably designed to have incompatible ends so that it can only be circularized (and thereby confer resistance to a selectable marker) if the appropriate fragments are cloned into the vector in the designed configuration. This avoids or reduces the occurrence of "empty" vectors after selection.

Single-Stranded Overhangs

Certain aspects of the invention involve double-stranded nucleic acids with single-stranded overhangs. Overhangs may be generated using any suitable technique.

In some embodiments, a double-stranded nucleic acid fragment (e.g., a fragment assembled in a multiplex assembly) may be digested with an appropriate restriction enzyme to generate a terminal single-stranded overhang. In some embodiments, fragments that are designed to be adjacent to each other in an assembled product may be digested with the same enzyme to expose complementary overhangs. In some embodiments, overhangs may be generated using a type IIS restriction enzyme. Type IIS restriction enzymes are enzymes that bind to a double stranded nucleic acid at one site, referred to as the recognition site, and make a single double stranded cut outside of the recognition site. The double stranded cut, referred to as the cleavage site, is generally situated 0-20 bases away from the recognition site. The recognition site is generally about 4-7 bp long. All type IIS restriction enzymes exhibit at least partial asymmetric recognition. Asymmetric recognition means that 5'→3' recognition sequences are different for each strand of the nucleic acid. The enzyme activity also shows polarity meaning that the cleavage sites are located on only one side of the recognition site. Thus, there is generally only one double stranded cut corresponding to each recognition site. Cleavage generally produces 1-5 nucleotide single-stranded overhangs, with 5' or 3' termini, although some enzymes produce blunt ends. Either cut is useful in the context of the invention, although in some instances those producing single-stranded overhangs are produced. To date, ~80 type IIS enzymes have been identified. Examples include but are not limited to BstF5 I, BtsC I, BsrD I, Bts I, Alw I, Bcc I, BsmA I, Ear I, Mly I (blunt), Ple I, Bmr I, Bsa I, BsmB I, Fau I, Mnl I, Sap I, Bbs I, BciV I, Hph I, Mbo II, BfuA I, BspCN I, BspM I, SfaN I, Hga I, BseR I, Bbv I, Eci I, Fok I, BceA I, BsmF I, BtgZ I, BpuE I, Bsg I, Mme I, BseG I, Bse3D I, BseM I, AclW I, Alw26 I, Bst6 I, BstMA I, Eam1104 I, Ksp632 I, Pps I, Sch I (blunt), Bfi I, Bso31 I, BspTN I, Eco31 I, Esp3 I, Smu I, Bfu I, Bpi I, BpuA I, BstV2 I, AsuHP I, Acc36 I, Lwe I, Aar I, BseM II, TspDT I, TspGW I, BseX I, BstV1 I, Eco57 I, Eco57M I, Gsu I, and Bcg I. Such enzymes and information regarding their recognition and cleavage sites are available from commercial suppliers such as NEB.

In some embodiments, each of a plurality of nucleic acid fragments designed for concerted assembly may have a type IIS restriction site at each end. The type IIS restriction sites may be oriented so that the cleavage sites are internal relative to the recognition sequences. As a result, enzyme digestion exposes an internal sequence (e.g., an overhang within an internal sequence) and removes the recognition sequences from the ends. Accordingly, the same type IIS sites may be used for both ends of all of the nucleic acid fragments being prepared for assembly. However, different type IIS sites also may be used. Two fragments that are designed to be adjacent in an assembled product each may include an identical overlapping terminal sequence and a flanking type IIS site that is appropriately located to expose complementary overhangs within the overlapping sequence upon restriction enzyme digestion. Accordingly, a plurality of nucleic acid fragments may be generated with different complementary overhangs. The restriction site at each end of a nucleic acid fragment may be located such that digestion with the appropriate type IIS enzyme removes the restriction site and exposes a single-stranded region that is complementary to a single-stranded region on a nucleic acid fragment that is designed to be adjacent in the assembled nucleic acid product. In some embodiments, one end of each of the two terminal nucleic acid fragments may be designed to have a single-stranded overhang (e.g., after digestion with an appropriate restriction enzyme) that is complementary to a single-stranded overhang of a linearized vector nucleic acid. Accordingly, the resulting nucleic acid fragments and vector may be transformed directly into a host cell. Alternatively, the nucleic acid fragments and vector may be incubated to promote hybridization and annealing of the complementary sequences prior to transformation in the host cell. It should be appreciated that a vector may be prepared using any one of the techniques described herein or any other suitable technique that produces a single-stranded overhang that would be complementary to an end of one of the terminal nucleic acid fragments.

It should be appreciated that a type IIS recognition site may be present within a sequence being assembled. If the corresponding type IIS restriction enzyme is used during one or more assembly steps described herein, unwanted restriction fragments may be generated and they may interfere with the yield of correctly assembled nucleic acids. One or more different strategies may be used to avoid unwanted type IIS cleavage.

In certain embodiments, an assembly strategy involves identifying type IIS recognition sites that are not present in a target nucleic acid of interest. One or more of these selected sites (and the corresponding enzymes) may be used in one or more assembly steps described herein without cutting the target nucleic acid at unwanted sites.

In some embodiments, a nucleic acid sequence may be designed to remove any type IIS recognition sites. In a coding sequence, the removal of such sites may be achieved while preserving the integrity of the nucleic acid sequence code. For example, the degeneracy of certain amino acid codons may allow nucleotide base substitutions to be made to remove a type IIS recognition site while retaining a codon for the same amino acid (e.g., replace one codon for another). Such substitutions are known to those of ordinary skill in the art and can be made using no more than routine methods.

In certain embodiments, a type IIS restriction enzyme recognition site on a nucleic acid being assembled may be masked to prevent unwanted cleavage at that site. A recognition site may be masked by using a masking molecule (e.g., a nucleic acid) that binds to the recognition site (e.g., because it is complementary to one of the strands in the recognition site). "Masking" of a cleavage site to prevent unwanted cleavage may in some circumstances be referred to as "blocking" (as in "a blocking oligonucleotide"), and it should be understood to mean the same. See, for example, Example 4. In certain embodiments, a recognition site may be masked with a molecule capable of masking a restriction enzyme recognition site by preventing cleavage without preventing the enzyme from binding to its recognition site (for example, pcPNA).

In certain embodiments, complete or partial methylation of a nucleic acid may be performed to prevent unwanted cleavage at the methylated site. However, in order to maintain cleavage at certain type IIS sites that are used during assembly (assembly recognition sites), a masking molecule (e.g., nucleic acid) may be used to prevent methylation at certain sites. Accordingly, one or more assembly recognition sites may be masked from methylation while the rest of the nucleic acid molecule is methylated. Methylation sensitive restriction enzymes may be used to cleave the cleavage site which is unmethylated. In some embodiments, complete methylation of a nucleic acid molecule may be followed by selective demethylation to allow cleavage only at the type IIS recognition site. In some instances, appropriate *E. coli* host strains should be selected according to the type of masking strategy being employed. For example, SssI methylated DNA is mcr sensitive. In such situations, an *E. coli* strain lacking mcrA, mcrBC and Mrr must be used or the DNA will be degraded. It is understood that the skilled artisan is familiar with how to select suitable host strains. Examples of suitable host strains include but are not limited to:
DH10B genotype: F$^-$ mcrA Δ(mrr-hsdRMS-mcrBC) φ80lacZΔM15 ΔlacX74 recA1 endA1 araΔ139 Δ(ara, leu) 7697 galU galK λ-rpsL (Str$^R$) nupG; and TOP10 genotype: F$^-$ mcrA Δ(mrr-hsdRMS-mcrBC) φ80lacZΔM15 ΔlacX74 recA1 araΔ139 Δ(ara-leu)7697 galU galK rpsL (Str$^R$) endA1 nupG.

Any suitable masking molecule may be used to prevent cleavage or to prevent methylation. Any suitable nucleic acid may be used, including, for example, DNA, peptide nucleic acid (PNA), pseudocomplementary peptide nucleic acid (pcPNA), locked nucleic acid (LNA), etc. A masking nucleic acid should be long enough to bind to a site with sufficient affinity to specifically prevent cleavage or methylation at that site. For example, a masking nucleic acid may be between about 15 and about 50 nucleotides long (or shorter or longer depending on the context). For example, a masking nucleic acid may be about 60 nucleotides long, about 30 nucleotides long, or any other suitable length. A masking molecule may be capable of binding to a nucleic acid molecule at more than one location and on either one or both strands of the molecule. In some embodiments, a different sequence specific masking nucleic acid may be used for each site that is being protected. In some embodiments, masking of a cleavage site may be achieved by forming a complex with a specific protein or using Hoogsteen base pairing to mask the cleavage site. In some embodiments, RecA or any other suitable recombinase may be included to assist the binding of a masking molecule (e.g., nucleic acid) to a nucleic acid site being protected from cleavage or methylation.

In some embodiments, instead of using a type IIS restriction enzyme, site specific cleavage may be obtained using specific cleavage of DNA molecules at RecA-mediated triple-stranded structures. For example, specific cleavage may be obtained using an enzyme capable of cleaving a nucleic acid molecule specifically at a site where a triple-stranded DNA structure is located (e.g., using S1 or BAL31). A triple-stranded DNA structure may be generated using a nucleic acid (e.g., oligonucleotide) that is complementary to one strand of a double-stranded target sequence of interest. The formation of a triple-stranded structure may be promoted by RecA or other suitable recombinase enzyme. Certain enzymes may then be used to cut both strands of the double-stranded target nucleic acid at the location of the triple-stranded structure. For example, S1 nuclease cut both strands of the double-stranded target nucleic acid in the context of a triple-stranded structure towards the 5' end of the nucleic acid (e.g., oligonucleotide) that was added to form the structure. Triple-stranded DNA may be formed at any location in a double stranded nucleic acid molecule. In some embodiments, a complementary nucleic acid molecule may be used to form a triple-stranded DNA molecule. In other embodiments a homologous deoxynucleotide may be used to form a triple-stranded DNA molecule. In certain embodiments, formation of a triple-stranded DNA molecule is performed in the presence of RecA protein. Further examples may be found in Shigemori et al. (2004, Nucleic Acids Research, 32(1):1-8). the entire contents of which are incorporated herein by reference. Accordingly, targeted triple-helix cleavage may be used instead of a type IIS cleavage in certain assembly reactions described herein to avoid cleavage at unwanted sites within a target nucleic acid.

In certain embodiments, a meganuclease restriction enzyme may be used to cleave a nucleic acid molecule at a rare position. Meganuclease restriction enzymes specifically recognize long nucleic acid target sites. In some embodiments, a meganuclease restriction enzyme cleaves both strands of a nucleic acid at its specific cleavage site. In some embodiments, a meganuclease recognition site may be about 12-45 base pairs. In other embodiments, a meganuclease recognition site may be about 10, about 15, about 20, about 25, about 30, about 35, about 40 or about 45 base pairs. Restriction enzymes with longer recognition sites also may be used. An example of a meganuclease is a homing endonuclease which may be found in phages, bacteria, archaebacteria and various eukaryotes (see for example Epinat et al., 2003, Nucleic Acids Research, 31(11):2953-2962; the entire contents of which are herein incorporated by reference). In certain embodiments, other rare-cutter enzymes may be used (e.g., NotI etc.). Accordingly, a meganuclease or rare-cutter recognition site may be used instead of a type IIS site in certain assembly reactions described herein (along with the appropriate meganucleases and/or rare-cutter enzymes) to avoid cleavage at unwanted sites within a target nucleic acid.

Enzymatic digestions of DNA with type II or site-specific restriction enzymes typically generate an overhang of four to six nucleotides. These short cohesive ends may be sufficient for ligating two fragments of DNA containing complementary termini. However, when joining multiple DNA fragments together, longer complementary cohesive termini are preferred to facilitate assembly and to ensure specificity. Accordingly, other techniques may be used to expose longer single-stranded overhangs.

In some embodiments, uracil DNA glycosylase (UDG) may be used to hydrolyze a uracil-glycosidic bond in a nucleic acid thereby removing uracil and creating an alkali-sensitive abasic site in the DNA which can be subsequently hydrolyzed by endonuclease, heat or alkali treatment. As a result, a portion of one strand of a double-stranded nucleic acid may be removed thereby exposing the complementary sequence in the form of a single-stranded overhang. This approach requires the deliberate incorporation of one or more uracil bases on one strand of a double-stranded nucleic acid fragment. This may be accomplished, for example, by amplifying a nucleic acid fragment using an amplification primer that contains a 3' terminal uracil. After treatment with UDG, the region of the primer 5' to the uracil may be released (e.g., upon dilution, incubation, exposure to mild denaturing conditions, etc.) thereby exposing the complementary sequence as a single-stranded overhang. It should be appreciated that the length of the overhang may be determined by the position of the uracil on the amplifying primer and by the length of the amplifying primer. UDG is commercially available from suppliers such as Roche Applied Science.

In other embodiments, a technique for exposing a single-stranded overhang may involve a polymerase (e.g., T4 DNA polymerase) that has a suitable editing function. For example, T4 DNA polymerase possesses 3'→5' exonuclease activity. While this activity favors single-stranded regions, it can function, albeit somewhat less efficiently, on blunt ends. Accordingly, in the absence of any exogenous nucleotides, the 3' ends of a nucleic acid fragment contacted with T4 DNA polymerase will be progressively digested. The 5'→3' polymerase activity of T4 may attempt to replace an excised nucleotide. However, by limiting the type of nucleotides available for incorporation, it is possible to avoid incorporation and favor further excision. In some embodiments, progressive excision on a 3'→5' strand may be halted at the first occurrence (in the 3'→5' direction) of one of the four nucleotides by providing that nucleotide in sufficient amounts in the reaction mixture. The presence of the nucleotide in the reaction will result in an equilibrium being reached between the excision of the nucleotide and its re-incorporation by T4. In some embodiments, a single-stranded overhang may be generated at both ends of a nucleic acid fragment (e.g., if each 3' end does not contain the nucleotide that is added in the T4 polymerase reaction). In some embodiments, the length of the overhang generated at each end is a function of the sequence at each end (e.g., the length of the 3' sequence that is free of the nucleotide that is added in the T4 polymerase reaction).

In some embodiments, single-stranded overhangs may be generated by incubating a double-stranded nucleic acid with a polymerase that has an editing function (e.g., T4 DNA polymerase) without adding any nucleotides. The length of the overhangs may be a function of the incubation time. Accordingly, suitable incubation conditions (including suitable incubation times, for example) may be determined to obtain suitable average overhangs (e.g., about 10, about 20, about 30, about 40, about 50 nucleotides long, etc.).

Sequence Analysis and Fragment Design and Selection for Concerted Assembly

Aspects of the invention may include analyzing the sequence of a target nucleic acid and designing an assembly strategy based on the identification of regions, within the target nucleic acid sequence, that can be used to generate appropriate cohesive ends (e.g., single-stranded overhangs). These regions may be used to define the ends of fragments that can be assembled (e.g., in a concerted reaction) to generate the target nucleic acid. The fragments can then be provided or made (e.g., in a multiplex assembly reaction). In some embodiments, a target nucleic acid sequence may be analyzed to identify regions that contain at most three different types of nucleotide (i.e., they are missing at least one of G, A, T, or C) on one strand of the target nucleic acid. These regions may be used to generate cohesive ends using a polymerase (e.g., T4 DNA polymerase) processing technique described herein. It should be appreciated that the length of a cohesive end is preferably sufficient to provide specificity. For example, cohesive ends may be long enough to have sufficiently different sequences to prevent or reduce mispairing between similar cohesive ends. However, their length is preferably not long enough to stabilize mispairs between similar cohesive sequences. In some embodiments, a length of about 9 to about 15 bases may be used. However, any suitable length may be selected for a region that is to be used to generate a cohesive overhang. The importance of specificity may depend on the number of different fragments that are being assembled simultaneously. Also, the appropriate length required to avoid stabilizing mispaired regions may depend on the conditions used for annealing different cohesive ends.

In some embodiments, a target nucleic acid sequence may be analyzed to identify potential cohesive end regions as follows. One or more regions (e.g., about 9-15 base long regions) free of either G, A, T, or C may be identified on one strand of a target nucleic acid. One or more regions (e.g., about 9-15 base regions) free of the complementary nucleotide may be identified on the same strand. For example, regions free of C and regions free of G may be identified on one strand of the target nucleic acid. Alternating regions (e.g., alternating C-free and G-free regions) may be selected to define the ends of nucleic acid fragments to be used for assembly so that both ends of each fragment can be processed to generate cohesive ends. For example, a fragment with a C-free region at one end and a G-free region at the other end of each strand can be processed to generate cohesive overhangs at each end. In this embodiment, the C-free region is the 3' region on both strands and the overhang is generated by adding C to the T4 polymerase reaction. Similar configurations may be used with any one of G, A, T, or C.

In some embodiments, alternating regions may be selected if they are separated by distances that define fragments with suitable lengths for the assembly design. In some embodiments, the alternating regions may be separated by about 200 to about 1,500 bases. However, any suitable shorter or longer distance may be selected. For example, the cohesive regions may be separated by about 500 to about 5,000 bases. It should be appreciated that different patterns of alternating regions may be available depending on several factors (e.g., depending on the sequence of the target nucleic acid, the chosen length of the cohesive ends, and the desired fragment length). In some embodiments, if several options are available, the regions may be selected to maximize the sequence differences between different cohesive ends.

Selection of the cohesive regions defines the fragments that will be assembled to generate the target nucleic acid. Accordingly, the fragment size may be between about 200 and about 1,500 base pairs long, between about 500 and about 5,000 bases long, or shorter or longer depending on the target nucleic acid.

The fragments may be generated or obtained using any suitable technique. In some embodiments, each fragment may be assembled (e.g., in a multiplex oligonucleotide assembly reaction) so that it is flanked by double stranded regions that will be used to generate the cohesive single-stranded regions.

A fragment may be amplified in vitro (e.g., by PCR, LCR, etc.). In some embodiments, a fragment may be amplified in vivo. For in vivo amplification, a nucleic acid may be cloned into a vector having suitable flanking restriction sites. The restriction sites may be used to excise a fragment with appropriate end sequences that can be used to generate cohesive ends (e.g., with appropriate single-stranded lengths). In some embodiments, type IIS restriction enzymes may be used to cut out an appropriate fragment. A type IIS restriction site may be provided by the vector into which a nucleic acid is cloned. Alternatively or additionally, a type IIS restriction site may be provided at the end of a nucleic acid that is cloned into a vector (e.g., at the end of a fragment that is assembled in a multiplex oligonucleotide assembly reaction). After amplification in vivo, a type IIS fragment may be isolated and processed as described herein to generate the cohesive ends. It should be appreciated that any type IIS enzyme may be used, provided that its restriction site is placed at a suitable distance from the cohesive region so that the type IIS fragment can be appropriately processed. A fragment may be processed to generate cohesive ends regardless of whether the type IIS digestion generates overhangs or blunt ends. In some embodiments, the overhangs generated by a type IIS enzyme may not be long enough to provide sufficient specificity.

In some embodiments, each fragment is assembled and fidelity optimized to remove error containing nucleic acids (e.g., using one or more post-assembly fidelity optimization techniques described herein) before being processed to generated cohesive ends. In some embodiments, the fidelity optimization may be performed on the synthesized fragments after they are ligated into a first vector used for amplification. However, in some embodiments, the fragments may not be fidelity optimized, or they may be fidelity optimized after treatment to generate cohesive ends.

It should be appreciated that the different nucleic acid fragments that are used to assemble a target nucleic acid may be obtained or synthesized using different techniques. However, in some embodiments they are all produced using the same technique (e.g., assembled in a multiplex oligonucleotide assembly reaction, cloned into a vector, digested with a type IIS enzyme, and processed with T4 DNA polymerase). The resulting fragments may be assembled in a single step concerted reaction and, for example, cloned into a vector that has a selectable marker. The assembly may include an in vitro ligation. However, in some embodiments, the assembly may be an in vivo shotgun assembly wherein the fragments are transformed into a host cell without undergoing an in vitro ligation.

In some embodiments, fragments are amplified in a first vector that has a first selectable marker and are then combined and assembled into a second vector that has a second selectable marker. As a result, selection for the second selectable marker avoids contamination with the first vector. Accordingly, the reactions may be performed in a procedure that does not require removal (e.g., by purification) of the first vector sequence.

Aspects of the invention may include automating one or more acts described herein. For example, sequence analysis, the identification of interfering sequence features, assembly strategy selection (including fragment design and selection, the choice of a particular combination of extension-based and ligation-based assembly reactions, etc.), fragment production, single-stranded overhang production, and/or concerted assembly may be automated in order to generate the desired product automatically. Acts of the invention may be automated using, for example, a computer system.

Aspects of the invention may be used in conjunction with any suitable multiplex nucleic acid assembly procedure. For example, vector-encoded trait activation may be used in connection with or more of the multiplex nucleic acid assembly procedures described below.

Multiplex Nucleic Acid Assembly

Aspects of the invention may involve an assembly procedure wherein a plurality of nucleic acids each assembled in a multiplex assembly procedure (e.g., from oligonucleotides)

are combined to form a larger nucleic acid using an iterative assembly procedure described herein. In aspects of the invention, multiplex nucleic acid assembly relates to the assembly of a plurality of nucleic acids to generate a longer nucleic acid product. In one aspect, multiplex oligonucleotide assembly relates to the assembly of a plurality of oligonucleotides to generate a longer nucleic acid molecule. However, it should be appreciated that other nucleic acids (e.g., single or double-stranded nucleic acid degradation products, restriction fragments, amplification products, naturally occurring small nucleic acids, other polynucleotides, etc.) may be assembled or included in a multiplex assembly reaction (e.g., along with one or more oligonucleotides) in order to generate an assembled nucleic acid molecule that is longer than any of the single starting nucleic acids (e.g., oligonucleotides) that were added to the assembly reaction. In certain embodiments, one or more nucleic acid fragments that each were assembled in separate multiplex assembly reactions (e.g., separate multiplex oligonucleotide assembly reactions) may be combined and assembled to form a further nucleic acid that is longer than any of the input nucleic acid fragments. In certain embodiments, one or more nucleic acid fragments that each were assembled in separate multiplex assembly reactions (e.g., separate multiplex oligonucleotide assembly reactions) may be combined with one or more additional nucleic acids (e.g., single or double-stranded nucleic acid degradation products, restriction fragments, amplification products, naturally occurring small nucleic acids, other polynucleotides, etc.) and assembled to form a further nucleic acid that is longer than any of the input nucleic acids.

In aspects of the invention, one or more multiplex assembly reactions may be used to generate target nucleic acids having predetermined sequences. In one aspect, a target nucleic acid may have a sequence of a naturally occurring gene and/or other naturally occurring nucleic acid (e.g., a naturally occurring coding sequence, regulatory sequence, non-coding sequence, chromosomal structural sequence such as a telomere or centromere sequence, etc., any fragment thereof or any combination of two or more thereof). In another aspect, a target nucleic acid may have a sequence that is not naturally-occurring. In one embodiment, a target nucleic acid may be designed to have a sequence that differs from a natural sequence at one or more positions. In other embodiments, a target nucleic acid may be designed to have an entirely novel sequence. However, it should be appreciated that target nucleic acids may include one or more naturally occurring sequences, non-naturally occurring sequences, or combinations thereof.

In one aspect of the invention, multiplex assembly may be used to generate libraries of nucleic acids having different sequences. In some embodiments, a library may contain nucleic acids having random sequences. In certain embodiments, a predetermined target nucleic acid may be designed and assembled to include one or more random sequences at one or more predetermined positions.

In certain embodiments, a target nucleic acid may include a functional sequence (e.g., a protein binding sequence, a regulatory sequence, a sequence encoding a functional protein, etc., or any combination thereof). However, some embodiments of a target nucleic acid may lack a specific functional sequence (e.g., a target nucleic acid may include only non-functional fragments or variants of a protein binding sequence, regulatory sequence, or protein encoding sequence, or any other non-functional naturally-occurring or synthetic sequence, or any non-functional combination thereof). Certain target nucleic acids may include both functional and non-functional sequences. These and other aspects of target nucleic acids and their uses are described in more detail herein.

A target nucleic acid may be assembled in a single multiplex assembly reaction (e.g., a single oligonucleotide assembly reaction). However, a target nucleic acid also may be assembled from a plurality of nucleic acid fragments, each of which may have been generated in a separate multiplex oligonucleotide assembly reaction. It should be appreciated that one or more nucleic acid fragments generated via multiplex oligonucleotide assembly also may be combined with one or more nucleic acid molecules obtained from another source (e.g., a restriction fragment, a nucleic acid amplification product, etc.) to form a target nucleic acid. In some embodiments, a target nucleic acid that is assembled in a first reaction may be used as an input nucleic acid fragment for a subsequent assembly reaction to produce a larger target nucleic acid.

Accordingly, different strategies may be used to produce a target nucleic acid having a predetermined sequence. For example, different starting nucleic acids (e.g., different sets of predetermined nucleic acids) may be assembled to produce the same predetermined target nucleic acid sequence. Also, predetermined nucleic acid fragments may be assembled using one or more different in vitro and/or in vivo techniques. For example, nucleic acids (e.g., overlapping nucleic acid fragments) may be assembled in an in vitro reaction using an enzyme (e.g., a ligase and/or a polymerase) or a chemical reaction (e.g., a chemical ligation) or in vivo (e.g., assembled in a host cell after transfection into the host cell), or a combination thereof. Similarly, each nucleic acid fragment that is used to make a target nucleic acid may be assembled from different sets of oligonucleotides. Also, a nucleic acid fragment may be assembled using an in vitro or an in vivo technique (e.g., an in vitro or in vivo polymerase, recombinase, and/or ligase based assembly process). In addition, different in vitro assembly reactions may be used to produce a nucleic acid fragment. For example, an in vitro oligonucleotide assembly reaction may involve one or more polymerases, ligases, other suitable enzymes, chemical reactions, or any combination thereof.

Multiplex Oligonucleotide Assembly

A predetermined nucleic acid fragment may be assembled from a plurality of different starting nucleic acids (e.g., oligonucleotides) in a multiplex assembly reaction (e.g., a multiplex enzyme-mediated reaction, a multiplex chemical assembly reaction, or a combination thereof). Certain aspects of multiplex nucleic acid assembly reactions are illustrated by the following description of certain embodiments of multiplex oligonucleotide assembly reactions. It should be appreciated that the description of the assembly reactions in the context of oligonucleotides is not intended to be limiting. The assembly reactions described herein may be performed using starting nucleic acids obtained from one or more different sources (e.g., synthetic or natural polynucleotides, nucleic acid amplification products, nucleic acid degradation products, oligonucleotides, etc.). The starting nucleic acids may be referred to as assembly nucleic acids (e.g., assembly oligonucleotides). As used herein, an assembly nucleic acid has a sequence that is designed to be incorporated into the nucleic acid product generated during the assembly process. However, it should be appreciated that the description of the assembly reactions in the context of single-stranded nucleic acids is not intended to be limiting. In some embodiments, one or more of the starting nucleic acids illustrated in the figures and described herein may be provided as double stranded nucleic acids. Accordingly, it should be appreciated that where the figures and description illustrate the assembly of single-stranded nucleic acids, the presence of one or more complementary nucleic acids is contemplated. Accordingly, one or more double-stranded complementary nucleic acids may be included in a reaction that is described herein in the context of a single-stranded assembly nucleic acid. However, in some embodiments the presence of one or more complementary nucleic acids may interfere with an assembly reaction by competing for hybridization with one of the input assembly nucleic acids. Accordingly, in some embodiments an assembly reaction may involve only single-stranded assembly nucleic acids (i.e., the assembly nucleic acids may be provided in a single-stranded form without their complementary strand) as described or illustrated herein. However, in certain embodiments the presence of one or more complementary nucleic acids may have no or little effect on the assembly reaction. In some embodiments, complementary nucleic acid(s) may be incorporated during one or more steps of an assembly. In yet further embodiments, assembly nucleic acids and their complementary strands may be assembled under the same assembly conditions via parallel assembly reactions in the same reaction mixture. In certain embodiments, a nucleic acid product resulting from the assembly of a plurality of starting nucleic acids may be identical to the nucleic acid product that results from the assembly of nucleic acids that are complementary to the starting nucleic acids (e.g., in some embodiments where the assembly steps result in the production of a double-stranded nucleic acid product). As used herein, an oligonucleotide may be a nucleic acid molecule comprising at least two covalently bonded nucleotide residues. In some embodiments, an oligonucleotide may be between 10 and 1,000 nucleotides long. For example, an oligonucleotide may be between 10 and 500 nucleotides long, or between 500 and 1,000 nucleotides long. In some embodiments, an oligonucleotide may be between about 20 and about 100 nucleotides long (e.g., from about 30 to 90, 40 to 85, 50 to 80, 60 to 75, or about 65 or about 70 nucleotides long), between about 100 and about 200, between about 200 and about 300 nucleotides, between about 300 and about 400, or between about 400 and about 500 nucleotides long. However, shorter or longer oligonucleotides may be used. An oligonucleotide may be a single-stranded nucleic acid. However, in some embodiments a double-stranded oligonucleotide may be used as described herein. In certain embodiments, an oligonucleotide may be chemically synthesized as described in more detail below.

In some embodiments, an input nucleic acid (e.g., oligonucleotide) may be amplified before use. The resulting product may be double-stranded. In some embodiments, one of the strands of a double-stranded nucleic acid may be removed before use so that only a predetermined single strand is added to an assembly reaction.

In certain embodiments, each oligonucleotide may be designed to have a sequence that is identical to a different portion of the sequence of a predetermined target nucleic acid that is to be assembled. Accordingly, in some embodiments each oligonucleotide may have a sequence that is identical to a portion of one of the two strands of a double-stranded target nucleic acid. For clarity, the two complementary strands of a double stranded nucleic acid are referred to herein as the positive (P) and negative (N) strands. This designation is not intended to imply that the strands are sense and anti-sense strands of a coding sequence. They refer only to the two complementary strands of a nucleic acid (e.g., a target nucleic acid, an intermediate nucleic acid fragment, etc.) regardless of the sequence or function of the nucleic acid. Accordingly, in some embodiments a P strand may be a sense strand of a coding sequence, whereas in other embodiments a P strand may be an anti-sense strand of a coding sequence. According to the invention, a target nucleic acid may be either the P strand, the N strand, or a double-stranded nucleic acid comprising both the P and N strands.

It should be appreciated that different oligonucleotides may be designed to have different lengths. In some embodiments, one or more different oligonucleotides may have overlapping sequence regions (e.g., overlapping 5' regions or overlapping 3' regions). Overlapping sequence regions may be identical (i.e., corresponding to the same strand of the nucleic acid fragment) or complementary (i.e., corresponding to complementary strands of the nucleic acid fragment). The plurality of oligonucleotides may include one or more oligonucleotide pairs with overlapping identical sequence regions, one or more oligonucleotide pairs with overlapping complementary sequence regions, or a combination thereof. Overlapping sequences may be of any suitable length. For example, overlapping sequences may encompass the entire length of one or more nucleic acids used in an assembly reaction. Overlapping sequences may be between about 5 and about 500 nucleotides long (e.g., between about 10 and 100, between about 10 and 75, between about 10 and 50, about 20, about 25, about 30, about 35, about 40, about 45, about 50, etc.) However, shorter, longer or intermediate overlapping lengths may be used. It should be appreciated that overlaps between different input nucleic acids used in an assembly reaction may have different lengths.

In a multiplex oligonucleotide assembly reaction designed to generate a predetermined nucleic acid fragment, the combined sequences of the different oligonucleotides in the reaction may span the sequence of the entire nucleic acid fragment on either the positive strand, the negative strand, both strands, or a combination of portions of the positive strand and portions of the negative strand. The plurality of different oligonucleotides may provide either positive sequences, negative sequences, or a combination of both positive and negative sequences corresponding to the entire sequence of the nucleic acid fragment to be assembled. In some embodiments, the plurality of oligonucleotides may include one or more oligonucleotides having sequences identical to one or more portions of the positive sequence, and one or more oligonucleotides having sequences that are identical to one or more portions of the negative sequence of the nucleic acid fragment. One or more pairs of different oligonucleotides may include sequences that are identical to overlapping portions of the predetermined nucleic acid fragment sequence as described herein (e.g., overlapping sequence portions from the same or from complementary strands of the nucleic acid fragment). In some embodiments, the plurality of oligonucleotides includes a set of oligonucleotides having sequences that combine to span the entire positive sequence and a set oligonucleotides having sequences that combine to span the entire negative sequence of the predetermined nucleic acid fragment. However, in certain embodiments, the plurality of oligonucleotides may include one or more oligonucleotides with sequences that are identical to sequence portions on one strand (either the positive or negative strand) of the nucleic acid fragment, but no oligonucleotides with sequences that are complementary to those sequence portions. In one embodiment, a plurality of oligonucleotides includes only oligonucleotides having sequences identical to portions of the positive sequence of the predetermined nucleic acid fragment. In one embodiment, a plurality of oligonucleotides includes only oligonucleotides having sequences identical to portions of the negative sequence of the predetermined nucleic acid fragment. These oligonucleotides may be assembled by sequential ligation or in an extension-based reaction (e.g., if an oligonucleotide having a 3' region that is complementary to one of the plurality of oligonucleotides is added to the reaction).

In one aspect, a nucleic acid fragment may be assembled in a polymerase-mediated assembly reaction from a plurality of oligonucleotides that are combined and extended in one or more rounds of polymerase-mediated extensions. In another aspect, a nucleic acid fragment may be assembled in a ligase-mediated reaction from a plurality of oligonucleotides that are combined and ligated in one or more rounds of ligase-mediated ligations. In another aspect, a nucleic acid fragment may be assembled in a non-enzymatic reaction (e.g., a chemical reaction) from a plurality of oligonucleotides that are combined and assembled in one or more rounds of non-enzymatic reactions. In some embodiments, a nucleic acid fragment may be assembled using a combination of polymerase, ligase, and/or non-enzymatic reactions. For example, both polymerase(s) and ligase(s) may be included in an assembly reaction mixture. Accordingly, a nucleic acid may be assembled via coupled amplification and ligation or ligation during amplification. The resulting nucleic acid fragment from each assembly technique may have a sequence that includes the sequences of each of the plurality of assembly oligonucleotides that were used as described herein. These assembly reactions may be referred to as primerless assemblies, since the target nucleic acid is generated by assembling the input oligonucleotides rather than being generated in an amplification reaction where the oligonucleotides act as amplification primers to amplify a pre-existing template nucleic acid molecule corresponding to the target nucleic acid.

Polymerase-based assembly techniques may involve one or more suitable polymerase enzymes that can catalyze a template-based extension of a nucleic acid in a 5' to 3' direction in the presence of suitable nucleotides and an annealed template. A polymerase may be thermostable. A polymerase may be obtained from recombinant or natural sources. In some embodiments, a thermostable polymerase from a thermophilic organism may be used. In some embodiments, a polymerase may include a 3'→5', exonuclease/proofreading activity. In some embodiments, a polymerase may have no, or little, proofreading activity (e.g., a polymerase may be a recombinant variant of a natural polymerase that has been modified to reduce its proofreading activity). Examples of thermostable DNA polymerases include, but are not limited to: Taq (a heat-stable DNA polymerase from the bacterium *Thermus aquaticus*); Pfu (a thermophilic DNA polymerase with a 3'→5' exonuclease/proofreading activity from *Pyrococcus furiosus*, available from for example Promega); VentR® DNA Polymerase and VentR® (exo-) DNA Polymerase (thermophilic DNA polymerases with or without a 3'→5' exonuclease/proofreading activity from *Thermococcus litoralis*; also known as Tli polymerase); Deep VentR® DNA Polymerase and Deep VentR® (exo-) DNA Polymerase (thermophilic DNA polymerases with or without a 3'→5' exonuclease/proofreading activity from *Pyrococcus* species GB-D; available from New England Biolabs); KOD HiFi (a recombinant *Thermococcus kodakaraensis* KOD1 DNA polymerase with a 3'→5' exonuclease/proofreading activity, available from Novagen); BIO-X-ACT (a mix of polymerases that possesses 5'-3' DNA polymerase activity and 3'→5' proofreading activity); Klenow Fragment (an N-terminal truncation of *E. coli* DNA Polymerase I which retains polymerase activity, but has lost the 5'→3', exonuclease activity, available from, for example, Promega and NEB); Sequenase™ (T7 DNA polymerase deficient in 3'→5' exonuclease activity); Phi29 (bacteriophage 29 DNA polymerase, may be used for rolling circle amplification, for example, in a TempliPhi™ DNA Sequencing Template Amplification Kit, available from Amersham Biosciences); TopoTaq™ (a hybrid polymerase that combines hyperstable DNA binding domains and the DNA unlinking activity of *Methanopyrus* topoisomerase, with no exonuclease activity, available from Fidelity Systems); TopoTaq HiFi which incorporates a proofreading domain with exonuclease activity; Phusion™ (a *Pyrococcus*-like enzyme with a processivity-enhancing domain, available from New England Biolabs); any other suitable DNA polymerase, or any combination of two or more thereof.

Ligase-based assembly techniques may involve one or more suitable ligase enzymes that can catalyze the covalent linking of adjacent 3' and 5' nucleic acid termini (e.g., a 5' phosphate and a 3' hydroxyl of nucleic acid(s) annealed on a complementary template nucleic acid such that the 3' terminus is immediately adjacent to the 5' terminus). Accordingly, a ligase may catalyze a ligation reaction between the 5' phosphate of a first nucleic acid to the 3' hydroxyl of a second nucleic acid if the first and second nucleic acids are annealed next to each other on a template nucleic acid). A ligase may be obtained from recombinant or natural sources. A ligase may be a heat-stable ligase. In some embodiments, a thermostable ligase from a thermophilic organism may be used. Examples of thermostable DNA ligases include, but are not limited to: Tth DNA ligase (from *Thermus thermophilus*, available from, for example, Eurogentec and GeneCraft); Pfu DNA ligase (a hyperthermophilic ligase from *Pyrococcus furiosus*); Taq ligase (from *Thermus aquaticus*), any other suitable heat-stable ligase, or any combination thereof. In some embodiments, one or more lower temperature ligases may be used (e.g., T4 DNA ligase). A lower temperature ligase may be useful for shorter overhangs (e.g., about 3, about 4, about 5, or about 6 base overhangs) that may not be stable at higher temperatures.

Non-enzymatic techniques can be used to ligate nucleic acids. For example, a 5'-end (e.g., the 5' phosphate group) and a 3'-end (e.g., the 3' hydroxyl) of one or more nucleic acids may be covalently linked together without using enzymes (e.g., without using a ligase). In some embodiments, non-enzymatic techniques may offer certain advantages over enzyme-based ligations. For example, non-enzymatic techniques may have a high tolerance of non-natural nucleotide analogues in nucleic acid substrates, may be used to ligate short nucleic acid substrates, may be used to ligate RNA substrates, and/or may be cheaper and/or more suited to certain automated (e.g., high throughput) applications.

Non-enzymatic ligation may involve a chemical ligation. In some embodiments, nucleic acid termini of two or more different nucleic acids may be chemically ligated. In some embodiments, nucleic acid termini of a single nucleic acid may be chemically ligated (e.g., to circularize the nucleic acid). It should be appreciated that both strands at a first double-stranded nucleic acid terminus may be chemically ligated to both strands at a second double-stranded nucleic acid terminus. However, in some embodiments only one strand of a first nucleic acid terminus may be chemically ligated to a single strand of a second nucleic acid terminus. For example, the 5' end of one strand of a first nucleic acid terminus may be ligated to the 3' end of one strand of a second nucleic acid terminus without the ends of the complementary strands being chemically ligated.

Accordingly, a chemical ligation may be used to form a covalent linkage between a 5' terminus of a first nucleic acid end and a 3' terminus of a second nucleic acid end, wherein the first and second nucleic acid ends may be ends of a single nucleic acid or ends of separate nucleic acids. In one aspect, chemical ligation may involve at least one nucleic acid substrate having a modified end (e.g., a modified 5' and/or 3' terminus) including one or more chemically reactive moieties that facilitate or promote linkage formation. In some embodiments, chemical ligation occurs when one or more nucleic acid termini are brought together in close proximity (e.g., when the termini are brought together due to annealing between complementary nucleic acid sequences). Accordingly, annealing between complementary 3' or 5' overhangs (e.g., overhangs generated by restriction enzyme cleavage of a double-stranded nucleic acid) or between any combination of complementary nucleic acids that results in a 3' terminus being brought into close proximity with a 5' terminus (e.g., the 3' and 5' termini are adjacent to each other when the nucleic acids are annealed to a complementary template nucleic acid) may promote a template-directed chemical ligation. Examples of chemical reactions may include, but are not limited to, condensation, reduction, and/or photo-chemical ligation reactions. It should be appreciated that in some embodiments chemical ligation can be used to produce naturally-occurring phosphodiester internucleotide linkages, non-naturally-occurring phosphamide pyrophosphate internucleotide linkages, and/or other non-naturally-occurring internucleotide linkages.

In some embodiments, the process of chemical ligation may involve one or more coupling agents to catalyze the ligation reaction. A coupling agent may promote a ligation reaction between reactive groups in adjacent nucleic acids (e.g., between a 5'-reactive moiety and a 3'-reactive moiety at adjacent sites along a complementary template). In some embodiments, a coupling agent may be a reducing reagent (e.g., ferricyanide), a condensing reagent such (e.g., cyanoimidazole, cyanogen bromide, carbodiimide, etc.), or irradiation (e.g., UV irradiation for photo-ligation).

In some embodiments, a chemical ligation may be an autoligation reaction that does not involve a separate coupling agent. In autoligation, the presence of a reactive group on one or more nucleic acids may be sufficient to catalyze a chemical ligation between nucleic acid termini without the addition of a coupling agent (see, for example, Xu Y & Kool ET, 1997, Tetrahedron Lett. 38:5595-8). Non-limiting examples of these reagent-free ligation reactions may involve nucleophilic displacements of sulfur on bromoacetyl, tosyl, or iodonucleoside groups (see, for example, Xu Y et al., 2001, Nat Biotech 19:148-52). Nucleic acids containing reactive groups suitable for autoligation can be prepared directly on automated synthesizers (see, for example, Xu Y & Kool ET, 1999, Nuc. Acids Res. 27:875-81). In some embodiments, a phosphorothioate at a 3' terminus may react with a leaving group (such as tosylate or iodide) on a thymidine at an adjacent 5' terminus. In some embodiments, two nucleic acid strands bound at adjacent sites on a complementary target strand may undergo auto-ligation by displacement of a 5'-end iodide moiety (or tosylate) with a 3'-end sulfur moiety. Accordingly, in some embodiments the product of an autoligation may include a non-naturally-occurring internucleotide linkage (e.g., a single oxygen atom may be replaced with a sulfur atom in the ligated product).

In some embodiments, a synthetic nucleic acid duplex can be assembled via chemical ligation in a one step reaction involving simultaneous chemical ligation of nucleic acids on both strands of the duplex. For example, a mixture of 5'-phosphorylated oligonucleotides corresponding to both strands of a target nucleic acid may be chemically ligated by a) exposure to heat (e.g., to 97° C.) and slow cooling to form a complex of annealed oligonucleotides, and b) exposure to cyanogen bromide or any other suitable coupling agent under conditions sufficient to chemically ligate adjacent 3' and 5' ends in the nucleic acid complex.

In some embodiments, a synthetic nucleic acid duplex can be assembled via chemical ligation in a two step reaction involving separate chemical ligations for the complementary strands of the duplex. For example, each strand of a target nucleic acid may be ligated in a separate reaction containing phosphorylated oligonucleotides corresponding to the strand that is to be ligated and non-phosphorylated oligonucleotides corresponding to the complementary strand. The non-phosphorylated oligonucleotides may serve as a template for the phosphorylated oligonucleotides during a chemical ligation (e.g. using cyanogen bromide). The resulting single-stranded ligated nucleic acid may be purified and annealed to a complementary ligated single-stranded nucleic acid to form the target duplex nucleic acid (see, for example, Shabarova Z A et al., 1991, Nuc. Acids Res. 19:4247-51).

Aspects of the invention may be used to enhance different types of nucleic acid assembly reactions (e.g., multiplex nucleic acid assembly reactions). Aspects of the invention may be used in combination with one or more assembly reactions described in, for example, Carr et al., 2004, Nucleic Acids Research, Vol. 32, No 20, e162 (9 pages); Richmond et al., 2004, Nucleic Acids Research, Vol. 32, No 17, pp. 5011-5018; Caruthers et al., 1972, J. Mol. Biol. 72, 475-492; Hecker et al., 1998, Biotechniques 24:256-260; Kodumal et al., 2004, PNAS Vol. 101, No. 44, pp. 15573-15578; Tian et al., 2004, Nature, Vol. 432, pp. 1050-1054; and U.S. Pat. Nos. 6,008,031 and 5,922,539, the disclosures of which are incorporated herein by reference. Certain embodiments of multiplex nucleic acid assembly reactions for generating a predetermined nucleic acid fragment are illustrated with reference to FIGS. 1-4. It should be appreciated that synthesis and assembly methods described herein (including, for example, oligonucleotide synthesis, multiplex nucleic acid assembly, concerted assembly of nucleic acid fragments, or any combination thereof) may be performed in any suitable format, including in a reaction tube, in a multi-well plate, on a surface, on a column, in a microfluidic device (e.g., a microfluidic tube), a capillary tube, etc.

FIG. 1 shows one embodiment of a plurality of oligonucleotides that may be assembled in a polymerase-based multiplex oligonucleotide assembly reaction. FIG. 1A shows two groups of oligonucleotides (Group P and Group N) that have sequences of portions of the two complementary strands of a nucleic acid fragment to be assembled. Group P includes oligonucleotides with positive strand sequences ($P_1, P_2, \ldots P_{n-1}, P_n, P_{n+1}, P_T$, shown from 5'→3' on the positive strand). Group N includes oligonucleotides with negative strand sequences ($N_T, \ldots, N_{n+1}, N_n, N_{n-1}, \ldots, N_2, N_1$, shown from 5'→3' on the negative strand). In this example, none of the P group oligonucleotides overlap with each other and none of the N group oligonucleotides overlap with each other. However, in some embodiments, one or more of the oligonucleotides within the S or N group may overlap. Furthermore, FIG. 1A shows gaps between consecutive oligonucleotides in Group P and gaps between consecutive oligonucleotides in Group N. However, each P group oligonucleotide (except for $P_1$) and each N group oligonucleotide (except for $N_T$) overlaps with complementary regions of two oligonucleotides from the complementary group of oligonucleotides. $P_1$ and $N_T$ overlap with a complementary region of only one oligonucleotide from the other group (the complementary 3'-most oligonucleotides $N_1$ and $P_T$, respectively). FIG. 1B shows a structure of an embodiment of a Group P or Group N oligonucleotide represented in FIG. 1A. This oligonucleotide includes a 5' region that is complementary to a 5' region of a first oligonucleotide from the other group, a 3' region that is complementary to a 3' region of a second oligonucleotide from the other group, and a core or central region that is not complementary to any oligonucleotide sequence from the other group (or its own group). This central region is illustrated as the B region in FIG. 1B. The sequence of the B region may be different for each different oligonucleotide. As defined herein, the B region of an oligonucleotide in one group corresponds to a gap between two consecutive oligonucleotides in the complementary group of oligonucleotides. It should be noted that the 5'-most oligonucleotide in each group ($P_1$ in Group P and $N_T$ in Group N) does not have a 5' region that is complementary to the 5' region of any other oligonucleotide in either group. Accordingly, the 5'-most oligonucleotides ($P_1$ and $N_T$) that are illustrated in FIG. 1A each have a 3' complementary region and a 5' non-complementary region (the B region of FIG. 1B), but no 5' complementary region. However, it should be appreciated that any one or more of the oligonucleotides in Group P and/or Group N (including all of the oligonucleotides in Group P and/or Group N) can be designed to have no B region. In the absence of a B region, a 5'-most oligonucleotide has only the 3' complementary region (meaning that the entire oligonucleotide is complementary to the 3' region of the 3'-most oligonucleotide from the other group (e.g., the 3' region of $N_1$ or $P_T$ shown in FIG. 1A). In the absence of a B region, one of the other oligonucleotides in either Group P or Group N has only a 5' complementary region and a 3' complementary region (meaning that the entire oligonucleotide is complementary to the 5' and 3' sequence regions of the two overlapping oligonucleotides from the complementary group). In some embodiments, only a subset of oligonucleotides in an assembly reaction may include B regions. It should be appreciated that the length of the 5', 3', and B regions may be different for each oligonucleotide. However, for each oligonucleotide the length of the 5' region is the same as the length of the complementary 5' region in the 5' overlapping oligonucleotide from the other group. Similarly, the length of the 3' region is the same as the length of the complementary 3' region in the 3' overlapping oligonucleotide from the other group. However, in certain embodiments a 3'-most oligonucleotide may be designed with a 3' region that extends beyond the 5' region of the 5'-most oligonucleotide. In this embodiment, an assembled product may include the 5' end of the 5'-most oligonucleotide, but not the 3' end of the 3'-most oligonucleotide that extends beyond it.

Figure 1C:
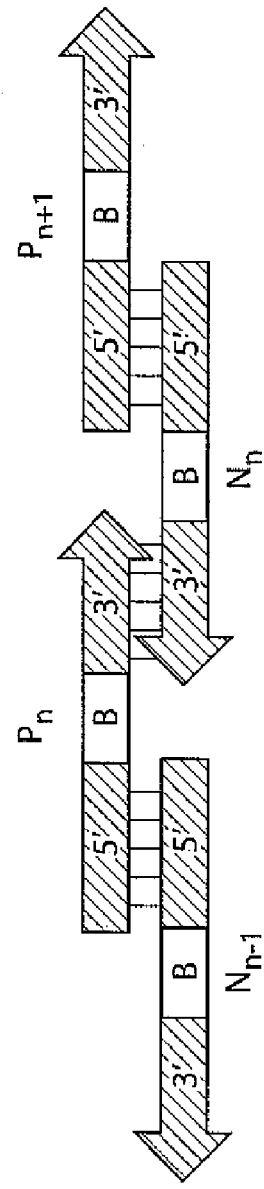

FIG. 1C illustrates a subset of the oligonucleotides from FIG. 1A, each oligonucleotide having a 5', a 3', and an optional B region. Oligonucleotide $P_n$ is shown with a 5' region that is complementary to (and can anneal to) the 5' region of oligonucleotide $N_{n-1}$. Oligonucleotide $P_n$ also has a 3' region that is complementary to (and can anneal to) the 3' region of oligonucleotide $N_n$. $N_n$ is also shown with a 5' region that is complementary (and can anneal to) the 5' region of oligonucleotide $P_{n+1}$. This pattern could be repeated for all of oligonucleotides $P_2$ to $P_T$ and $N_1$ to $N_{T-1}$ (with the 5'-most oligonucleotides only having 3' complementary regions as discussed herein). If all of the oligonucleotides from Group P and Group N are mixed together under appropriate hybridization conditions, they may anneal to form a long chain such as the oligonucleotide complex illustrated in FIG. 1A. However, subsets of the oligonucleotides may form shorter chains and even oligonucleotide dimers with annealed 5' or 3' regions. It should be appreciated that many copies of each oligonucleotide are included in a typical reaction mixture. Accordingly, the resulting hybridized reaction mixture may contain a distribution of different oligonucleotide dimers and complexes. Polymerase-mediated extension of the hybridized oligonucleotides results in a template-based extension of the 3' ends of oligonucleotides that have annealed 3' regions. Accordingly, polymerase-mediated extension of the oligonucleotides shown in FIG. 1C would result in extension of the 3' ends only of oligonucleotides $P_n$ and $N_n$ generating extended oligonucleotides containing sequences that are complementary to all the regions of $N_n$ and $P_n$, respectively. Extended oligonucleotide products with sequences complementary to all of $N_{n-1}$ and $P_{n+1}$ would not be generated unless oligonucleotides $P_{n-1}$ and $N_{n+1}$ were included in the reaction mixture. Accordingly, if all of the oligonucleotide sequences in a plurality of oligonucleotides are to be incorporated into an assembled nucleic acid fragment using a polymerase, the plurality of oligonucleotides should include 5'-most oligonucleotides that are at least complementary to the entire 3' regions of the 3'-most oligonucleotides. In some embodiments, the 5'-most oligonucleotides also may have 5' regions that extend beyond the 3' ends of the 3'-most oligonucleotides as illustrated in FIG. 1A. In some embodiments, a ligase also may be added to ligate adjacent 5' and 3' ends that may be formed upon 3' extension of annealed oligonucleotides in an oligonucleotide complex such as the one illustrated in FIG. 1A.

When assembling a nucleic acid fragment using a polymerase, a single cycle of polymerase extension extends oligonucleotide pairs with annealed 3' regions. Accordingly, if a plurality of oligonucleotides were annealed to form an annealed complex such as the one illustrated in FIG. 1A, a single cycle of polymerase extension would result in the extension of the 3' ends of the $P_1/N_1$, $P_2/N_2$, ..., $P_{n-1}/N_{n-1}$, $P_n/N_n$, $P_{n+1}/N_{n+1}$, ..., $P_T/N_T$ oligonucleotide pairs. In one embodiment, a single molecule could be generated by ligating the extended oligonucleotide dimers. In one embodiment, a single molecule incorporating all of the oligonucleotide sequences may be generated by performing several polymerase extension cycles.

Figure 1D:
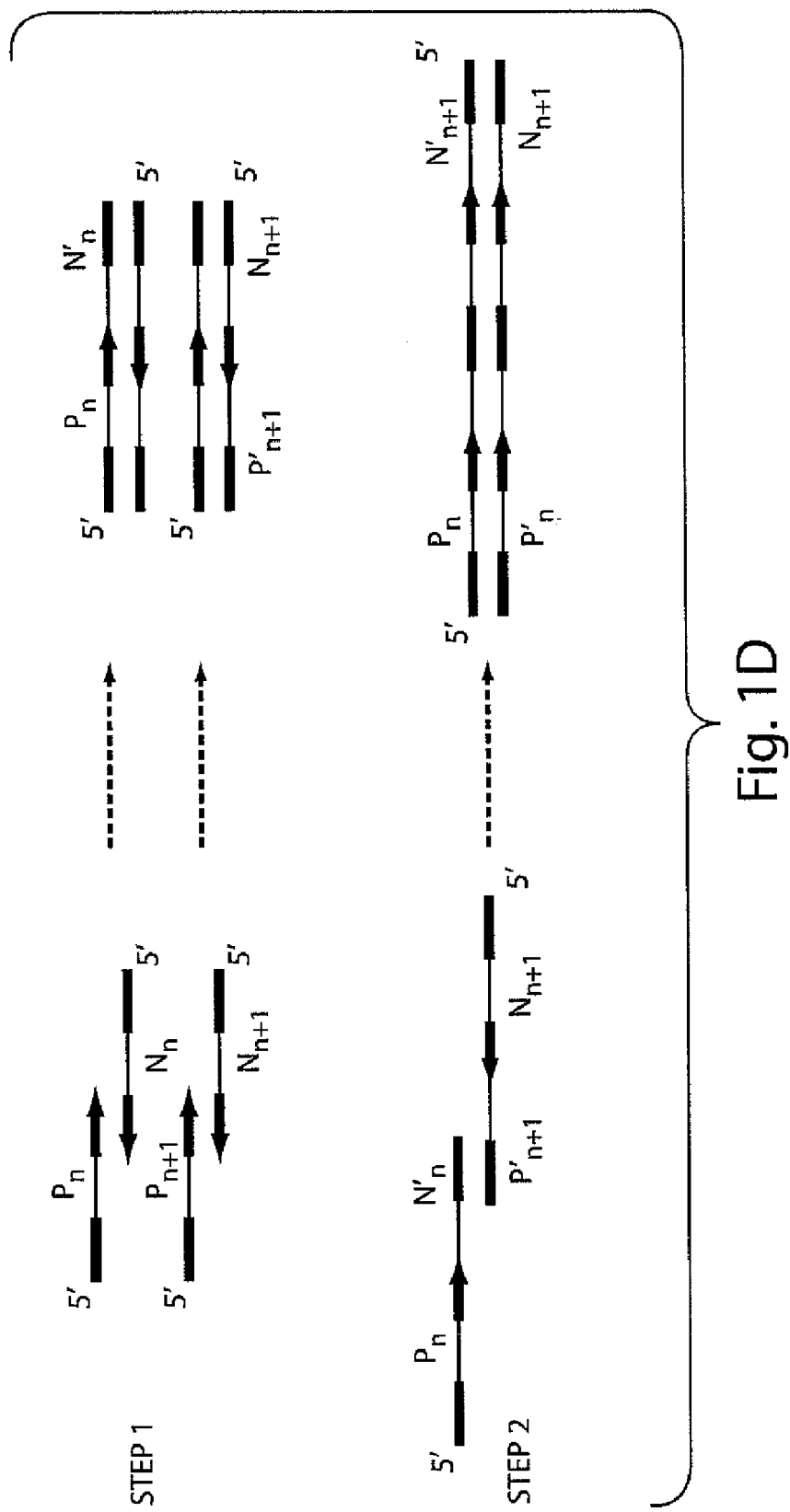

In one embodiment, FIG. 1D illustrates two cycles of polymerase extension (separated by a denaturing step and an annealing step) and the resulting nucleic acid products. It should be appreciated that several cycles of polymerase extension may be required to assemble a single nucleic acid fragment containing all the sequences of an initial plurality of oligonucleotides. In one embodiment, a minimal number of extension cycles for assembling a nucleic acid may be calculated as $\log_2 n$, where n is the number of oligonucleotides being assembled. In some embodiments, progressive assembly of the nucleic acid may be achieved without using temperature cycles. For example, an enzyme capable of rolling circle amplification may be used (e.g., phi 29 polymerase) when a circularized nucleic acid (e.g., oligonucleotide) complex is used as a template to produce a large amount of circular product for subsequent processing using MutS or a MutS homolog as described herein. In step 1 of FIG. 1D, annealed oligonucleotide pairs $P_n/N_n$ and $P_{n+1}/N_{n+1}$ are extended to form oligonucleotide dimer products incorporating the sequences covered by the respective oligonucleotide pairs. For example, $P_n$ is extended to incorporate sequences that are complementary to the B and 5' regions of $N_n$ (indicated as $N'_n$ in FIG. 1D). Similarly, $N_{n+1}$ is extended to incorporate sequences that are complementary to the 5' and B regions of $P_{n+1}$ (indicated as $P'_{n+1}$ in FIG. 1D). These dimer products may be denatured and reannealed to form the starting material of step 2 where the 3' end of the extended $P_n$ oligonucleotide is annealed to the 3' end of the extended $N_{n+1}$ oligonucleotide. This product may be extended in a polymerase-mediated reaction to form a product that incorporates the sequences of the four oligonucleotides ($P_n$, $N_n$, $P_{n+1}$, $N_{n+1}$). One strand of this extended product has a sequence that includes (in 5' to 3' order) the 5', B, and 3' regions of $P_n$, the complement of the B region of $N_n$, the 5', B, and 3' regions of $P_{n+1}$ and the complements of the B and 5' regions of $N_{n+1}$. The other strand of this extended product has the complementary sequence. It should be appreciated that the 3' regions of $P_n$ and $N_n$ are complementary, the 5' regions of $N_n$ and $P_{n+1}$ are complementary, and the 3' regions of $P_{n+1}$ and $N_{n+1}$ are complementary. It also should be appreciated that the reaction products shown in FIG. 1D are a subset of the reaction products that would be obtained using all of the oligonucleotides of Group P and Group N. A first polymerase extension reaction using all of the oligonucleotides would result in a plurality of overlapping oligonucleotide dimers from $P_1/N_1$ to $P_T/N_T$. Each of these may be denatured and at least one of the strands could then anneal to an overlapping complementary strand from an adjacent (either 3' or 5') oligonucleotide dimer and be extended in a second cycle of polymerase extension as shown in FIG. 1D. Subsequent cycles of denaturing, annealing, and extension produce progressively larger products including a nucleic acid fragment that includes the sequences of all of the initial oligonucleotides. It should be appreciated that these subsequent rounds of extension also produce many nucleic acid products of intermediate length. The reaction product may be complex since not all of the 3' regions may be extended in each cycle. Accordingly, unextended oligonucleotides may be available in each cycle to anneal to other unextended oligonucleotides or to previously extended oligonucleotides. Similarly, extended products of different sizes may anneal to each other in each cycle. Accordingly, a mixture of extended products of different sizes covering different regions of the sequence may be generated along with the nucleic acid fragment covering the entire sequence. This mixture also may contain any remaining unextended oligonucleotides.

FIG. 2 shows an embodiment of a plurality of oligonucleotides that may be assembled in a directional polymerase-based multiplex oligonucleotide assembly reaction. In this embodiment, only the 5'-most oligonucleotide of Group P may be provided. In contrast to the example shown in FIG. 1, the remainder of the sequence of the predetermined nucleic acid fragment is provided by oligonucleotides of Group N. The 3'-most oligonucleotide of Group N(N1) has a 3' region that is complementary to the 3' region of $P_1$ as shown in FIG. 2B. However, the remainder of the oligonucleotides in Group N have overlapping (but non-complementary) 3' and 5' regions as illustrated in FIG. 2B for oligonucleotides N1-N3. Each Group N oligonucleotide (e.g., $N_n$) overlaps with two adjacent oligonucleotides: one overlaps with the 3' region ($N_{n-1}$) and one with the 5' region ($N_{n+1}$), except for $N_1$ that overlaps with the 3' regions of $P_1$ (complementary overlap) and N2 (non-complementary overlap), and NT that overlaps only with $N_{T-1}$. It should be appreciated that all of the overlaps shown in FIG. 2A between adjacent oligonucleotides $N_2$ to $N_{T-1}$ are non-complementary overlaps between the 5' region of one oligonucleotide and the 3' region of the adjacent oligonucleotide illustrated in a 3' to 5' direction on the N strand of the predetermined nucleic acid fragment. It also should be appreciated that each oligonucleotide may have 3', B, and 5' regions of different lengths (including no B region in some embodiments). In some embodiments, none of the oligonucleotides may have B regions, meaning that the entire sequence of each oligonucleotide may overlap with the combined 5' and 3' region sequences of its two adjacent oligonucleotides.

Figure 2A:
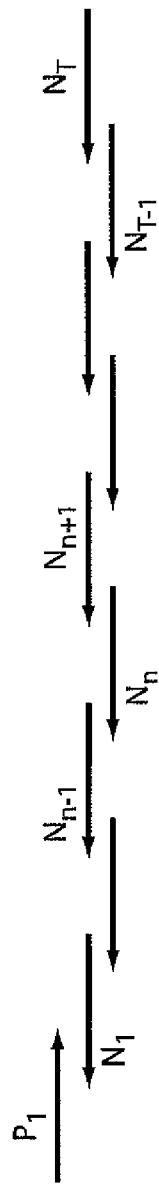
FIG. 2 illustrates certain aspects of an embodiment of sequential assembly of a plurality of oligonucleotides in a polymerase-based multiplex assembly reaction.
Figure 2B:
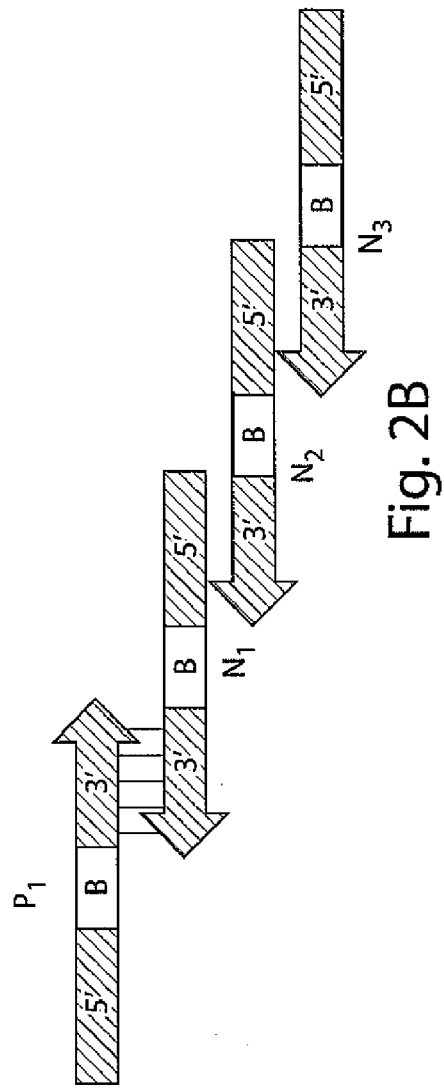
Figure 2C:
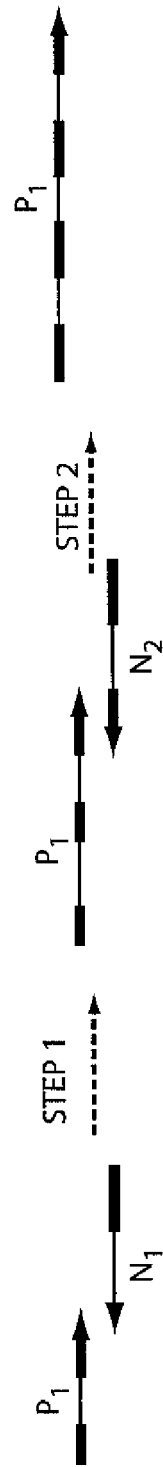

Assembly of a predetermined nucleic acid fragment from the plurality of oligonucleotides shown in FIG. 2A may involve multiple cycles of polymerase-mediated extension. Each extension cycle may be separated by a denaturing and an annealing step. FIG. 2C illustrates the first two steps in this assembly process. In step 1, annealed oligonucleotides $P_1$ and $N_1$ are extended to form an oligonucleotide dimer. $P_1$ is shown with a 5' region that is non-complementary to the 3' region of $N_1$ and extends beyond the 3' region of $N_1$ when the oligonucleotides are annealed. However, in some embodiments, $P_1$ may lack the 5' non-complementary region and include only sequences that overlap with the 3' region of $N_1$. The product of $P_1$ extension is shown after step 1 containing an extended region that is complementary to the 5' end of $N_1$. The single strand illustrated in FIG. 2C may be obtained by denaturing the oligonucleotide dimer that results from the extension of $P_1/N_1$ in step 1. The product of $P_1$ extension is shown annealed to the 3' region of $N_2$. This annealed complex may be extended in step 2 to generate an extended product that now includes sequences complementary to the B and 5' regions of $N_2$. Again, the single strand illustrated in FIG. 2C may be obtained by denaturing the oligonucleotide dimer that results from the extension reaction of step 2. Additional cycles of extension may be performed to further assemble a predetermined nucleic acid fragment. In each cycle, extension results in the addition of sequences complementary to the B and 5' regions of the next Group N oligonucleotide. Each cycle may include a denaturing and annealing step. However, the extension may occur under the annealing conditions. Accordingly, in one embodiment, cycles of extension may be obtained by alternating between denaturing conditions (e.g., a denaturing temperature) and annealing/extension conditions (e.g., an annealing/extension temperature). In one embodiment, T (the number of group N oligonucleotides) may determine the minimal number of temperature cycles used to assemble the oligonucleotides. However, in some embodiments, progressive extension may be achieved without temperature cycling. For example, an enzyme capable promoting rolling circle amplification may be used (e.g., TempliPhi). It should be appreciated that a reaction mixture containing an assembled predetermined nucleic acid fragment also may contain a distribution of shorter extension products that may result from incomplete extension during one or more of the cycles or may be the result of an $P_1/N_1$ extension that was initiated after the first cycle.

FIG. 2D illustrates an example of a sequential extension reaction where the 5'-most $P_1$ oligonucleotide is bound to a support and the Group N oligonucleotides are unbound. The reaction steps are similar to those described for FIG. 2C. However, an extended predetermined nucleic acid fragment will be bound to the support via the 5'-most $P_1$ oligonucleotide. Accordingly, the complementary strand (the negative strand) may readily be obtained by denaturing the bound fragment and releasing the negative strand. In some embodiments, the attachment to the support may be labile or readily reversed (e.g., using light, a chemical reagent, a pH change, etc.) and the positive strand also may be released. Accordingly, either the positive strand, the negative strand, or the double-stranded product may be obtained. FIG. 2E illustrates an example of a sequential reaction where $P_1$ is unbound and the Group N oligonucleotides are bound to a support. The reaction steps are similar to those described for FIG. 2C. However, an extended predetermined nucleic acid fragment will be bound to the support via the 5'-most $N_T$ oligonucleotide. Accordingly, the complementary strand (the positive strand) may readily be obtained by denaturing the bound fragment and releasing the positive strand. In some embodiments, the attachment to the support may be labile or readily reversed (e.g., using light, a chemical reagent, a pH change, etc.) and the negative strand also may be released. Accordingly, either the positive strand, the negative strand, or the double-stranded product may be obtained.

Figure 2F:
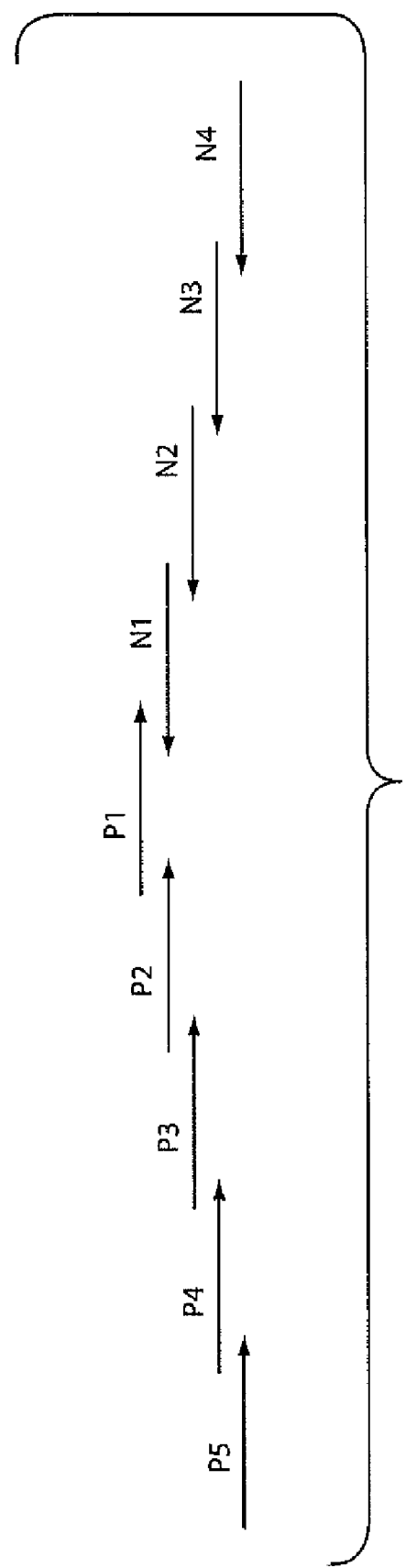

It should be appreciated that other configurations of oligonucleotides may be used to assemble a nucleic acid via two or more cycles of polymerase-based extension. In many configurations, at least one pair of oligonucleotides have complementary 3' end regions. FIG. 2F illustrates an example where an oligonucleotide pair with complementary 3' end regions is flanked on either side by a series of oligonucleotides with overlapping non-complementary sequences. The oligonucleotides illustrated to the right of the complementary pair have overlapping 3' and 5' regions (with the 3' region of one oligonucleotide being identical to the 5' region of the adjacent oligonucleotide) that corresponding to a sequence of one strand of the target nucleic acid to be assembled. The oligonucleotides illustrated to the left of the complementary pair have overlapping 3' and 5' regions (with the 3' region of one oligonucleotide being identical to the 5' region of the adjacent oligonucleotide) that correspond to a sequence of the complementary strand of the target nucleic acid. These oligonucleotides may be assembled via sequential polymerase-based extension reactions as described herein (see also, for example, Xiong et al., 2004, Nucleic Acids Research, Vol. 32, No. 12, e98, 10 pages, the disclosure of which is incorporated by reference herein). It should be appreciated that different numbers and/or lengths of oligonucleotides may be used on either side of the complementary pair. Accordingly, the illustration of the complementary pair as the central pair in FIG. 2F is not intended to be limiting as other configuration of a complementary oligonucleotide pair flanked by a different number of non-complementary pairs on either side may be used according to methods of the invention.

FIG. 3 shows an embodiment of a plurality of oligonucleotides that may be assembled in a ligase reaction. FIG. 3A illustrates the alignment of the oligonucleotides showing that they do not contain gaps (i.e., no B region as described herein). Accordingly, the oligonucleotides may anneal to form a complex with no nucleotide gaps between the 3' and 5' ends of the annealed oligonucleotides in either Group P or Group N. These oligonucleotides provide a suitable template for assembly using a ligase under appropriate reaction conditions. However, it should be appreciated that these oligonucleotides also may be assembled using a polymerase-based assembly reaction as described herein. FIG. 3B shows two individual ligation reactions. These reactions are illustrated in two steps. However, it should be appreciated that these ligation reactions may occur simultaneously or sequentially in any order and may occur as such in a reaction maintained under constant reaction conditions (e.g., with no temperature cycling) or in a reaction exposed to several temperature cycles. For example, the reaction illustrated in step 2 may occur before the reaction illustrated in step 1. In each ligation reaction illustrated in FIG. 3B, a Group N oligonucleotide is annealed to two adjacent Group P oligonucleotides (due to the complementary 5' and 3' regions between the P and N oligonucleotides), providing a template for ligation of the adjacent P oligonucleotides. Although not illustrated, ligation of the N group oligonucleotides also may proceed in similar manner to assemble adjacent N oligonucleotides that are annealed to their complementary P oligonucleotide. Assembly of the predetermined nucleic acid fragment may be obtained through ligation of all of the oligonucleotides to generate a double stranded product. However, in some embodiments, a single stranded product of either the positive or negative strand may be obtained. In certain embodiments, a plurality of oligonucleotides may be designed to generate only single-stranded reaction products in a ligation reaction. For example, a first group of oligonucleotides (of either Group P or Group N) may be provided to cover the entire sequence on one strand of the predetermined nucleic acid fragment (on either the positive or negative strand). In contrast, a second group of oligonucleotides (from the complementary group to the first group) may be designed to be long enough to anneal to complementary regions in the first group but not long enough to provide adjacent 5' and 3' ends between oligonucleotides in the second group. This provides substrates that are suitable for ligation of oligonucleotides from the first group but not the second group. The result is a single-stranded product having a sequence corresponding to the oligonucleotides in the first group. Again, as with other assembly reactions described herein, a ligase reaction mixture that contains an assembled predetermined nucleic acid fragment also may contain a distribution of smaller fragments resulting from the assembly of a subset of the oligonucleotides.

FIG. 4 shows an embodiment of a ligase-based assembly where one or more of the plurality of oligonucleotides is bound to a support. In FIG. 4A, the 5' most oligonucleotide of the P group oligonucleotides is bound to a support. Ligation of adjacent oligonucleotides in the 5' to 3' direction results in the assembly of a predetermined nucleic acid fragment. FIG. 4A illustrates an example where adjacent oligonucleotides $P_2$ and $P_3$ are added sequentially. However, the ligation of any two adjacent oligonucleotides from Group P may occur independently and in any order in a ligation reaction mixture. For example, when $P_1$ is ligated to the 5' end of $N_2$, $N_2$ may be in the form of a single oligonucleotide or it already may be ligated to one or more downstream oligonucleotides ($N_3$, $N_4$, etc.). It should be appreciated that for a ligation assembly bound to a support, either the 5'-most (e.g., $P_1$ for Group P, or $N_T$ for Group N) or the 3'-most (e.g., $P_T$ for Group P, or $N_1$ for Group N) oligonucleotide may be bound to a support since the reaction can proceed in any direction. In some embodiments, a predetermined nucleic acid fragment may be assembled with a central oligonucleotide (i.e., neither the 5'-most or the 3'-most) that is bound to a support provided that the attachment to the support does not interfere with ligation.

FIG. 4B illustrates an example where a plurality of N group oligonucleotides are bound to a support and a predetermined nucleic acid fragment is assembled from P group oligonucleotides that anneal to their complementary support-bound N group oligonucleotides. Again, FIG. 4B illustrates a sequential addition. However, adjacent P group oligonucleotides may be ligated in any order. Also, the bound oligonucleotides may be attached at their 5' end, 3' end, or at any other position provided that the attachment does not interfere with their ability to bind to complementary 5' and 3' regions on the oligonucleotides that are being assembled. This reaction may involve one or more reaction condition changes (e.g., temperature cycles) so that ligated oligonucleotides bound to one immobilized N group oligonucleotide can be dissociated from the support and bind to a different immobilized N group oligonucleotide to provide a substrate for ligation to another P group oligonucleotide.

As with other assembly reactions described herein, support-bound ligase reactions (e.g., those illustrated in FIG. 4B) that generate a full length predetermined nucleic acid fragment also may generate a distribution of smaller fragments resulting from the assembly of subsets of the oligonucleotides. A support used in any of the assembly reactions described herein (e.g., polymerase-based, ligase-based, or other assembly reaction) may include any suitable support medium. A support may be solid, porous, a matrix, a gel, beads, beads in a gel, etc. A support may be of any suitable size. A solid support may be provided in any suitable configuration or shape (e.g., a chip, a bead, a gel, a microfluidic channel, a planar surface, a spherical shape, a column, etc.).

As illustrated herein, different oligonucleotide assembly reactions may be used to assemble a plurality of overlapping oligonucleotides (with overlaps that are either 5'/5', 3'/3', 5'/3', complementary, non-complementary, or a combination thereof). Many of these reactions include at least one pair of oligonucleotides (the pair including one oligonucleotide from a first group or P group of oligonucleotides and one oligonucleotide from a second group or N group of oligonucleotides) have overlapping complementary 3' regions. However, in some embodiments, a predetermined nucleic acid may be assembled from non-overlapping oligonucleotides using blunt-ended ligation reactions. In some embodiments, the order of assembly of the non-overlapping oligonucleotides may be biased by selective phosphorylation of different 5' ends. In some embodiments, size purification may be used to select for the correct order of assembly. In some embodiments, the correct order of assembly may be promoted by sequentially adding appropriate oligonucleotide substrates into the reaction (e.g., the ligation reaction).

In order to obtain a full-length nucleic acid fragment from a multiplex oligonucleotide assembly reaction, a purification step may be used to remove starting oligonucleotides and/or incompletely assembled fragments. In some embodiments, a purification step may involve chromatography, electrophoresis, or other physical size separation technique. In certain embodiments, a purification step may involve amplifying the full length product. For example, a pair of amplification primers (e.g., PCR primers) that correspond to the predetermined 5' and 3' ends of the nucleic acid fragment being assembled will preferentially amplify full length product in an exponential fashion. It should be appreciated that smaller assembled products may be amplified if they contain the predetermined 5' and 3' ends. However, such smaller-than-expected products containing the predetermined 5' and 3' ends should only be generated if an error occurred during assembly (e.g., resulting in the deletion or omission of one or more regions of the target nucleic acid) and may be removed by size fractionation of the amplified product. Accordingly, a preparation containing a relatively high amount of full length product may be obtained directly by amplifying the product of an assembly reaction using primers that correspond to the predetermined 5' and 3' ends. In some embodiments, additional purification (e.g., size selection) techniques may be used to obtain a more purified preparation of amplified full-length nucleic acid fragment.

When designing a plurality of oligonucleotides to assemble a predetermined nucleic acid fragment, the sequence of the predetermined fragment will be provided by the oligonucleotides as described herein. However, the oligonucleotides may contain additional sequence information that may be removed during assembly or may be provided to assist in subsequent manipulations of the assembled nucleic acid fragment. Examples of additional sequences include, but are not limited to, primer recognition sequences for amplification (e.g., PCR primer recognition sequences), restriction enzyme recognition sequences, recombination sequences, other binding or recognition sequences, labeled sequences, etc. In some embodiments, one or more of the 5'-most oligonucleotides, one or more of the 3'-most oligonucleotides, or any combination thereof, may contain one or more additional sequences. In some embodiments, the additional sequence information may be contained in two or more adjacent oligonucleotides on either strand of the predetermined nucleic acid sequence. Accordingly, an assembled nucleic acid fragment may contain additional sequences that may be used to connect the assembled fragment to one or more additional nucleic acid fragments (e.g., one or more other assembled fragments, fragments obtained from other sources, vectors, etc.) via ligation, recombination, polymerase-mediated assembly, etc. In some embodiments, purification may involve cloning one or more assembled nucleic acid fragments. The cloned product may be screened (e.g., sequenced, analyzed for an insert of the expected size, etc.).

In some embodiments, a nucleic acid fragment assembled from a plurality of oligonucleotides may be combined with one or more additional nucleic acid fragments using a polymerase-based and/or a ligase-based extension reaction similar to those described herein for oligonucleotide assembly. Accordingly, one or more overlapping nucleic acid fragments may be combined and assembled to produce a larger nucleic acid fragment as described herein. In certain embodiments, double-stranded overlapping oligonucleotide fragments may be combined. However, single-stranded fragments, or combinations of single-stranded and double-stranded fragments may be combined as described herein. A nucleic acid fragment assembled from a plurality of oligonucleotides may be of any length depending on the number and length of the oligonucleotides used in the assembly reaction. For example, a nucleic acid fragment (either single-stranded or double-stranded) assembled from a plurality of oligonucleotides may be between 50 and 1,000 nucleotides long (for example, about 70 nucleotides long, between 100 and 500 nucleotides long, between 200 and 400 nucleotides long, about 200 nucleotides long, about 300 nucleotides long, about 400 nucleotides long, etc.). One or more such nucleic acid fragments (e.g., with overlapping 3' and/or 5' ends) may be assembled to form a larger nucleic acid fragment (single-stranded or double-stranded) as described herein.

A full length product assembled from smaller nucleic acid fragments also may be isolated or purified as described herein (e.g., using a size selection, cloning, selective binding or other suitable purification procedure). In addition, any assembled nucleic acid fragment (e.g., full-length nucleic acid fragment) described herein may be amplified (prior to, as part of, or after, a purification procedure) using appropriate 5' and 3' amplification primers.

Synthetic Oligonucleotides:

It should be appreciated that the terms P Group and N Group oligonucleotides are used herein for clarity purposes only, and to illustrate several embodiments of multiplex oligonucleotide assembly. The Group P and Group N oligonucleotides described herein are interchangeable, and may be referred to as first and second groups of oligonucleotides corresponding to sequences on complementary strands of a target nucleic acid fragment.

Oligonucleotides may be synthesized using any suitable technique. For example, oligonucleotides may be synthesized on a column or other support (e.g., a chip). Examples of chip-based synthesis techniques include techniques used in synthesis devices or methods available from Combimatrix, Agilent, Affymetrix, or other sources. A synthetic oligonucleotide may be of any suitable size, for example between 10 and 1,000 nucleotides long (e.g., between 10 and 200, 200 and 500, 500 and 1,000 nucleotides long, or any combination thereof). An assembly reaction may include a plurality of oligonucleotides, each of which independently may be between 10 and 200 nucleotides in length (e.g., between 20 and 150, between 30 and 100, 30 to 90, 30-80, 30-70, 30-60, 35-55, 40-50, or any intermediate number of nucleotides). However, one or more shorter or longer oligonucleotides may be used in certain embodiments.

Oligonucleotides may be provided as single stranded synthetic products. However, in some embodiments, oligonucleotides may be provided as double-stranded preparations including an annealed complementary strand. Oligonucleotides may be molecules of DNA, RNA, PNA, or any combination thereof. A double-stranded oligonucleotide may be produced by amplifying a single-stranded synthetic oligonucleotide or other suitable template (e.g., a sequence in a nucleic acid preparation such as a nucleic acid vector or genomic nucleic acid). Accordingly, a plurality of oligonucleotides designed to have the sequence features described herein may be provided as a plurality of single-stranded oligonucleotides having those feature, or also may be provided along with complementary oligonucleotides. In some embodiments, an oligonucleotide may be phosphorylated (e.g., with a 5' phosphate). In some embodiments, an oligonucleotide may be non-phosphorylated.

In some embodiments, an oligonucleotide may be amplified using an appropriate primer pair with one primer corresponding to each end of the oligonucleotide (e.g., one that is complementary to the 3' end of the oligonucleotide and one that is identical to the 5' end of the oligonucleotide). In some embodiments, an oligonucleotide may be designed to contain a central assembly sequence (designed to be incorporated into the target nucleic acid) flanked by a 5' amplification sequence (e.g., a 5' universal sequence) and a 3' amplification sequence (e.g., a 3' universal sequence). Amplification primers (e.g., between 10 and 50 nucleotides long, between 15 and 45 nucleotides long, about 25 nucleotides long, etc.) corresponding to the flanking amplification sequences may be used to amplify the oligonucleotide (e.g., one primer may be complementary to the 3' amplification sequence and one primer may have the same sequence as the 5' amplification sequence). The amplification sequences then may be removed from the amplified oligonucleotide using any suitable technique to produce an oligonucleotide that contains only the assembly sequence.

In some embodiments, a plurality of different oligonucleotides (e.g., about 5, 10, 50, 100, or more) with different central assembly sequences may have identical 5' amplification sequences and identical 3' amplification sequences. These oligonucleotides can all be amplified in the same reaction using the same amplification primers.

A preparation of an oligonucleotide designed to have a certain sequence may include oligonucleotide molecules having the designed sequence in addition to oligonucleotide molecules that contain errors (e.g., that differ from the designed sequence at least at one position). A sequence error may include one or more nucleotide deletions, additions, substitutions (e.g., transversion or transition), inversions, duplications, or any combination of two or more thereof. Oligonucleotide errors may be generated during oligonucleotide synthesis. Different synthetic techniques may be prone to different error profiles and frequencies. In some embodiments, error rates may vary from 1/10 to 1/200 errors per base depending on the synthesis protocol that is used. However, in some embodiments lower error rates may be achieved. Also, the types of errors may depend on the synthetic techniques that are used. For example, in some embodiments chip-based oligonucleotide synthesis may result in relatively more deletions than column-based synthetic techniques.

In some embodiments, one or more oligonucleotide preparations may be processed to remove (or reduce the frequency of) error-containing oligonucleotides. In some embodiments, a hybridization technique may be used wherein an oligonucleotide preparation is hybridized under stringent conditions one or more times to an immobilized oligonucleotide preparation designed to have a complementary sequence. Oligonucleotides that do not bind may be removed in order to selectively or specifically remove oligonucleotides that contain errors that would destabilize hybridization under the conditions used. It should be appreciated that this processing may not remove all error-containing oligonucleotides since many have only one or two sequence errors and may still bind to the immobilized oligonucleotides with sufficient affinity for a fraction of them to remain bound through this selection processing procedure.

In some embodiments, a nucleic acid binding protein or recombinase (e.g., RecA) may be included in one or more of the oligonucleotide processing steps to improve the selection of error free oligonucleotides. For example, by preferentially promoting the hybridization of oligonucleotides that are completely complementary with the immobilized oligonucleotides, the amount of error containing oligonucleotides that are bound may be reduced. As a result, this oligonucleotide processing procedure may remove more error-containing oligonucleotides and generate an oligonucleotide preparation that has a lower error frequency (e.g., with an error rate of less than 1/50, less than 1/100, less than 1/200, less than 1/300, less than 1/400, less than 1/500, less than 1/1,000, or less than 1/2,000 errors per base.

A plurality of oligonucleotides used in an assembly reaction may contain preparations of synthetic oligonucleotides, single-stranded oligonucleotides, double-stranded oligonucleotides, amplification products, oligonucleotides that are processed to remove (or reduce the frequency of) error-containing variants, etc., or any combination of two or more thereof.

In some aspects, synthetic oligonucleotides synthesized on an array (e.g., a chip) are not amplified prior to assembly. In some embodiments, a polymerase-based or ligase-based assembly using non-amplified oligonucleotides may be performed in a microfluidic device.

In some aspects, a synthetic oligonucleotide may be amplified prior to use. Either strand of a double-stranded amplification product may be used as an assembly oligonucleotide and added to an assembly reaction as described herein. A synthetic oligonucleotide may be amplified using a pair of amplification primers (e.g., a first primer that hybridizes to the 3' region of the oligonucleotide and a second primer that hybridizes to the 3' region of the complement of the oligonucleotide). The oligonucleotide may be synthesized on a support such as a chip (e.g., using an ink-jet-based synthesis technology). In some embodiments, the oligonucleotide may be amplified while it is still attached to the support. In some embodiments, the oligonucleotide may be removed or cleaved from the support prior to amplification. The two strands of a double-stranded amplification product may be separated and isolated using any suitable technique. In some embodiments, the two strands may be differentially labeled (e.g., using one or more different molecular weight, affinity, fluorescent, electrostatic, magnetic, and/or other suitable tags). The different labels may be used to purify and/or isolate one or both strands. In some embodiments, biotin may be used as a purification tag. In some embodiments, the strand that is to be used for assembly may be directly purified (e.g., using an affinity or other suitable tag). In some embodiments, the complementary strand is removed (e.g., using an affinity or other suitable tag) and the remaining strand is used for assembly.

In some embodiments, a synthetic oligonucleotide may include a central assembly sequence flanked by 5' and 3' amplification sequences. The central assembly sequence is designed for incorporation into an assembled nucleic acid. The flanking sequences are designed for amplification and are not intended to be incorporated into the assembled nucleic acid. The flanking amplification sequences may be used as universal primer sequences to amplify a plurality of different assembly oligonucleotides that share the same amplification sequences but have different central assembly sequences. In some embodiments, the flanking sequences are removed after amplification to produce an oligonucleotide that contains only the assembly sequence.

In some embodiments, one of the two amplification primers may be biotinylated. The nucleic acid strand that incorporates this biotinylated primer during amplification can be affinity purified using streptavidin (e.g., bound to a bead, column, or other surface). In some embodiments, the amplification primers also may be designed to include certain sequence features that can be used to remove the primer regions after amplification in order to produce a single-stranded assembly oligonucleotide that includes the assembly sequence without the flanking amplification sequences.

In some embodiments, the non-biotinylated strand may be used for assembly. The assembly oligonucleotide may be purified by removing the biotinylated complementary strand. In some embodiments, the amplification sequences may be removed if the non-biotinylated primer includes a dU at its 3' end, and if the amplification sequence recognized by (i.e., complementary to) the biotinylated primer includes at most three of the four nucleotides and the fourth nucleotide is present in the assembly sequence at (or adjacent to) the junction between the amplification sequence and the assembly sequence. After amplification, the double-stranded product is incubated with T4 DNA polymerase (or other polymerase having a suitable editing activity) in the presence of the fourth nucleotide (without any of the nucleotides that are present in the amplification sequence recognized by the biotinylated primer) under appropriate reaction conditions. Under these conditions, the 3' nucleotides are progressively removed through to the nucleotide that is not present in the amplification sequence (referred to as the fourth nucleotide above). As a result, the amplification sequence that is recognized by the biotinylated primer is removed. The biotinylated strand is then removed. The remaining non-biotinylated strand is then treated with uracil-DNA glycosylase (UDG) to remove the non-biotinylated primer sequence. This technique generates a single-stranded assembly oligonucleotide without the flanking amplification sequences. It should be appreciated that this technique may be used to process a single amplified oligonucleotide preparation or a plurality of different amplified oligonucleotides in a single reaction if they share the same amplification sequence features described above.

In some embodiments, the biotinylated strand may be used for assembly. The assembly oligonucleotide may be obtained directly by isolating the biotinylated strand. In some embodiments, the amplification sequences may be removed if the biotinylated primer includes a dU at its 3' end, and if the amplification sequence recognized by (i.e., complementary to) the non-biotinylated primer includes at most three of the four nucleotides and the fourth nucleotide is present in the assembly sequence at (or adjacent to) the junction between the amplification sequence and the assembly sequence. After amplification, the double-stranded product is incubated with T4 DNA polymerase (or other polymerase having a suitable editing activity) in the presence of the fourth nucleotide (without any of the nucleotides that are present in the amplification sequence recognized by the non-biotinylated primer) under appropriate reaction conditions. Under these conditions, the 3' nucleotides are progressively removed through to the nucleotide that is not present in the amplification sequence (referred to as the fourth nucleotide above). As a result, the amplification sequence that is recognized by the non-biotinylated primer is removed. The biotinylated strand is then isolated (and the non-biotinylated strand is removed). The isolated biotinylated strand is then treated with UDG to remove the biotinylated primer sequence. This technique generates a single-stranded assembly oligonucleotide without the flanking amplification sequences. It should be appreciated that this technique may be used to process a single amplified oligonucleotide preparation or a plurality of different amplified oligonucleotides in a single reaction if they share the same amplification sequence features described above.

It should be appreciated that the biotinylated primer may be designed to anneal to either the synthetic oligonucleotide or to its complement for the amplification and purification reactions described above. Similarly, the non-biotinylated primer may be designed to anneal to either strand provided it anneals to the strand that is complementary to the strand recognized by the biotinylated primer.

In certain embodiments, it may be helpful to include one or more modified oligonucleotides in an assembly reaction. An oligonucleotide may be modified by incorporating a modified-base (e.g., a nucleotide analog) during synthesis, by modifying the oligonucleotide after synthesis, or any combination thereof. Examples of modifications include, but are not limited to, one or more of the following: universal bases such as nitroindoles, dP and dK, inosine, uracil; halogenated bases such as BrdU; fluorescent labeled bases; non-radioactive labels such as biotin (as a derivative of dT) and digoxigenin (DIG); 2,4-Dinitrophenyl (DNP); radioactive nucleotides; post-coupling modification such as dR-$NH_2$ (deoxyribose-$NH_2$); Acridine (6-chloro-2-methoxiacridine); and spacer phosphoramides which are used during synthesis to add a spacer 'arm' into the sequence, such as C3, C8 (octanediol), C9, C12, HEG (hexaethlene glycol) and C18.

It should be appreciated that one or more nucleic acid binding proteins or recombinases are preferably not included in a post-assembly fidelity optimization technique (e.g., a screening technique using a MutS or MutS homolog), because the optimization procedure involves removing error-containing nucleic acids via the production and removal of heteroduplexes. Accordingly, any nucleic acid binding proteins or recombinases (e.g., RecA) that were included in the assembly steps are preferably removed (e.g., by inactivation, column purification or other suitable technique) after assembly and prior to fidelity optimization.

Applications:

Aspects of the invention may be useful for a range of applications involving the production and/or use of synthetic nucleic acids. As described herein, the invention provides methods for assembling synthetic nucleic acids with increased efficiency. The resulting assembled nucleic acids may be amplified in vitro (e.g., using PCR, LCR, or any suitable amplification technique), amplified in vivo (e.g., via cloning into a suitable vector), isolated and/or purified. An assembled nucleic acid (alone or cloned into a vector) may be transformed into a host cell (e.g., a prokaryotic, eukaryotic, insect, mammalian, or other host cell). In some embodiments, the host cell may be used to propagate the nucleic acid. In certain embodiments, the nucleic acid may be integrated into the genome of the host cell. In some embodiments, the nucleic acid may replace a corresponding nucleic acid region on the genome of the cell (e.g., via homologous recombination). Accordingly, nucleic acids may be used to produce recombinant organisms. In some embodiments, a target nucleic acid may be an entire genome or large fragments of a genome that are used to replace all or part of the genome of a host organism. Recombinant organisms also may be used for a variety of research, industrial, agricultural, and/or medical applications.

Many of the techniques described herein can be used together, applying combinations of one or more extension-based and/or ligation-based assembly techniques at one or more points to produce long nucleic acid molecules. For example, concerted assembly may be used to assemble oligonucleotide duplexes and nucleic acid fragments of less than 100 to more than 10,000 base pairs in length (e.g., 100 mers to 500 mers, 500 mers to 1,000 mers, 1,000 mers to 5,000 mers, 5,000 mers to 10,000 mers, 25,000 mers, 50,000 mers, 75,000 mers, 100,000 mers, etc.). In an exemplary embodiment, methods described herein may be used during the assembly of an entire genome (or a large fragment thereof, e.g., about 10%, 20%, 30%, 40%, 50%, 60%, 70%, 80%, 90%, or more) of an organism (e.g., of a viral, bacterial, yeast, or other prokaryotic or eukaryotic organism), optionally incorporating specific modifications into the sequence at one or more desired locations.

Any of the nucleic acid products (e.g., including nucleic acids that are amplified, cloned, purified, isolated, etc.) may be packaged in any suitable format (e.g., in a stable buffer, lyophilized, etc.) for storage and/or shipping (e.g., for shipping to a distribution center or to a customer). Similarly, any of the host cells (e.g., cells transformed with a vector or having a modified genome) may be prepared in a suitable buffer for storage and or transport (e.g., for distribution to a customer). In some embodiments, cells may be frozen. However, other stable cell preparations also may be used.

Host cells may be grown and expanded in culture. Host cells may be used for expressing one or more RNAs or polypeptides of interest (e.g., therapeutic, industrial, agricultural, and/or medical proteins). The expressed polypeptides may be natural polypeptides or non-natural polypeptides. The polypeptides may be isolated or purified for subsequent use.

Accordingly, nucleic acid molecules generated using methods of the invention can be incorporated into a vector. The vector may be a cloning vector or an expression vector. A vector may comprise an origin of replication and one or more selectable markers (e.g., antibiotic resistant markers, auxotrophic markers, etc.). In some embodiments, the vector may be a viral vector. A viral vector may comprise nucleic acid sequences capable of infecting target cells. Similarly, in some embodiments, a prokaryotic expression vector operably linked to an appropriate promoter system can be used to transform target cells. In other embodiments, a eukaryotic vector operably linked to an appropriate promoter system can be used to transfect target cells or tissues.

Transcription and/or translation of the constructs described herein may be carried out in vitro (i.e., using cell-free systems) or in vivo (i.e., expressed in cells). In some embodiments, cell lysates may be prepared. In certain embodiments, expressed RNAs or polypeptides may be isolated or purified. Nucleic acids of the invention also may be used to add detection and/or purification tags to expressed polypeptides or fragments thereof. Examples of polypeptide-based fusion/tag include, but are not limited to, hexa-histidine ($His^6$) Myc and HA, and other polypeptides with utility, such as GFP, GST, MBP, chitin and the like. In some embodiments, polypeptides may comprise one or more unnatural amino acid residue(s).

In some embodiments, antibodies can be made against polypeptides or fragment(s) thereof encoded by one or more synthetic nucleic acids.

In certain embodiments, synthetic nucleic acids may be provided as libraries for screening in research and development (e.g., to identify potential therapeutic proteins or peptides, to identify potential protein targets for drug development, etc.)

In some embodiments, a synthetic nucleic acid may be used as a therapeutic (e.g., for gene therapy, or for gene regulation). For example, a synthetic nucleic acid may be administered to a patient in an amount sufficient to express a therapeutic amount of a protein. In other embodiments, a synthetic nucleic acid may be administered to a patient in an amount sufficient to regulate (e.g., down-regulate) the expression of a gene.

It should be appreciated that different acts or embodiments described herein may be performed independently and may be performed at different locations in the United States or outside the United States. For example, each of the acts of receiving an order for a target nucleic acid, analyzing a target nucleic acid sequence, identifying an assembly strategy, designing one or more starting nucleic acids (e.g., oligonucleotides), synthesizing starting nucleic acid(s), purifying starting nucleic acid(s), assembling starting nucleic acid(s), isolating assembled nucleic acid(s), confirming the sequence of assembled nucleic acid(s), manipulating assembled nucleic acid(s) (e.g., amplifying, cloning, inserting into a host genome, etc.), and any other acts or any parts of these acts may be performed independently either at one location or at different sites within the United States or outside the United States. In some embodiments, an assembly procedure may involve a combination of acts that are performed at one site (in the United States or outside the United States) and acts that are performed at one or more remote sites (within the United States or outside the United States).

Automated Applications:

Aspects of the invention may include automating one or more acts described herein. For example, a sequence analysis may be automated in order to generate a synthesis strategy automatically. The synthesis strategy may include i) the design of the starting nucleic acids that are to be assembled into the target nucleic acid, ii) the choice of the assembly technique(s) to be used, iii) the number of rounds of assembly and error screening or sequencing steps to include, and/or decisions relating to subsequent processing of an assembled target nucleic acid. Similarly, one or more steps of an assembly reaction may be automated using one or more automated sample handling devices (e.g., one or more automated liquid or fluid handling devices). For example, the synthesis and optional selection of starting nucleic acids (e.g., oligonucleotides) may be automated using a nucleic acid synthesizer and automated procedures. Automated devices and procedures may be used to mix reaction reagents, including one or more of the following: starting nucleic acids, buffers, enzymes (e.g., one or more ligases and/or polymerases), nucleotides, nucleic acid binding proteins or recombinases, salts, and any other suitable agents such as stabilizing agents. In some embodiments, reaction reagents may include one or more reagents or reaction conditions suitable for extension-based assembly, ligation-based assembly, or combinations thereof. Automated devices and procedures also may be used to control the reaction conditions. For example, an automated thermal cycler may be used to control reaction temperatures and any temperature cycles that may be used. In some embodiments, a thermal cycler may be automated to provide one or more reaction temperatures or temperature cycles suitable for incubating nucleic acid fragments prior to transformation. Similarly, subsequent purification and analysis of assembled nucleic acid products may be automated. For example, fidelity optimization steps (e.g., a MutS error screening procedure) may be automated using appropriate sample processing devices and associated protocols. Sequencing also may be automated using a sequencing device and automated sequencing protocols. Additional steps (e.g., amplification, cloning, etc.) also may be automated using one or more appropriate devices and related protocols. It should be appreciated that one or more of the device or device components described herein may be combined in a system (e.g., a robotic system). Assembly reaction mixtures (e.g., liquid reaction samples) may be transferred from one component of the system to another using automated devices and procedures (e.g., robotic manipulation and/or transfer of samples and/or sample containers, including automated pipetting devices, etc.). The system and any components thereof may be controlled by a control system.

Accordingly, acts of the invention may be automated using, for example, a computer system (e.g., a computer controlled system). A computer system on which aspects of the invention can be implemented may include a computer for any type of processing (e.g., sequence analysis and/or automated device control as described herein). However, it should be appreciated that certain processing steps may be provided by one or more of the automated devices that are part of the assembly system. In some embodiments, a computer system may include two or more computers. For example, one computer may be coupled, via a network, to a second computer. One computer may perform sequence analysis. The second computer may control one or more of the automated synthesis and assembly devices in the system. In other aspects, additional computers may be included in the network to control one or more of the analysis or processing acts. Each computer may include a memory and processor. The computers can take any form, as the aspects of the present invention are not limited to being implemented on any particular computer platform. Similarly, the network can take any form, including a private network or a public network (e.g., the Internet). Display devices can be associated with one or more of the devices and computers. Alternatively, or in addition, a display device may be located at a remote site and connected for displaying the output of an analysis in accordance with the invention. Connections between the different components of the system may be via wire, wireless transmission, satellite transmission, any other suitable transmission, or any combination of two or more of the above.

In accordance with one embodiment of the present invention for use on a computer system it is contemplated that sequence information (e.g., a target sequence, a processed analysis of the target sequence, etc.) can be obtained and then sent over a public network, such as the Internet, to a remote location to be processed by computer to produce any of the various types of outputs discussed herein (e.g., in connection with oligonucleotide design). However, it should be appreciated that the aspects of the present invention described herein are not limited in that respect, and that numerous other configurations are possible. For example, all of the analysis and processing described herein can alternatively be implemented on a computer that is attached locally to a device, an assembly system, or one or more components of an assembly system. As a further alternative, as opposed to transmitting sequence information (e.g., a target sequence, a processed analysis of the target sequence, etc.) over a communication medium (e.g., the network), the information can be loaded onto a computer readable medium that can then be physically transported to another computer for processing in the manners described herein. In another embodiment, a combination of two or more transmission/delivery techniques may be used. It also should be appreciated that computer implementable programs for performing a sequence analysis or controlling one or more of the devices, systems, or system components described herein also may be transmitted via a network or loaded onto a computer readable medium as described herein. Accordingly, aspects of the invention may involve performing one or more steps within the United States and additional steps outside the United States. In some embodiments, sequence information (e.g., a customer order) may be received at one location (e.g., in one country) and sent to a remote location for processing (e.g., in the same country or in a different country), for example, for sequence analysis to determine a synthesis strategy and/or design oligonucleotides. In certain embodiments, a portion of the sequence analysis may be performed at one site (e.g., in one country) and another portion at another site (e.g., in the same country or in another country). In some embodiments, different steps in the sequence analysis may be performed at multiple sites (e.g., all in one country or in several different countries). The results of a sequence analysis then may be sent to a further site for synthesis. However, in some embodiments, different synthesis and quality control steps may be performed at more than one site (e.g., within one county or in two or more countries). An assembled nucleic acid then may be shipped to a further site (e.g., either to a central shipping center or directly to a client).

Each of the different aspects, embodiments, or acts of the present invention described herein can be independently automated and implemented in any of numerous ways. For example, each aspect, embodiment, or act can be independently implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of the embodiments of the present invention comprises at least one computer-readable medium (e.g., a computer memory, a floppy disk, a compact disk, a tape, etc.) encoded with a computer program (i.e., a plurality of instructions), which, when executed on a processor, performs one or more of the above-discussed functions of the present invention. The computer-readable medium can be transportable such that the program stored thereon can be loaded onto any computer system resource to implement one or more functions of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that can be employed to program a processor to implement the above-discussed aspects of the present invention.

It should be appreciated that in accordance with several embodiments of the present invention wherein processes are implemented in a computer readable medium, the computer implemented processes may, during the course of their execution, receive input manually (e.g., from a user).

Accordingly, overall system-level control of the assembly devices or components described herein may be performed by a system controller which may provide control signals to the associated nucleic acid synthesizers, liquid handling devices, thermal cyclers, sequencing devices, associated robotic components, as well as other suitable systems for performing the desired input/output or other control functions. Thus, the system controller along with any device controllers together form a controller that controls the operation of a nucleic acid assembly system. The controller may include a general purpose data processing system, which can be a general purpose computer, or network of general purpose computers, and other associated devices, including communications devices, modems, and/or other circuitry or components necessary to perform the desired input/output or other functions. The controller can also be implemented, at least in part, as a single special purpose integrated circuit (e.g., ASIC) or an array of ASICs, each having a main or central processor section for overall, system-level control, and separate sections dedicated to performing various different specific computations, functions and other processes under the control of the central processor section. The controller can also be implemented using a plurality of separate dedicated programmable integrated or other electronic circuits or devices, e.g., hard wired electronic or logic circuits such as discrete element circuits or programmable logic devices. The controller can also include any other components or devices, such as user input/output devices (monitors, displays, printers, a keyboard, a user pointing device, touch screen, or other user interface, etc.), data storage devices, drive motors, linkages, valve controllers, robotic devices, vacuum and other pumps, pressure sensors, detectors, power supplies, pulse sources, communication devices or other electronic circuitry or components, and so on. The controller also may control operation of other portions of a system, such as automated client order processing, quality control, packaging, shipping, billing, etc., to perform other suitable functions known in the art but not described in detail herein.

Business Applications:

Aspects of the invention may be useful to streamline nucleic acid assembly reactions. Accordingly, aspects of the invention relate to marketing methods, compositions, kits, devices, and systems for increasing nucleic acid assembly throughput involving combinations of one or more extension-based and/or ligation-based assembly techniques described herein.

Aspects of the invention may be useful for reducing the time and/or cost of production, commercialization, and/or development of synthetic nucleic acids, and/or related compositions. Accordingly, aspects of the invention relate to business methods that involve collaboratively (e.g., with a partner) or independently marketing one or more methods, kits, compositions, devices, or systems for analyzing and/or assembling synthetic nucleic acids as described herein. For example, certain embodiments of the invention may involve marketing a procedure and/or associated devices or systems involving nucleic acid assembly techniques described herein. In some embodiments, synthetic nucleic acids, libraries of synthetic nucleic acids, host cells containing synthetic nucleic acids, expressed polypeptides or proteins, etc., also may be marketed.

Marketing may involve providing information and/or samples relating to methods, kits, compositions, devices, and/or systems described herein. Potential customers or partners may be, for example, companies in the pharmaceutical, biotechnology and agricultural industries, as well as academic centers and government research organizations or institutes. Business applications also may involve generating revenue through sales and/or licenses of methods, kits, compositions, devices, and/or systems of the invention.

EXAMPLES

Example 1

Nucleic Acid Fragment Assembly

Gene assembly via a 2-step PCR method: In step (1), a primerless assembly of oligonucleotides is performed and in step (2) an assembled nucleic acid fragment is amplified in a primer-based amplification.

A 993 base long promoter>EGFP construct was assembled from 50-mer abutting oligonucleotides using a 2-step PCR assembly.

Mixed oligonucleotide pools were prepared as follows: 36 overlapping 50-mer oligonucleotides and two 5' terminal 59-mers were separated into 4 pools, each corresponding to overlapping 200-300 nucleotide segments of the final construct. The total oligonucleotide concentration in each pool was 5 µM.

A primerless PCR extension reaction was used to stitch (assemble) overlapping oligonucleotides in each pool. The PCR extension reaction mixture was as follows:

| | |
|---|---|
| oligonucleotide pool (5 µM total) | 1.0 µl (~25 nM final each) |
| dNTP (10 mM each) | 0.5 µl (250 µM final each) |
| Pfu buffer (10x) | 2.0 µl |
| Pfu polymerase (2.5 U/µl) | 0.5 µl |
| dH$_2$O to 20 µl | |

Assembly was achieved by cycling this mixture through several rounds of denaturing, annealing, and extension reactions as follows:
start 2 min. 95° C.
30 cycles of 95° C. 30 sec., 65° C. 30 sec., 72° C. 1 min.
final 72° C. 2 min. extension step The resulting product was exposed to amplification conditions to amplify the desired nucleic acid fragments (sub-segments of 200-300 nucleotides). The following PCR mix was used:

| | |
|---|---|
| primerless PCR product | 1.0 µl |
| primer 5' (1.2 µM) | 5 µl (300 nM final) |
| primer 3' (1.2 µM) | 5 µl (300 nM final) |
| dNTP (10 mM each) | 0.5 µl (250 µM final each) |
| Pfu buffer (10x) | 2.0 µl |
| Pfu polymerase (2.5 U/µl) | 0.5 µl |
| dH$_2$O to 20 µl | |

The following PCR cycle conditions were used:
start 2 min. 95° C.
35 cycles of 95° C. 30 sec., 65° C. 30 sec., 72° C. 1 min.
final 72° C. 2 min. extension step The amplified sub-segments were assembled using another round of primerless PCR as follows. A diluted amplification product was prepared for each sub-segment by diluting each amplified sub-segment PCR product 1:10 (4 µl mix+36 µl dH$_2$O). This diluted mix was used as follows:

| | |
|---|---|
| diluted sub-segment mix | 1.0 µl |
| dNTP (10 mM each) | 0.5 µl (250 µM final each) |
| Pfu buffer (10x) | 2.0 µl |
| Pfu polymerase (2.5 U/µl) | 0.5 µl |
| dH₂O to 20 µl | |

The following PCR cycle conditions were used:
start 2 min. 95° C.
30 cycles of 95° C. 30 sec., 65° C. 30 sec., 72° C. 1 min.
final 72° C. 2 min. extension step The full-length 993 nucleotide long promoter>EGFP was amplified in the following PCR mix:

| | |
|---|---|
| assembled sub-segments | 1.0 µl |
| primer 5' (1.2 µM) | 5 µl (300 nM final) |
| primer 3' (1.2 µM) | 5 µl (300 nM final) |
| dNTP (10 mM each) | 0.5 µl (250 µM final each) |
| Pfu buffer (10x) | 2.0 µl |
| Pfu polymerase (2.5 U/µl) | 0.5 µl |
| dH₂O to 20 µl | |

The following PCR cycle conditions were used:
start 2 min. 95° C.
35 cycles of 95° C. 30 sec., 65° C. 30 sec., 72° C. 1 min.
final 72° C. 2 min. extension step Example 2

General Protocol

In this example, an assembly cycle using activation of one or more vector-encoded traits to isolate correctly assembled constructs will involve the following steps.

1—DNA preparation;
2—Digestion of insert DNA (e.g., at alternating sites 1, 3 and 2, 4 as described for FIGS. 6-8);
3—Paired ligation of 1-3 cut fragments with 2-4 cut fragments together with vector DNA;
4—Transformation of host cells with ligation reaction mixture;
5—Recovery growth of the transformed cells in SOC (1-2h); and
6—Transfer of the transformed cell culture to selective liquid media for growth in suspension (10-15 h).

This protocol selects for correctly-ligated insert DNA to propagate, removing any background or contaminating vector DNA. This enables an automated, 'hands-off' assembly scheme that eliminates colony grow-up during the assembly phase. This process may involve approximately $\log_2 N$ assembly steps where N is the total number of fragments to be combined (e.g., building a 50 kb final construct from 50 sequence-verified 1 kb fragments would involve six steps).

Due to stringent selection for correctly-ligated insert DNA in the transformed host cell culture, this process will not require colony isolation and grow-up, thereby decreasing assembly time. For example, assuming that each step could be completed in one day, construction of a 50 kb construct from 50 sequence-verified 1 kb segments would take six days. One additional day would be required for assembly of a 100 kb construct from 100 sequence-verified 1 kb segments.

This protocol may be automated (e.g., using a microfluidic device).

Example 3

Automation

In this example of an automated assembly scheme, the following steps will be automated.
1—Transfer of enzyme mix (1, 3 or 2, 4) to prepped DNA;
2-Temperature-controlled incubation for digest followed by heat inactivation (e.g., on a block);
3—Mixing of 1, 3 and 2, 4 digests;
4—Transfer of 1, 4-linearized vector and ligase to digest mix;
5—Cell transformation;
6—Suspension growth in selective media; and
7—Automated DNA prep (e.g., CosMC prep on Biomek FX).
One or more of these steps may be automated on a microfluidic device.

Example 4

Methods and Use of Assembly by Marker Activation

Figure 10:
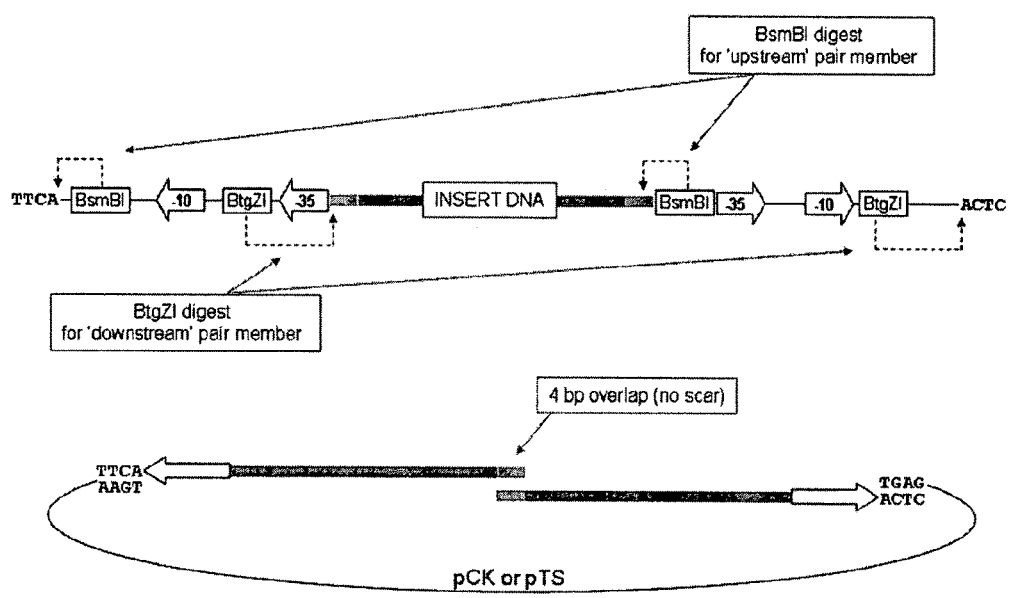
FIG. 10 illustrates a non-limiting embodiment depicting a Pairwise Selection Assembly (PSA) procedure.

Assembly by marker activation (referred to operationally as pairwise selection assembly (PSA)) was used in the construction of large fragments. In this example, this approach was used to construct a 22 kb fragment (target product) from ~400 bp starting fragments. In this process, individually cloned DNA sequences (or linear fragments produced from an amplification or assembly process) contain ~65 bp activation tags at both termini. These tags are short DNA sequences necessary for the activation of non-functional antibiotic resistance markers present on the target vector. In one example, both tags incorporate promoter regions necessary for the activation of two independent non-functional markers on the target vector. Two fragments to be combined are digested such that only one tag would be retained for each fragment. After ligation with vector, selection based on the two activated markers yields correctly-ligated insert DNA. This process is repeated, switching between two vectors with different markers, until the desired DNA sequence has been constructed. The process is shown schematically in FIG. 10.

PSA vectors constructed for use in the assembly process contain a functional ampicillin resistance marker and two non-functional resistance markers. These vectors are illustrated in FIG. 11. These non-functional resistance markers are either chloramphenical and kanamycin (pCK) or tetracycline and specintomycin (pTS) (see FIG. 11). pCK and pTS vectors have been constructed such that they contain either a high-copy number origin of replication, or a BAC-based single-copy number origin of replication. The former versions enable DNA assembly up to ~10 kb (although we have successfully assembled up to 22 kb), while the latter BAC-based vectors enable construction up to ~300 kb. Transition from one vector type to another is seamless, as both vector types have the same non-functional markers that are activated by the same activation tags (i.e., they differ only in the origin of replication).

Following the protocol presented below, it was demonstrated that: (1) selection of correct ligation products in vivo, obviating the need for individual clone purification through colony isolation; (2) assembly of unpurified PCR products containing activation tags; (3) assembly from cloned fragments flanked by activation tags; and (4) sequence-independent assembly where internal restriction sites are blocked from digestion via site methylation. The use of methyl-sensitive restriction enzymes and RecA-mediated site-blocking enables the assembly of DNA molecules without the need for modification (e.g., to remove restriction sites).

An example of a PSA process flow chart used for the experiment is as follows:

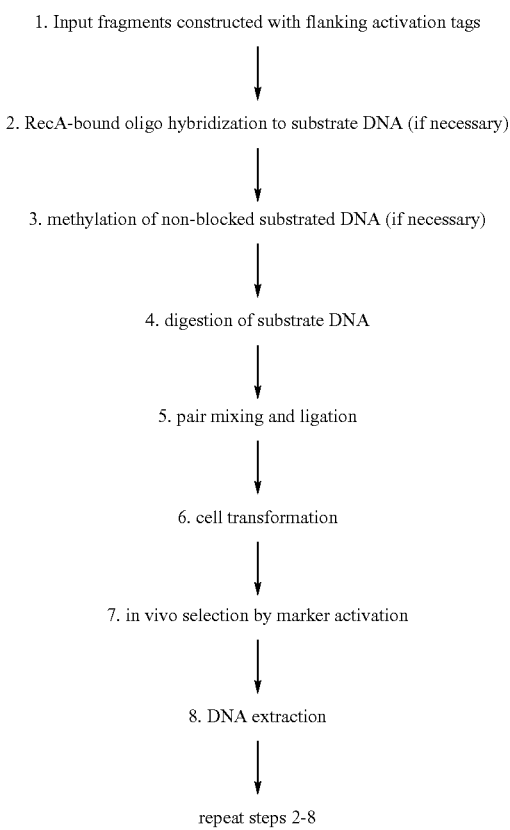

1. Input fragments constructed with flanking activation tags
2. RecA-bound oligo hybridization to substrate DNA (if necessary)
3. methylation of non-blocked substrated DNA (if necessary)
4. digestion of substrate DNA
5. pair mixing and ligation
6. cell transformation
7. in vivo selection by marker activation
8. DNA extraction repeat steps 2-8

An example of a PSA protocol is summarized below. All steps outlined below occurred after DNA preparation and concentration normalization (50 ng/μl). It should be noted that Steps I-III apply only to constructs that require blocking ('L' fragments with internal BsmBI sites or 'R' fragments with internal BtgZI sites). The specific blocking oligonucleotides used in the experiment are listed at the end of this protocol.

Step I. Polymerize Blocking Oligos with RecA

| Materials: | 1 μM L oligo mix (ctp, ktd - retains left activation tag) |
| | 1 μM R oligo mix (ctd, ktp - retains right activation tag) |
| | RecA (NEB, 2 μg/μl) |
| | NEB2 (NEB, 10x) |
| | 10 mM ATPγS (Sigma A1388) |

| Reaction Component | | Amount (μl) | Notes |
|---|---|---|---|
| oligo mix | 1 μM | 4 | 240 pmol nucleotides |
| NEB2 | 10x | 1.5 | |
| RecA | 2 μg/μl | 1.5 | 80 pmol RecA |
| dH₂O | | 7 | |
| ATPγS | 10 mM | 1 | 0.66 mM ATPγS |
| Incubate at 37° C. 10-20 min | | 15.0 μl | 3:1 nucleotides:RecA |

Step II. Substrate Addition, Synapsis

| Reaction Component | | Amount (μl) | Notes |
|---|---|---|---|
| plasmid | 50 ng/μl | 9 | 450 ng |
| NEB2 | 10x | 1 | |
| Incubate at 37° C. 30 min | | 10 μl | 0.4 mM ATPγS |

Step III. Substrate Methylation

| Materials: | SssI methyltransferase (NEB, 20 units/μl) |
| | SAM (NEB, 32 mM) |

It should be noted that ratio of methyl-donor, e.g., S-adenosylmethionine (SAM), to methyl-acceptor (2xCpG sites on substrate) should be taken into account at this step. If random nucleotide composition assumed, then reaction conditions indicated below would yield >60-fold excess methyl-donor for most insert sizes >1 kb.

| Reaction Component | | Amount (μl) | Notes |
|---|---|---|---|
| SssI | 20 units/μl | 0.5 | |
| SAM | 32 mM | 0.1 | 3200 pmol SAM |
| NEB2 | 10x | 0.5 | |
| dH₂O | | 3.9 | |
| Incubate at 37° C. 2 h | | 5.0 μl | |
| Heat inactivation at 60° C. 25 min | | | |

Step IV Digestion (Note: all Constructs that DO NOT Require Blocking Start at this Step.)

| Materials: | BsmBI (NEB, 10 units/μl) for L fragments; dilute 1:10 to 1 unit/μl |
| | BtgZI (NEB, 2 units/μl) for R fragments |

For constructs that DO NOT require blocking:

| Reaction Component | | Amount (μl) | Notes |
|---|---|---|---|
| plasmid | 50 ng/μl | 9 | |
| NEB2 | 10x | 3 | |
| enzyme | | 1 | BsmBI (L) or BtgZI (R) |
| dH₂O | | 17 | |
| Incubate at 55° C. 50 min | | 30 μl | |
| Heat inactivation at 85° C. 25 min | | | |

For constructs that require blocking, 1 unit BsmBI to 'L' fragments only (1 μl of 1:10 dilution of stock 10 units/μl) and 2 units BtgZI to 'R' fragments only (1 μl of stock 2 units/μl) was directly added to the 30 μl blocking reaction; subsequently, the reaction was incubate as indicated above (55° C. 50 min>>85° C. 25 min).

Step V. Ligation

| Materials: | T4 DNA ligase (NEB, 400,000 units/µl) |
|---|---|

The digested sample was diluted 1:2 (add 30 µl dH₂O).

| Reaction Component | Amount (µl) | Notes |
|---|---|---|
| vector 40 ng/µl | 1.0 | |
| 'L' digestion 7.5 ng/µl | 6 | |
| 'R' digestion 7.5 ng/µl | 6 | |
| T4 buffer 10x | 1.5 | |
| T4 ligase 400 units/µl | 0.5 | |
| Incubate at RT 45 min | 15.0 µl | |

Step VI. Transformation

Transform competent DH10B (or similar strain—must be sensitive to cam, kan, tc, and spn, and must be deficient in *E. coli* mcr, mrr restriction systems). Standard transformation protocols were followed (e.g., add 3 µl ligation reaction to 50 µl competent cells, heat shock 30 sec at 42° C., recover in 350 µl SOC 1 hr at 37° C., 250 rpm).

Following the transformation, the resulting culture was diluted 1:50 in selective media and was grown overnight at 37° C., with shaking at ~300 rpm. Subsequently, ~200 µl of the culture was plated on selective plates and grown overnight at 37° C. For selection, appropriate antibiotics were added as follows: for pTS vector, 5 µg/ml Tc and 100 µg/ml Spn were added; for pCK vector, 12.5 µg/ml Cam and 25 µg/ml Kan were added.

The following table provides the sequences of blocking oligonucleotides that can be used in this protocol in combination with activation sequences illustrated in FIG. 12.

ctp-60 [SEQ ID NO:1]
5'-CATGAGACGATCTCCTTCCTCTTGATGGCTGTAATAATAGCTCTAG
GGCGATGTTAAGAC-3' ctd-60 [SEQ ID NO:2]
5'-GTCTTAACATCGCCCTAGAGCTATTATTACAGCCATCAAGAGGAAG
GAGATCGTCTCATG-3' ktd-60 [SEQ ID NO:3]
5'-GGAGACGTTGACAACATGAAGTAAACAGCGTAAGATGTACCACATG
AAATTGCGATGAGG-3' ktp-60 [SEQ ID NO:4]
5'-CATAGATTTCCTCATCGCAATTTCATGTGGTACATCTTACGCTGTT
TACTTCATGTTGTC-3'

In FIG. 12, the left activation sequence contains BsmBI and BtgZI sites (corresponding to sites 1 and 2 described herein, respectively) within a modified promoter region. Similarly, the right activation sequence contains BsmBI and BtgZI sites (corresponding to sites 3 and 4 described herein, respectively) within a modified promoter region. Sequences represented by "iii . . . " represent the insert specific sequences. The left TTCA and the right ACTC overhangs are compatible with overhangs on the vector that is being used. It should be appreciated that a single blocking oligonucleotide (e.g., ctp-60 or ctd-60) may be used to block the left sequence from methylation. Similarly, a single oligonucleotide (e.g., ktd-60 or ktp-60) may be used to block the right sequence from methylation.

EQUIVALENTS

The present invention provides among other things methods for assembling large polynucleotide constructs and organisms having increased genomic stability. While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

INCORPORATION BY REFERENCE

All publications, patents and sequence database entries mentioned herein, including those items listed below, are hereby incorporated by reference in their entirety as if each individual publication or patent was specifically and individually indicated to be incorporated by reference. In case of conflict, the present application, including any definitions herein, will control.

The invention claimed is:

1. A method for assembling nucleic acid segments, the method comprising
providing a first and second population of nucleic acids, each population having at least a first, second, third and fourth restriction sites, wherein each population comprises at its 5' end a 5' activation sequence located between the first and second restriction sites and at its 3' end a 3' activation sequence located between the third and fourth restriction sites;
generating a first population of nucleic acid segments having the 5' activation sequence but lacking the 3' activation sequence by digesting the first population of nucleic acids using a first set of restriction enzymes that cleave the nucleic acids at the first and third restriction sites;
generating a second population of nucleic acid segments having the 3' activation sequence but lacking the 5' activation sequence by digesting the second population of nucleic acids using a second set of restriction enzymes that cleave the nucleic acids at the second and fourth restriction sites;
combining the first and second populations of nucleic acid segments with a first linearized nucleic acid vector that is digested with one or more restriction enzymes that produce restriction site overhangs that are complementary to the overhangs generated by the first and fourth restriction enzymes on the first and second populations of nucleic acid segments, wherein the first linearized nucleic acid vector comprises (i) at its 3' end a coding sequence of a first marker gene 5' of the first restriction site, and (ii) at its 5' end a coding sequence of a second marker gene 3' of the fourth restriction site, and
isolating ligated first nucleic acid vectors that express the first and the second marker genes, wherein expression of the first and the second marker genes is indicative of correct assembly of the first and second populations of nucleic acid segments and wherein expression of the first marker gene is regulated by the first activation sequence and expression of the second marker gene is regulated by the second activation sequence.

2. The method of claim 1, further comprising
digesting a third population of nucleic acids having at least first, second, third and fourth restriction sites, using the first set of restriction enzymes that cleave the nucleic acids at the first and third restriction sites,
digesting a fourth population of nucleic acids having at least first, second, third and fourth restriction sites, using the second set of restriction enzymes that cleave the nucleic acids at the second and fourth sites, wherein the third and fourth populations of nucleic acids comprise a 5' first activation sequence located between the first and second restriction sites and a 3' second activation sequence located between the third and fourth restriction sites, and digestion of the third population results in a third population of nucleic acid segments that comprises the first activation sequence but lacks the second activation sequence, and digestion of the fourth population results in a fourth population of nucleic acid segments that lacks a first activation sequence and comprises a second activation sequence,
combining in the presence of a ligase the third and fourth populations of nucleic acid segments with a second nucleic acid vector that is digested with one or more restriction enzymes that produce restriction site overhangs that are complementary to the overhangs generated by the first and fourth restriction enzymes on the third and fourth populations of nucleic acid segments, wherein the second nucleic acid vector comprises a coding sequence of a first marker gene 5' of the first restriction site and a coding sequence of a second marker gene 3' of the fourth restriction site,
selecting for ligated second nucleic acid vectors that express the first and the second marker genes, wherein expression of the first and the second marker genes is indicative of correct assembly of the third and fourth populations of nucleic acid segments and wherein expression of the first marker gene is regulated by the first activation sequence and expression of the second marker gene is regulated by the second activation sequence,
digesting the ligated second nucleic acid vector with restriction enzymes that cleave at the second and fourth restriction sites to release a fifth population of nucleic acid segments lacking a first activation sequence and comprising a second activation sequence,
digesting the ligated first nucleic acid vector with restriction enzymes that cleave at the first and third restriction sites to release a sixth population of nucleic acid segments comprising a first activation sequence and lacking a second activation sequence, and
combining the fifth and sixth populations of nucleic acid segments with a third nucleic acid vector digested with one or more restriction enzymes that produce restriction site overhangs that are complementary to the overhangs generated by the first and fourth restriction enzymes on the fifth and sixth populations of nucleic acid segments, wherein the third nucleic acid vector comprises a coding sequence of a third marker gene 5' of the first restriction site and a coding sequence of a fourth marker gene 3' of the fourth restriction site, and
selecting for ligated third nucleic acid vectors that express the third and fourth marker genes, wherein expression of the third and fourth marker genes is indicative of correct assembly of the fifth and sixth populations of nucleic acid segments and wherein expression of the first marker gene is regulated by the first activation sequence and expression of the second marker gene is regulated by the second activation sequence.

3. A method for assembling nucleic acid segments, the method comprising
providing a first and second population of nucleic acids, each population having at least first, second, third and fourth restriction sites, wherein each population comprises at its 5' end a 5' promoter sequence located between the first and second restriction sites and at its 3' end a 3' promoter sequence located between the third and fourth restriction sites, wherein the 5' and 3' promoter sequences are in opposite orientation to each other;

generating a first population of nucleic acid segments having the 5' promoter sequence but lacking the 3' promoter sequence by digesting the first population of nucleic acids using a first set of restriction enzymes that cleave the nucleic acids at the first and third restriction sites, generating a second population of nucleic acid segments having the 3' promoter sequence but lacking the 5' promoter sequence by digesting the second population of nucleic acids using a second set of restriction enzymes that cleave the nucleic acids at the second and fourth restriction sites, combining in the presence of a ligase the first and second populations of nucleic acid segments with a first linearized nucleic acid vector that is digested with restriction enzymes that cleave at the first and fourth restriction sites, wherein the first linearized nucleic acid vector comprises (i) at its 3' end a coding sequence of a first marker gene 5' of the first restriction site, wherein the first marker gene expression is regulated by the 5' promoter sequence, and (ii) at its 5' end a coding sequence of a second marker gene 3' of the fourth restriction site, wherein the second marker gene is regulated by the 3' promoter sequence, and selecting for ligated first nucleic acid vectors that express the first and the second marker genes, wherein expression of the first and the second marker genes is indicative of correct assembly of the first and second populations of nucleic acid segments.

4. The method of claim 2, further comprising digesting a third population of nucleic acids having at least first, second, third and fourth restriction sites, using a first set of restriction enzymes that cleave the nucleic acids at the first and third sites, digesting a fourth population of nucleic acids having at least first, second, third and fourth restriction sites, using a second set of restriction enzymes that cleave the nucleic acids at the second and fourth sites, wherein the third and fourth populations of nucleic acids comprise a 5' promoter sequence located between the first and second restriction sites and a 3' promoter sequence between the third and fourth restriction sites, and digestion of the third population results in a third population of nucleic acid segments that comprises the 5' promoter sequence but lacks the 3' promoter sequence, and digestion of the fourth population results in a fourth population of nucleic acid segments that lacks a 5' promoter sequence and comprises a 3' promoter sequence, combining in the presence of a ligase the third and fourth populations of nucleic acid segments with a second nucleic acid vector that is digested with restriction enzymes that cleave at the first and fourth restriction sites, wherein the second nucleic acid vector comprises a coding sequence of a first marker gene 5' of the first restriction site, wherein the first marker gene expression is regulated by the 5' promoter sequence, and a coding sequence of a second marker gene 3' of the fourth restriction site, wherein the second marker gene is regulated by the 3' promoter sequence, selecting for ligated second nucleic acid vectors that express the first and the second marker genes, wherein expression of the first and the second marker genes is indicative of correct assembly of the third and fourth populations of nucleic acid segments, digesting the ligated second nucleic acid vector with restriction enzymes that cleave at the second and fourth restriction sites to release a fifth population of nucleic acid segments lacking a 5' promoter sequence and comprising a 3' promoter sequence, digesting the ligated first nucleic acid vector with restriction enzymes that cleave at the first and third restriction sites to release a sixth population of nucleic acid segments comprising a 5' promoter sequence and lacking a 3' promoter sequence, and combining the fifth and sixth populations of nucleic acid segments with a third nucleic acid vector digested with restriction enzymes that cleave at the first and fourth restriction sites and having a third marker gene coding sequence 5' of the first restriction site, wherein the third marker gene expression is regulated by the 3' promoter sequence, and a fourth marker gene coding sequence 3' of the fourth restriction site, wherein the fourth marker gene is regulated by the 5' promoter sequence, and selecting for ligated third nucleic acid vectors that express the third and fourth marker genes, wherein expression of the third and fourth marker genes is indicative of correct assembly of the fifth and sixth populations of nucleic acid segments.

5. The method of claim 1, wherein the first and second marker genes are antibiotic resistance genes.

6. The method of claim 2, wherein the first, second, third and fourth marker genes are antibiotic resistance genes.

7. The method of claim 1, wherein the restriction enzymes are type II restriction enzymes or type IIS restriction enzymes.

8. The method of claim 1, wherein the restriction enzymes that cleave the first restriction and fourth restriction sites are type II restriction enzymes, and the restriction enzymes that cleave the second and third restriction sites are type IIS restriction enzymes.

9. The method of claim 1, wherein the restriction enzymes that cleave the first, second, third, and fourth sites are type II restriction enzymes.

10. The method of claim 1, wherein the first, second, third and fourth populations of nucleic acids are cloned nucleic acids or PCR-derived nucleic acids.

11. The method of claim 1, wherein the first, second, third and fourth populations of nucleic acids comprise nucleic acids of about 1 kb in length.

12. The method of claim 2, further comprising digesting the ligated first nucleic acid vectors that express the first and the second marker genes using restriction enzymes that cleave at the first and fourth restriction sites in order to release an assembled nucleic acid.

13. The method of claim 2, further comprising digesting the ligated third nucleic acid vectors that express the third and fourth marker genes using restriction enzymes that cleave at the first and fourth restriction sites in order to release an assembled nucleic acid.

14. The method of claim 12, wherein the assembled nucleic acid is about 50 kb in length.

15. The method of claim 12, wherein the assembled nucleic acid is about 100 kb in length.

16. The method of claim 1, wherein the first activation sequence is a promoter, terminator or other activation sequence or fragment thereof.

17. The method of claim 1, wherein the second activation sequence is a promoter, terminator or other activation sequence or fragment thereof.

18. The method of claim 1, wherein the first marker gene is a selectable marker.

19. The method of claim 1, wherein the second marker gene is a selectable marker.

20. A method of assembling a nucleic acid, the method comprising a plurality of consecutive alternating assembly cycles, wherein each alternating assembly cycle comprises:
   a) combining a first nucleic acid insert with a second nucleic acid insert and a first vector, wherein the first nucleic acid insert comprises a 5' first portion of a target sequence and at its 5' end a first activation sequence or fragment thereof, the second nucleic acid insert comprises a second portion of the target sequence and at its 3' end a second activation sequence or fragment thereof, and the first linearized vector comprises a first activatable marker at its 3' end and a second activatable marker at its 5' end;
   b) selecting for correct assembly of the first and second nucleic acid inserts in the first vector by selecting for activation of the first and second activatable markers, wherein correct assembly results in activation of the first activatable marker by the first activation sequence and activation of the second activatable marker by the second activation sequence;
   c) isolating from step b) an assembled nucleic acid comprising the first and second portions of the target sequence and the first activation sequence, but not the second activation sequence;
   d) combining the nucleic acid of step c) with a third nucleic acid insert and a second vector, wherein the third nucleic acid insert comprises a third portion of the target sequence and the second activation sequence at its 3' end, and the second linearized vector comprises a third activatable marker at its 3' end and a fourth activatable markers at its 5' end;
   e) selecting for correct assembly of the nucleic acid of step c) and the third nucleic acid insert in the second vector by selecting for activation of the third and fourth activatable markers, wherein correct assembly results in activation of the third activatable marker by the first activation sequence and activation of the fourth activatable marker by the second activation sequence; and
   f) isolating from step e) an assembled nucleic acid comprising the first, second, and third portions of the target sequence and the first activation sequence, but not the second activation sequence; wherein the nucleic acid of step f) can be combined in a subsequent assembly cycle starting at step a) with a with a fourth nucleic acid insert and the first linearized vector, wherein the fourth nucleic acid insert comprises a 3' fourth portion of the target sequence and the second activation sequence.

21. The method of claim 20 wherein at least one nucleic acid insert comprises a non-functional activation sequence and wherein correct assembly of the target sequence results in the assembly of a functional activation sequence.

* * * * *